United States Patent
Pinsky et al.

(10) Patent No.: US 6,315,995 B1
(45) Date of Patent: Nov. 13, 2001

(54) METHODS FOR TREATING AN ISCHEMIC DISORDER AND IMPROVING STROKE OUTCOME

(75) Inventors: David J. Pinsky, Riverdale; David Stern, Great Neck, both of NY (US); Ann Marie Schmidt, Franklin Lakes, NY (US); Eric Rose, Tenafly, NJ (US); Robert A. Solomon, Palisades, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/053,871

(22) Filed: Apr. 1, 1998

Related U.S. Application Data

(63) Continuation-in-part of application No. PCT/US97/17229, filed on Sep. 25, 1997, which is a continuation-in-part of application No. 08/721,447, filed on Sep. 27, 1996, now abandoned.

(51) Int. Cl.$^7$ .......................... A61K 38/16; A61K 38/43; C12F 21/06

(52) U.S. Cl. .......................... 424/94.63; 435/69.1; 514/8; 424/94.1

(58) Field of Search .............................. 514/8; 435/69.1; 424/94.1, 94.63

(56) References Cited

U.S. PATENT DOCUMENTS 4,711,848 * 12/1987 Insley .

FOREIGN PATENT DOCUMENTS 2141642    3/1995 (CA).

OTHER PUBLICATIONS

Brandstetter et al., PNAS 92:9796–800, 1995.*
Benedict, C.R., et al. (1994) "Endothelial–Dependent Procoagulant and Anticoagulant Mechanisms," *Texas Heart Journal*, 21: 86–90.
Connolly E. S. Jr. et al. (1996) Cerebral Protection in Homozygous Null ICAM–1 Mice After Middle Cerebral Artery Occlusion, *J. Clin. Invest.*, 97: 209–216.
Pinsky, D. J. et al. (1996) Hypoxia–induced Exocytosis of Endothelial Cell Weibel–Palade Bodies, a mechanism for rapid neutrophil recruitment after cardiac preservation, *J. Clin. Invest.*, 97: 493–500.
Connolly, E. S. Jr. et al. (1996) "Procedural and Strain–related Variables Significantly Affect Outcome in a Murine Model of Focal Cerebral Ischemia." *Neurosurgery*, 38: 523–532.

Benedict, C. R. et al. (1991) "Active Site–Blocked Factor IXa Prevents Intravascular Thrombus Formation in the Coronary Vasculature Without Inhibiting Extravascular Coagulation in a Canine Thrombosis Model," *J. Clin. Invest.*, 88: 1760–1765.
Kim, J. S. et al. (1995) "Adhesive Glycoproteins CD11a and CD18 are Upregulated in the Leukocytes from Patients with Ischemic Stroke and Transient Ischemic Attacks," *Journal of the Neurological Sciences*, 128: 45–50.
Mayevsky, A. et al. (1995) "Multiparametic Monitoring of the Awake Brain Exposed to Carbon Monoxide." *J. Appl. Physiol,*, 78: 1188–1196.
Bronner, L. L. et al. (1995) "Preliminary Prevention of Stroke." *The New England J. Med.*, 333: 1392–1400.
Fassbender, K. et al. (1995) "Circulating Selectin–and Immunoglobulin–Type Adhesion Molecules in Acute Ischemic Stroke." *Stroke*, 26: 1361–1364.
Seekamp, A. et al. (1994) "Role of Selectins in Local and Remote Tissue Injury Following Ischemia and Reperfusion," *Am. J. Pathol.*, 44: 592–598.
Jerome, S. N. et al. (1994) "P–selectin and ICAM–1–Dependent Adherence Reactions: Role in the Genesis of Postichemic No–Reflow." *Am. J. Physiol.*, 226: H1316–H1321.
Schroeter, M. et al. (1994) "Local Immune Responses in the Rat Cerebral Cortex after Middle Cerebral Artery Occlusion." *J. Neuroimmunol.*, 55: 195–203.
Okada, Y. et al. (1994) "P–selectin and Intercellular Adhesion Molecule–1 Expression After Focal Brain Ischemia and Reperfusion." *Stroke*, 25: 202–211.
Dawson, T. M. & Snyder, S. H. (1994) "Gases as Biological Messengers: Nitric Oxide and Carbon Monoxide in the Brain." *J. Neuroscience*, 14(9): 5147–5159.
Carlos, T. M. & Harlan, J. M. (1994) "Leukocyte–Endothelial Adhesion Molecules." *Blood*, 24: 2068–2102.
Verma, A. et al. (1993) "Carbon Monoxide: A Putative Neural Messenger." *Science*, 259: 381–384.
Weyrich, A. S. et al. (1993) "In Vivo Neutralization of P–Selectin Protects Feline Heart Endothelium in Myocardial Ischemia and Reperfusion Injury." *J. Clin. Invest.*, 91: 2620–2629.

(List continued on next page.)

*Primary Examiner*—David Saunders
*Assistant Examiner*—Amy DeCloux
(74) *Attorney, Agent, or Firm*—John P. White; Cooper & Dunham LLP

(57) ABSTRACT

The present invention provides for a method for treating an ischemic disorder in a subject which comprises administering to the subject a pharmaceutically acceptable Factor IXa compound in a sufficient amount over a sufficient time period so as to treat the ischemic disorder in the subject. The invention further provides a method for treating an ischemic disorder in a subject which comprises administering to the subject a pharmaceutically acceptable form of inactivated Factor IXa in a sufficient amount over a sufficient period of time to inhibit coagulation so as to treat the ischemic disorder in the subject.

7 Claims, 26 Drawing Sheets

OTHER PUBLICATIONS

Brown, S. D. & Piantadosi, C. A. et al. (1992) "Recovery of Energy Metabolism in Rat After Carbon Monoxide Hyposia." *J. Clin. Invest.,* 89: 666–672.

Kochaneck, P. M. & Hallenbeck, J. M. (1992) "Polymorphonuclear Leukocytes and Monocytes/Macrophages in the Pathogenesis of Cerebral Ischemia and Stroke." *Stroke,* 23: 1367–1379.

Ishimaru, H. et al. (1991) "Effects of Successive Carbon Monoxide Exposures on Delayed Neuronal Death in Mice Under the Maintenance of Normal Body Temperature." *Biochem. Biophys. Res. Comm.,* 179(2): 836–840.

* cited by examiner 5 mm

METHODS FOR TREATING AN ISCHEMIC DISORDER AND IMPROVING STROKE OUTCOME

This application is a continuation-in-part of PCT International Application No. PCT/US97/17229, filed Sep. 25, 1997, which is a continuation-in-part of U.S. Ser. No. 08/721,447, filed Sep. 27, 1996 now abandoned which applications are hereby incorporated by reference in their entireties.

The invention disclosed herein was made with Government support under National Institutes of Health, National Heart, Lung and Blood Institute award HL55397 of the Department of Health and Human Services. Accordingly, the U.S. Government has certain rights in this invention.

Throughout this application, various publications are referenced following certain Examples and within the Detailed Description of the Invention section. The disclosures of these publications in their entireties are hereby incorporated by reference into this application in order to more fully describe the state of the art as known to those skilled therein as of the date of the invention described and claimed herein.

BACKGROUND OF THE INVENTION

As described in Colman et al., Editors, *Hemostasis and Thrombosis*, Third Edition, J.B. Lippincott Company, Philadelphia, 1994, pages 33–36, 62–63 and 94–105, human Factor IX is a 415 amino acid glycoprotein ($Mr \approx 57,000$, 17% carbohydrate). Factor IX is a proenzyme that has no catalytic activity. During the coagulation cascade, it is cleaved by Factor XIa to produce catalytically active Factor IXa. A wide variety of Factor IX gene mutations are found in patients with hemophilia B. Among these are mutations in the enzyme active site, including a Ser365 to Arg mutation and mutations near His221. (Colman et al., page 63) These mutations affect the ability of the active site to proteolytically cleave its Factor X substrate. Mutations of Gly363 to Val were found to be functionally normal but unable to activate Factor X (Colman et al., page 104).

The gene for Factor IX has been identified, cDNA for Factor IX has been isolated, sequenced, and cloned into expression vectors, and recombinant Factor IX has been expressed. See, for example, Durachi et al., "Isolation and characterization of a cDNA coding for human Factor IX," Proc. Natl. Acad. Sci. USA 79: 6461, 1982 (GenBank Accession Nos. J00136 and 182690); Choo et al., "Molecular cloning of the gene for human anti-haemophilic factor Factor IX," Nature 299: 178, 1982; Anson et al., "the gene structure of human anti-haemophilic factor Factor IX," EMBO J. 3:1053, 1984; Yshitake et al., "Nucleotide Sequence of the gene for human Factor IX," Biochemistry 24:3736, 1985 (GenBank Accession No. 182,613); Anson et al., "Expression of active human clotting Factor IX from recombinant DNA clones in mammalian cells," Nature 315:683,1985; Busby et al., "Expression of active human Factor IX in transfected cells," Nature 316:271, 1985; de la Salle et al., "Active gamma carboxylated human Factor IX expressed using recombinant DNA techniques," Nature 316: 268, 1985; and Kaufman et al., "Expression, purification, and characterization of recombinant gamma-carboxylated factor IX synthesized in Chinese hamster ovary cells," J. Biol. Chem. 261:9622, 1986. See also Brownlee et al., UK Patent Application GB 2 125 409 A, published Mar. 7, 1984; Anson et al., U.S. Pat. No. 5,171,569, issued Dec. 15, 1992; Muelien U.S. Pat. No. 5,521,070, issued May 284 1996; Kaufman et al., U.S. Pat. No. 4,770,999, issued Sep. 13, 1988; and Barr et al., U.S. Pat. No. 5,460,950, issued Oct. 24, 1995.

In addition, Benedict et al. (1994) Texas Heart Institute Journal Vol 21, No. 1, pp 85–90 disclose that infusion of Factor IXai at concentrations sufficient to inhibit intravenous coagulation did not produce bleeding significantly different from that in control animals. Therefore, the invention disclosed herein was unexpected in view of this report.

SUMMARY OF THE INVENTION

The present invention provides a method for treating an ischemic disorder in a subject which comprises administering to the subject a pharmaceutically acceptable form of a Factor IXa compound in a sufficient amount over a sufficient period of time to inhibit coagulation so as to treat the ischemic disorder in the subject. The present invention provides a method for treating an ischemic disorder in a subject which comprises administering to the subject a pharmaceutically acceptable form of inactivated Factor IXa in a sufficient amount over a sufficient period of time to inhibit coagulation so as to treat the ischemic disorder in the subject.

BRIEF DESCRIPTION OF THE FIGURES

FIG. 1A. Suture based retraction system is shown in the diagram.

FIG. 1B. View through the operating microscope. The large vascular stump represents the external carotid artery, which is situated inferomedially in the operating field.

FIG. 1C. Photograph of heat-blunted occluding suture of the indicated gauge (5-0 [bottom] or 6-0 nylon [top]).

FIG. 1D. Schematic diagram of murine cerebrovascular anatomy, with thread in the anterior cerebral artery, occluding the middle cerebral artery at its point of origin.

Bottom Panel. Effects of strain on cerebral blood flow, measured by laser doppler flowmetry as relative flow over the infarcted territory compared with blood flow over the contralateral (noninfarcted) cortex. Strains included 129J (n=9), CD1 (n=11), and C57/Bl6 mice (n=11); *=$p<0.05$ vs 129J mice.

Figure 4A:
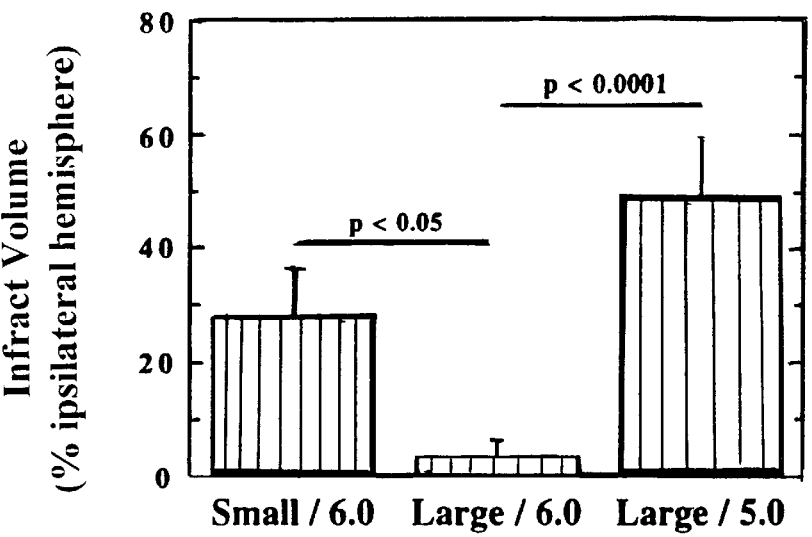
Figure 4B:
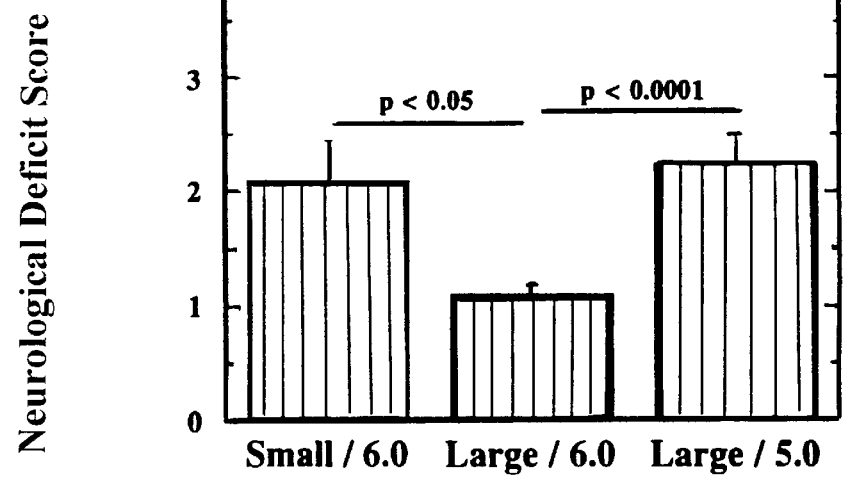
Figure 4C:
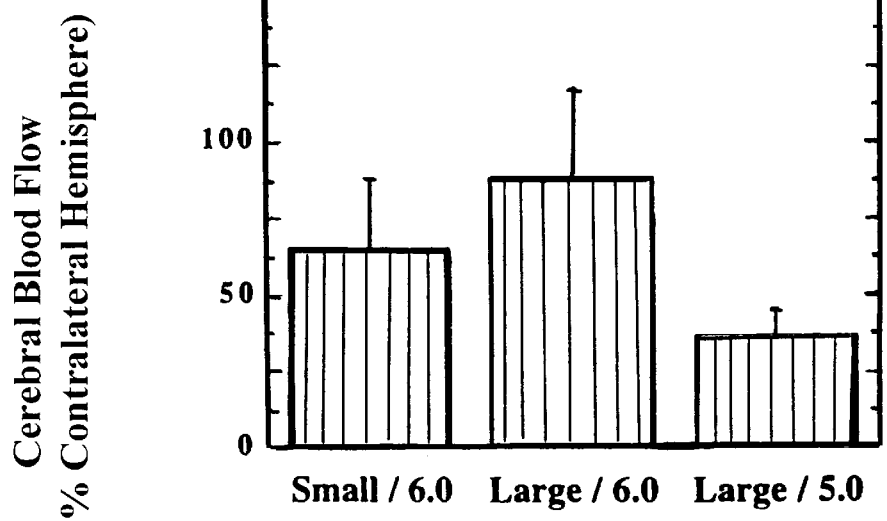

FIGS. 4A, 4B and 4C. Effects of animal size and diameter of the occluding suture on stroke outcome. Male CD-1 mice of the indicated sizes were subjected to middle cerebral artery occlusion (45 minutes) followed by reperfusion (24 hours) as described in the Methods section. Suture size (gauge) is indicated in each panel. Small animals (n=11) were those between 20–25 gm (mean 23 gm), and large animals were between 28–35 gm (mean 32 gm; n=14 for 6.0 suture, n=9 for 5.0 suture).

FIG. 4A. Effects of animal/suture size on infarct volume,

FIG. 4B. neurological deficit score, and

Figure 3:
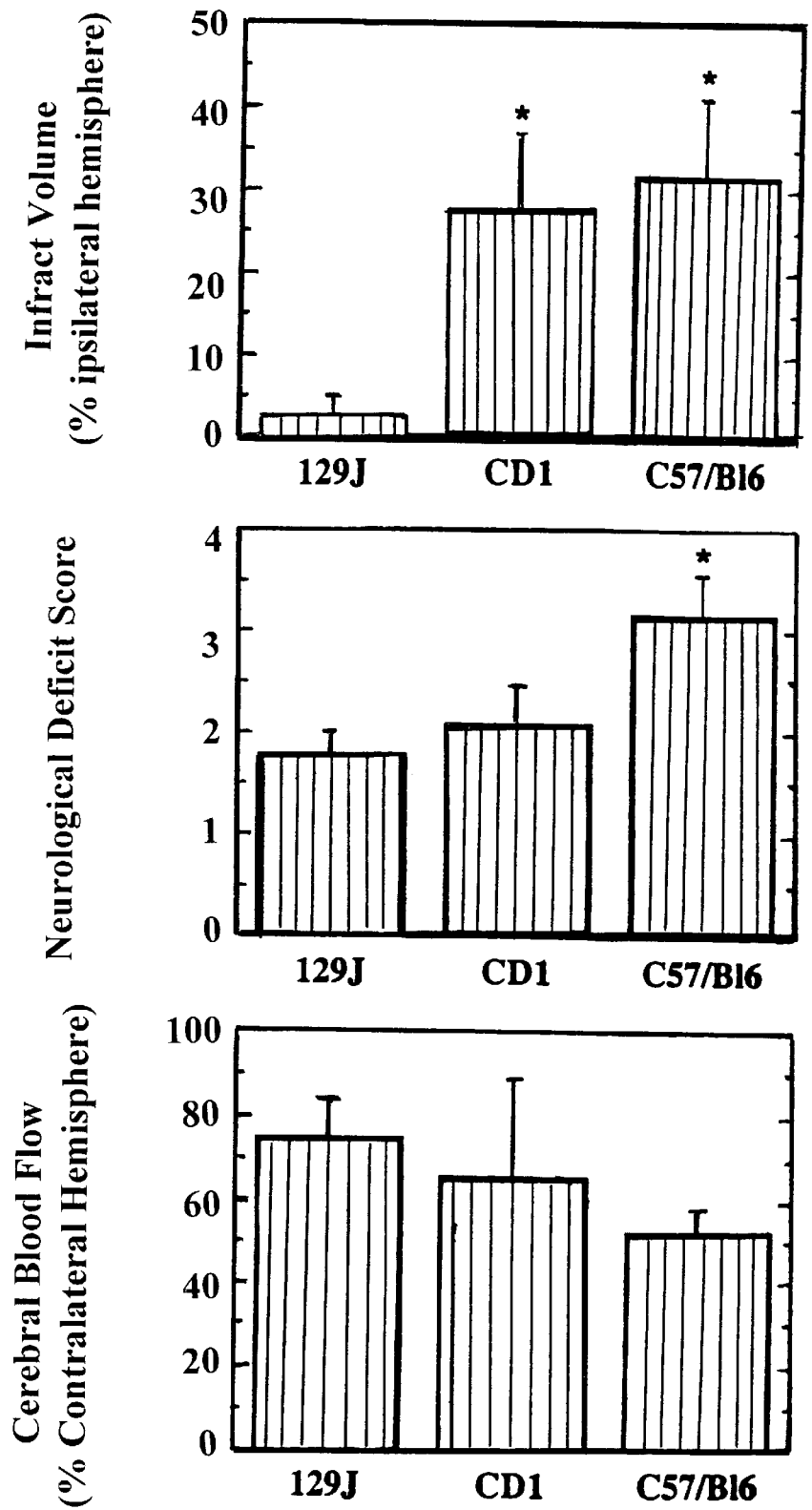
FIG. 3. Effects of mouse strain on stroke outcome. Mice (20–23 gm males) were subjected to 45 minutes of MCA occlusion (using 12 mm 6.0 occluding suture) followed by 24 hours of reperfusion, and indices of stroke outcome determined. Top Panel. Effects of strain on infarct volume, determined as a percentage of ipsilateral hemispheric volume, as described in the Methods section. Middle Panel. Effects of strain on neurological deficit score, graded from no neurologic deficit (0) to severe neurologic deficit (4), with scores determined as described in the Methods section.

FIG. 4C. cerebral blood flow, measured as described in FIG. 3. P values are as shown.

Figure 5A:
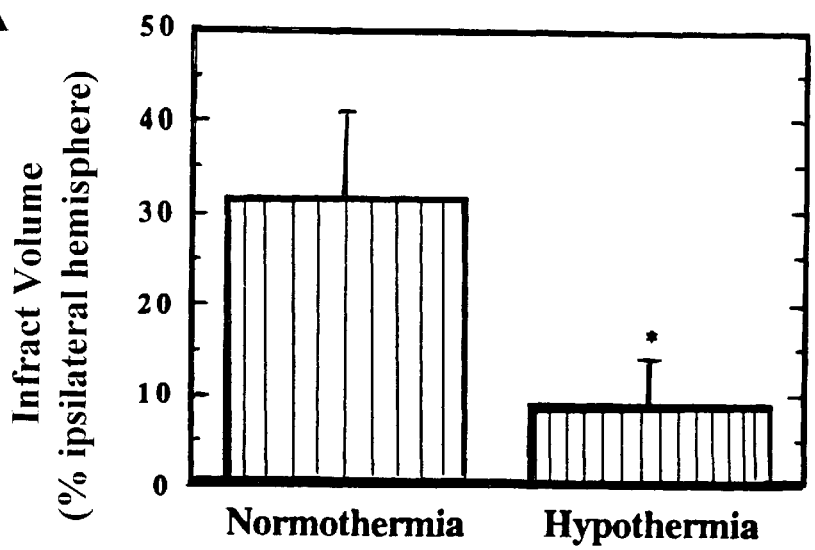
Figure 5B:
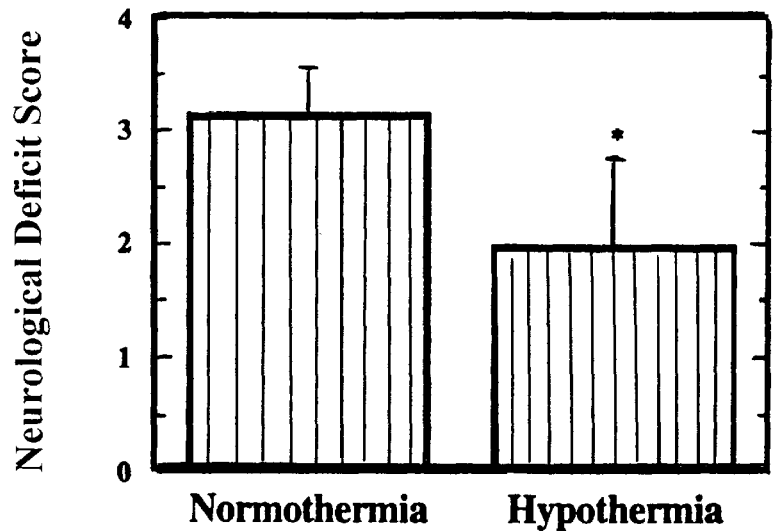
Figure 5C:
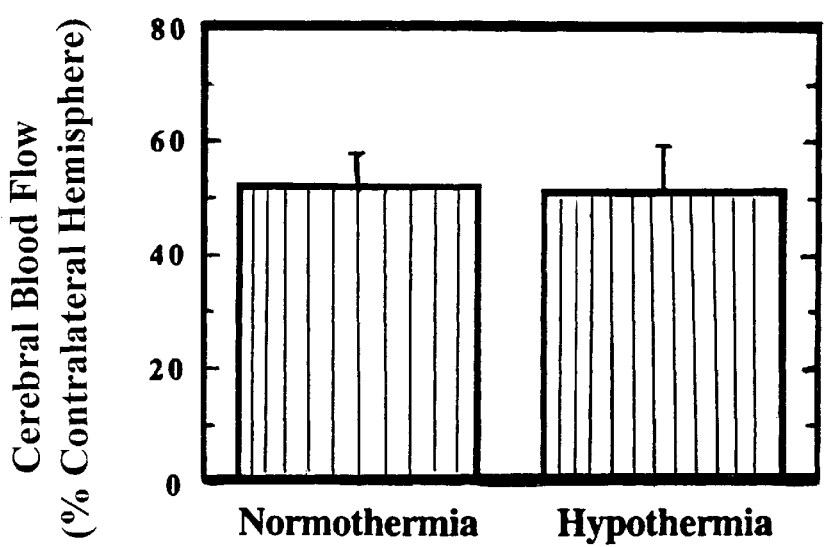

FIGS. 5A, 5B and 5C. Effects of temperature on stroke outcome. Male C57/Bl6 mice were subjected to 45 minutes of MCA occlusion (6.0 suture) followed by reperfusion. Core temperatures were maintained for 90 minutes at 37° C. (normothermia, n=11) using an intrarectal probe with a thermocouple-controlled heating device. In the second group (hypothermia, n=12), animals were placed in cages left at room temperature after an initial 10 minutes of normothermia (mean core temperature 31° C. at 90 minutes). In both groups, after this 90 minute observation period, animals were returned to their cages with ambient temperature maintained at 37° C. for the duration of observation. Twenty-four hours following MCA occlusion, indices of stroke outcome were recorded;

FIG. 5A. infarct volume,

FIG. 5B. neurological deficit score, and

FIG. 5C. cerebral blood flow, measured as described in FIG. 3. *=$p<0.05$ values are as shown.

Figure 6A:
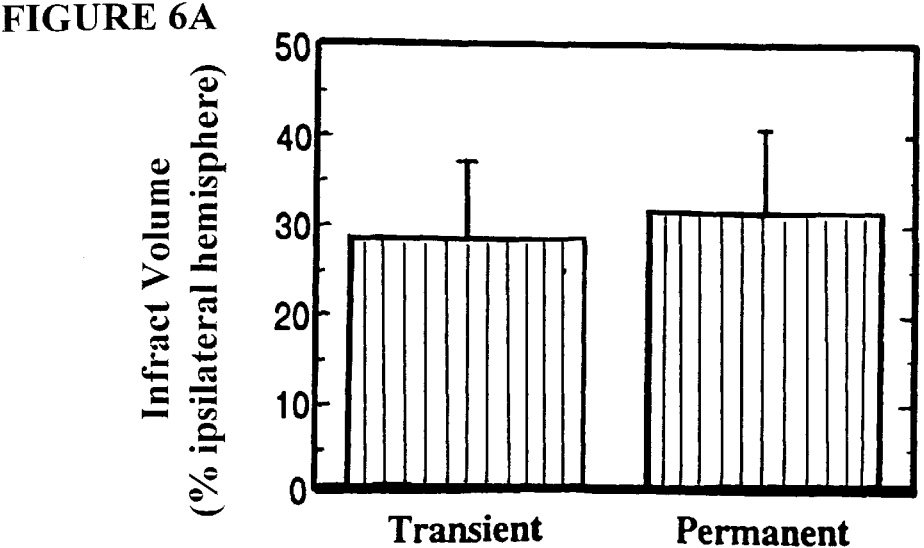
Figure 6B:
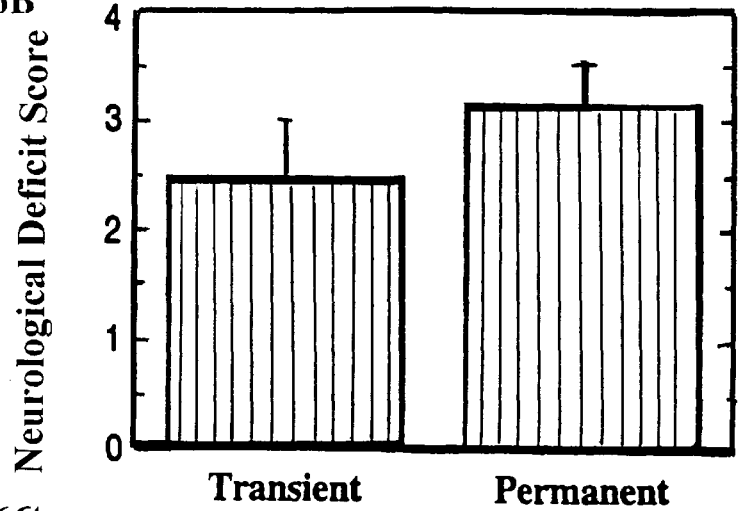
Figure 6C:
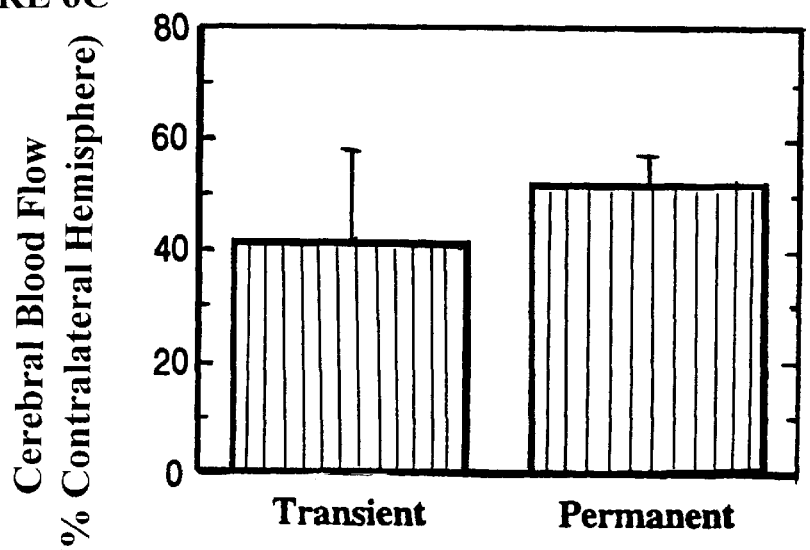

FIGS. 6A, 6B and 6C. Outcome comparisons between permanent focal cerebral ischemia and transient focal cerebral ischemia followed by reperfusion. The MCA was either occluded permanently (n=11) or transiently (45 minutes, n=17) with 6.0 gauge suture in 22 gram Male C57/Bl6 mice, as described in the Methods section. Twenty-four hours following MCA occlusion, indices of stroke outcome were recorded;

FIG. 6A. infarct volume,

FIG. 6B. neurological deficit score, and

FIG. 6C. cerebral blood flow, measured as described in FIG. 3.

FIGS. 7A–7F.

Figure 7A:
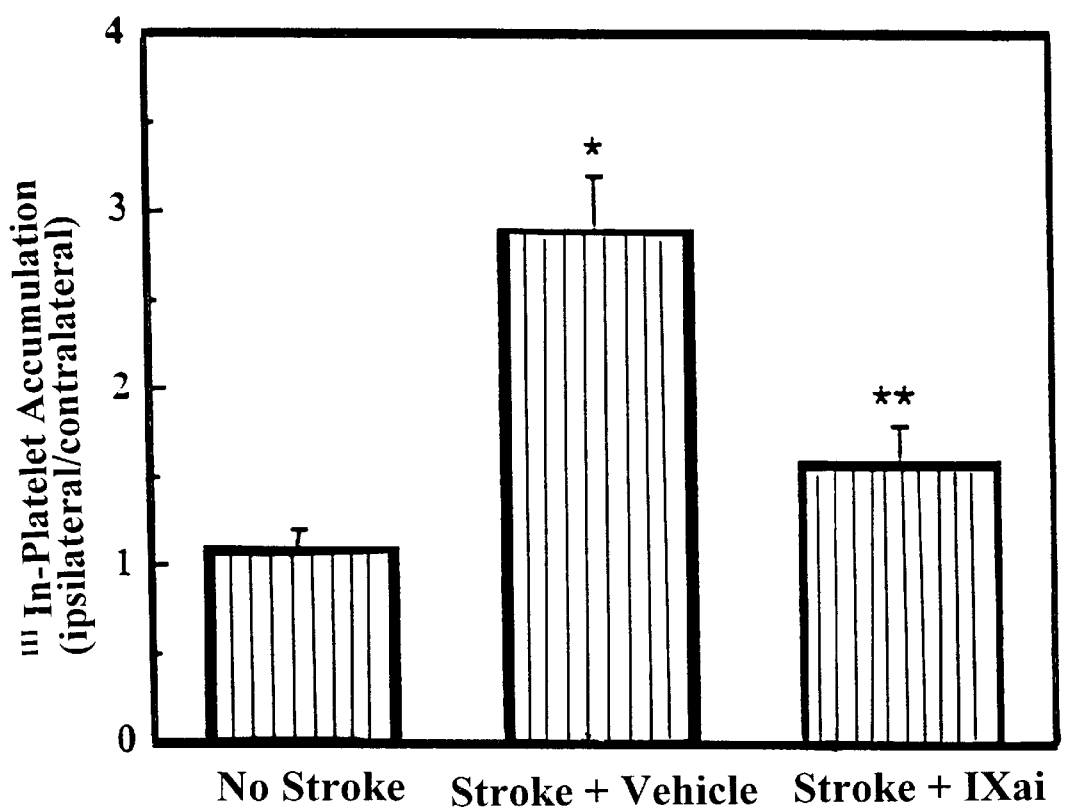

FIG. 7A. Effect of stroke and Factor IXai administration in stroke on the accumulation of radiolabeled platelets. [111]Indium-platelets were administered either in control animals without stroke (n=4), or in animals immediately prior to stroke with (n=7) or without preoperative administration of Factor IXai (300 μg/kg, n=7). Platelet accumulation is expressed as the ipsilateral cpm/contralateral cpm. Means±SEM are shown. *$p<0.05$ vs No Stroke; **$p<0.05$ vs Stroke+Vehicle.

Figure 7B:
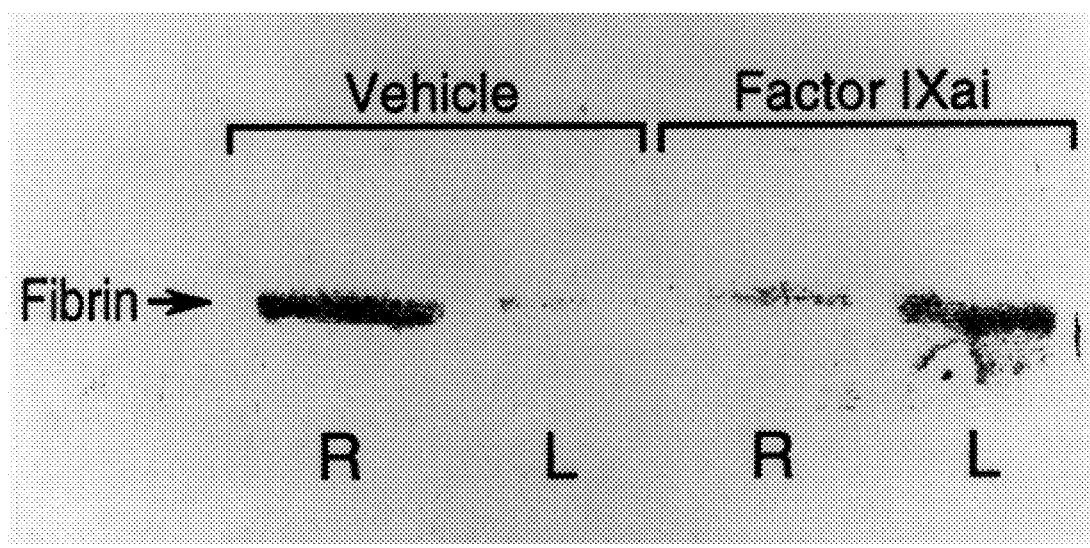
Figure 7C:
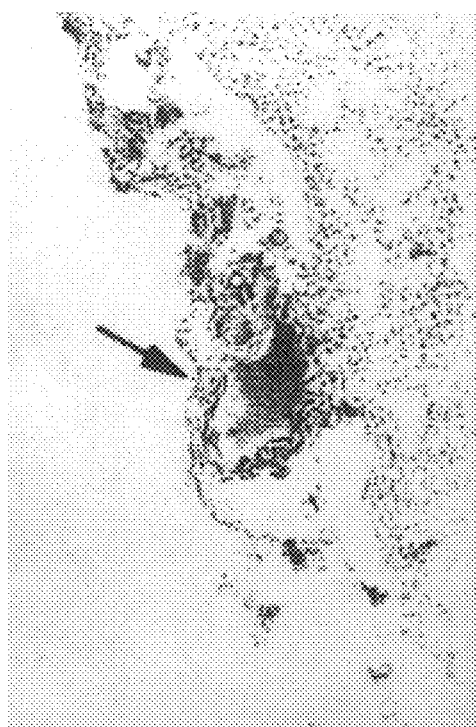
Figure 7D:
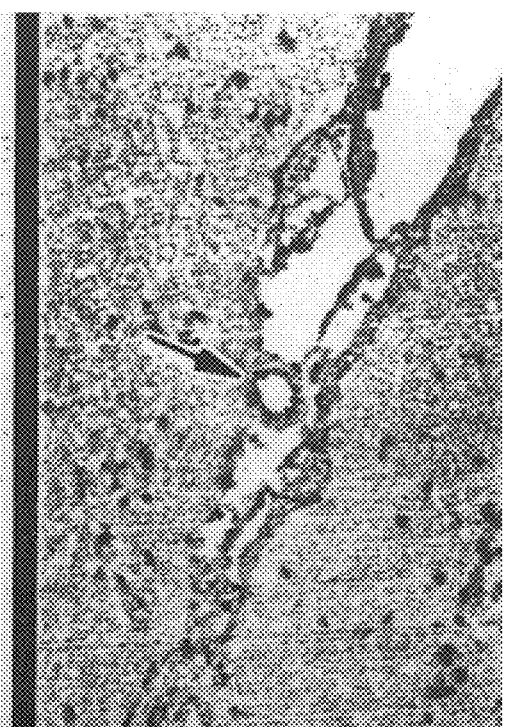
Figure 7E:
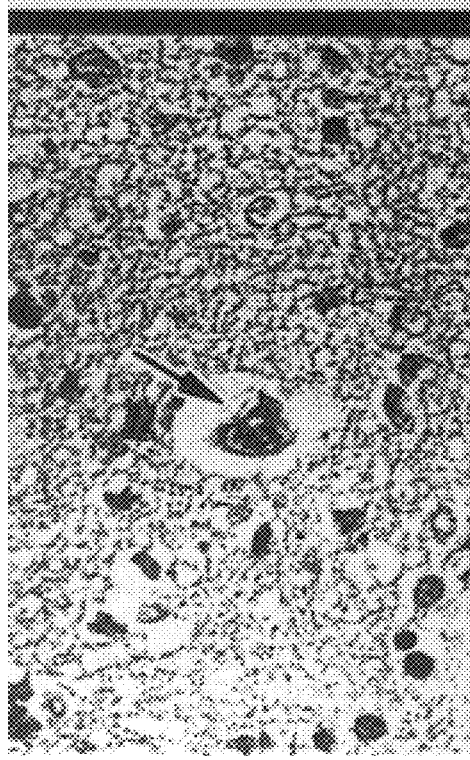
Figure 7F:
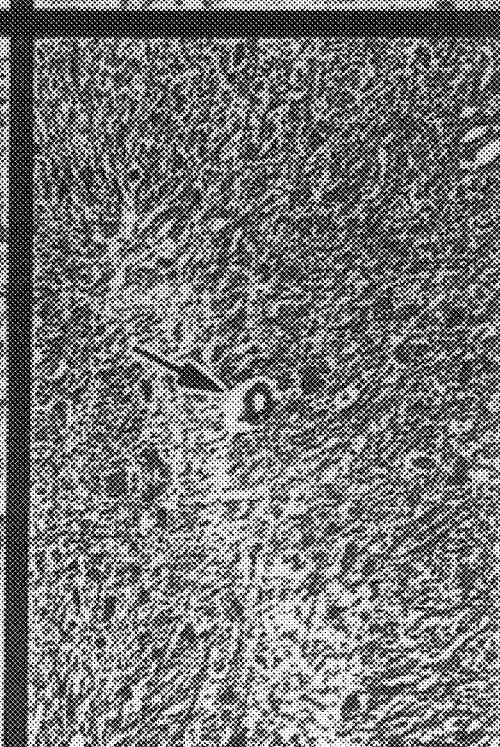

FIG. 7B. Accumulation of fibrin in infarcted cerebral tissue. Twenty-two hours following focal cerebral ischemia and reperfusion, a brain was harvested from a representative mouse which had been pretreated prior to surgery with either vehicle (leftmost two lanes) or Factor IXai (300 μg/kg, rightmost two lanes). The brains were divided into ipsilateral (R) and contralateral (L) hemispheres, and plasmin digestion performed to solubilize accumulated fibrin. Immunoblotting was performed using a primary antibody directed against a neoepitope expressed on the gamma—gamma chain dimer of crosslinked fibrin.

FIG. 7C–7F. Immunohistochemical identification of sites of fibrin formation in stroke. Using the same antibody as described in FIG. 2B to detect fibrin, brains were harvested from two mice following stroke (upper and lower panels each represent a mouse). Arrows identify cerebral microvessels. Note that in both ipsilateral hemispheres (left, FIGS. 7C and 7E), intravascular fibrin can be clearly identified by the red stain, which is not seen in the contralateral (right, FIGS. 7D and 7F), nonischemic hemispheres.

FIGS. 8A–8C.

Figure 8A:
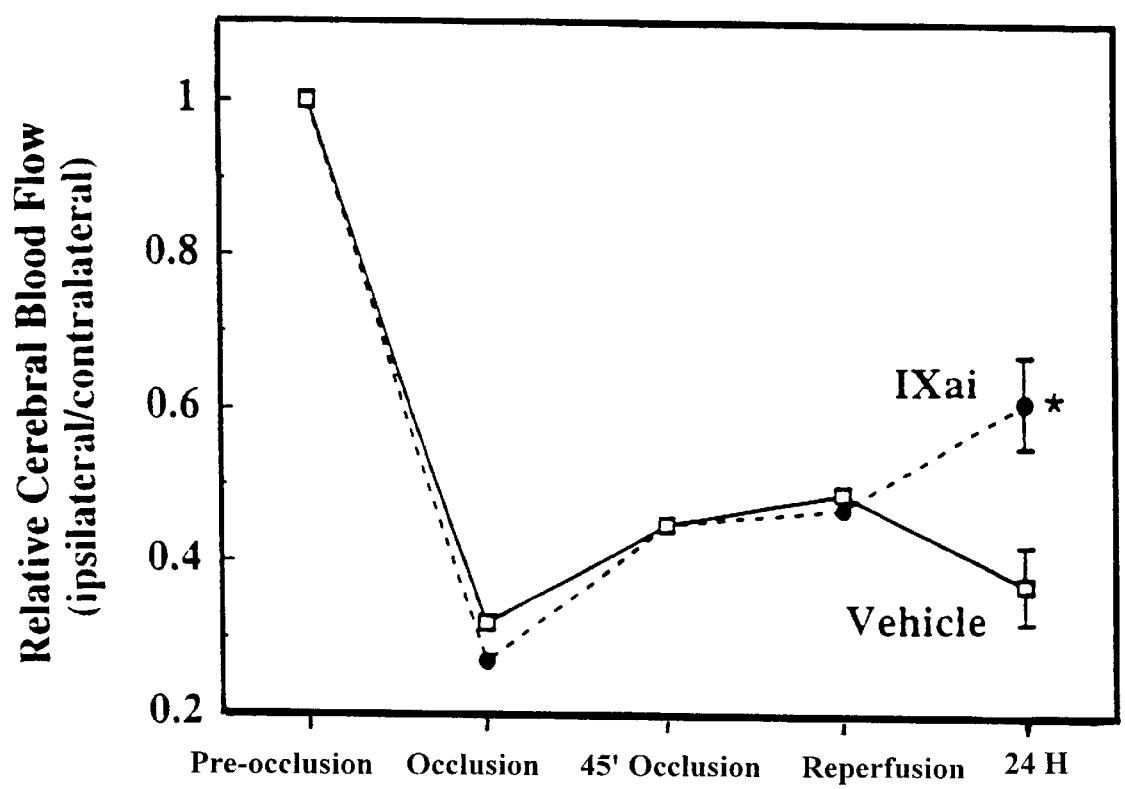

FIG. 8A. Effect of Factor IXai on relative CBF in a murine stroke model, measured by laser doppler. CBF in Factor IXai-treated animals (300 μg/kg, n=48, dashed line) is significantly higher at 24 hours than vehicle-treated controls (n=62). Means±SEM are shown. *$p<0.05$.

Figure 8B:
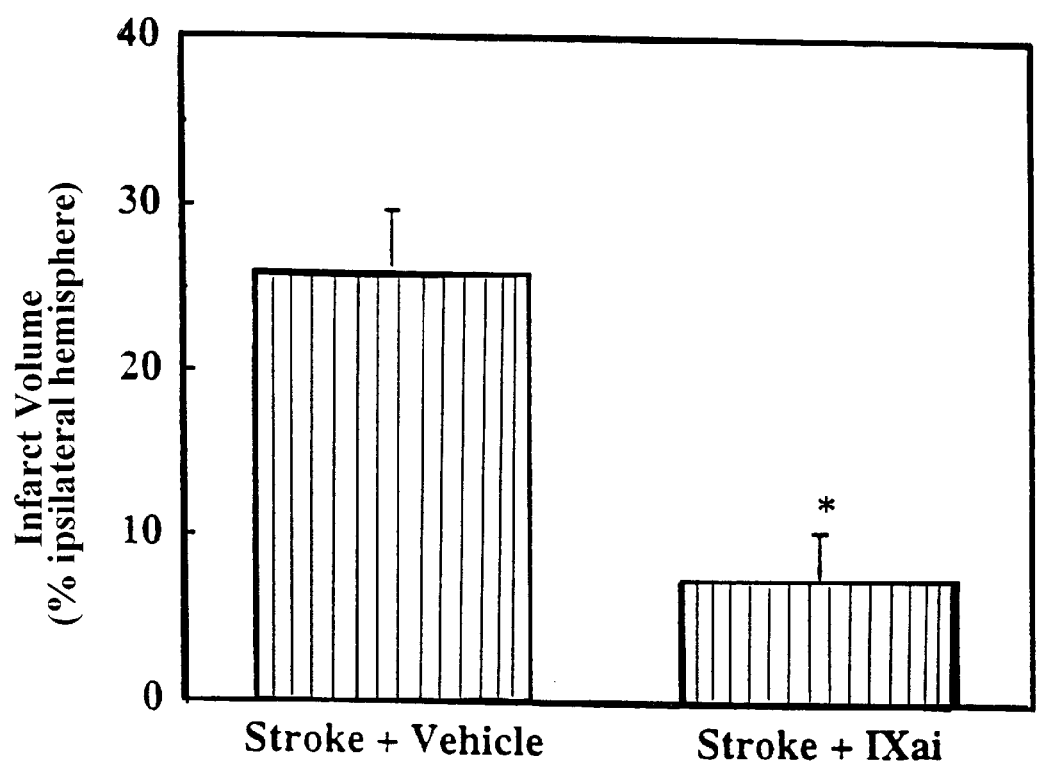

FIG. 8B. Effect of Factor IXai on infarct volumes in a murine stroke model, measured by TTC-staining of serial coronal sections. Animals were given vehicle (n=62) or Factor IXai (300 μg/kg, n=48). Means±SEM are shown. *$p<0.05$.

Figure 8C:
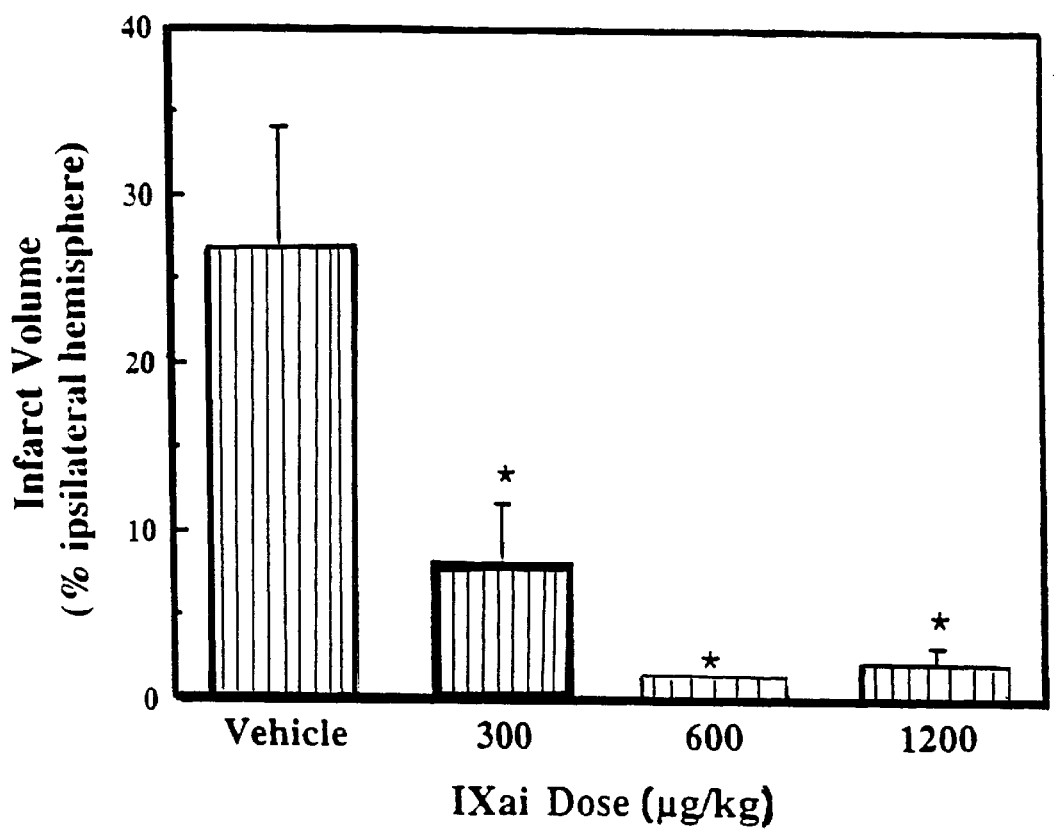

FIG. 8C. Dose-response of Factor IXai in stroke. Factor IXai was administered immediately prior to the onset of stroke, and cerebral infarct volumes determined as described in FIG. 8B above. N=62, 48, 6, and 6, for Vehicle, 300 μg/kg, 600 μg/kg, and 1200 μg/kg doses respectively. Means±SEM are shown. *$p<0.05$ vs vehicle-treated animals.

Figure 9A:
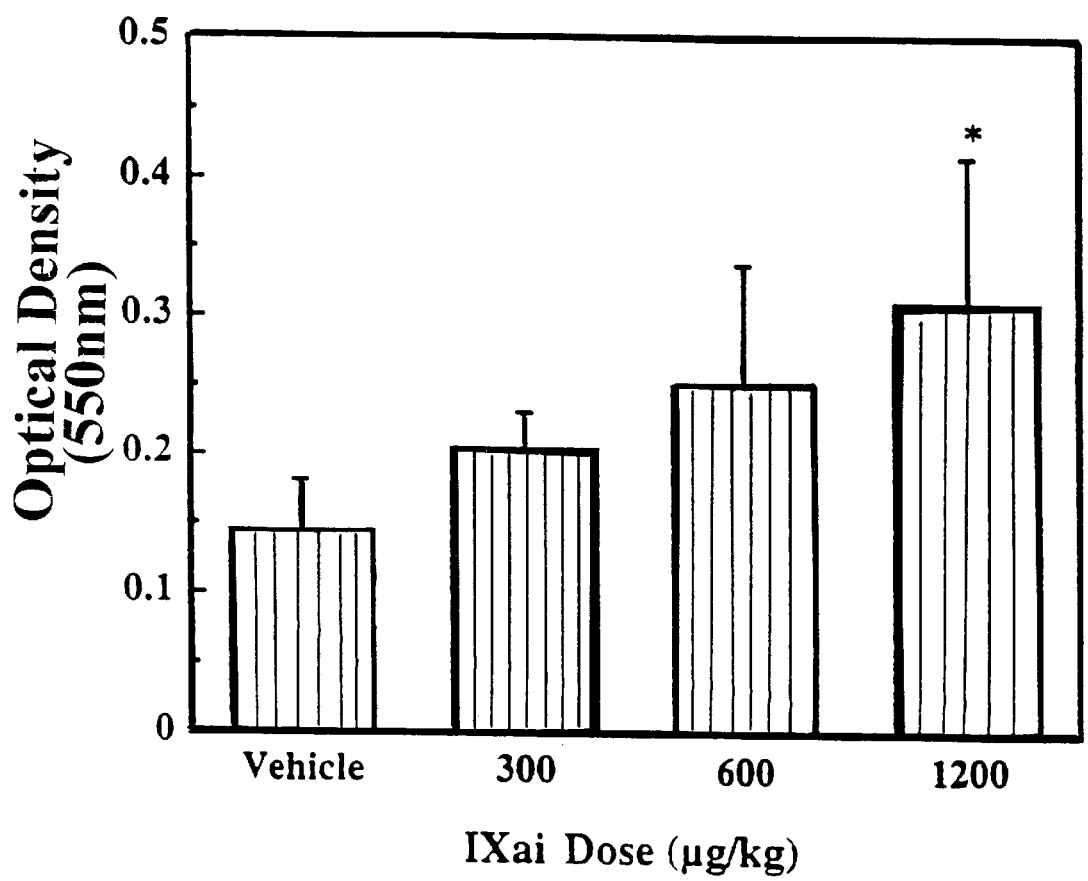
Figure 9B:
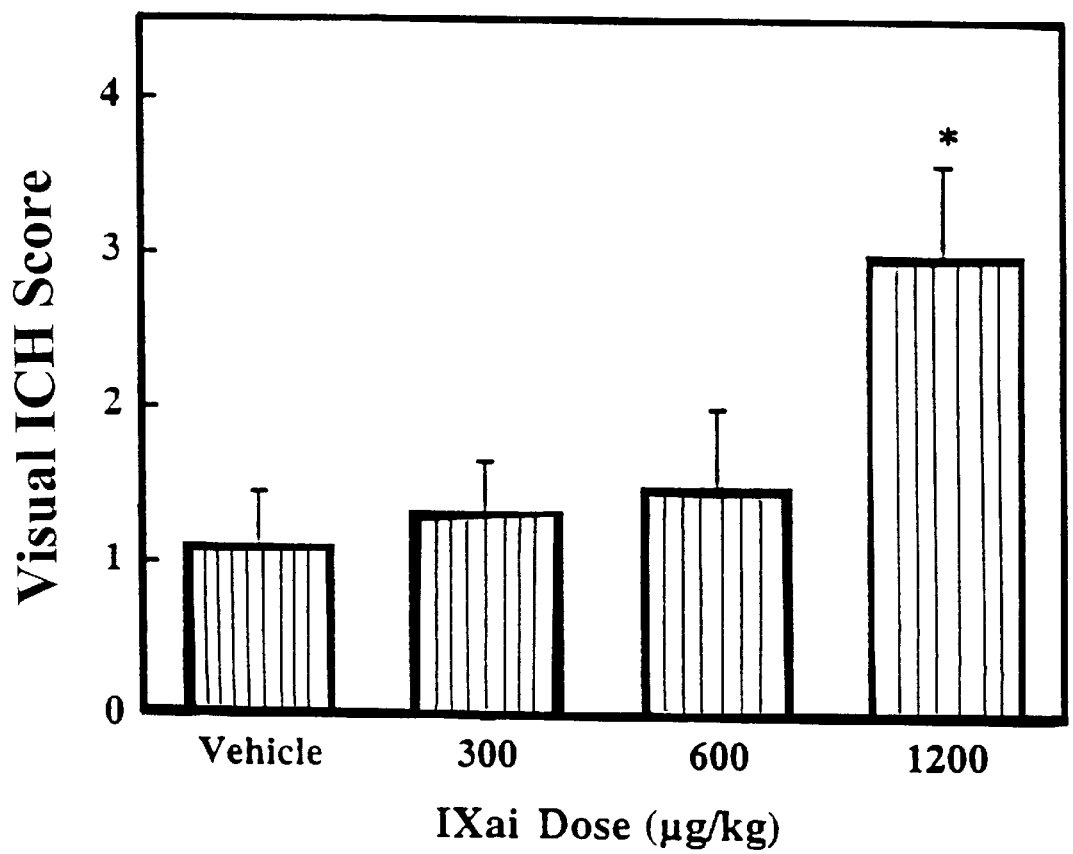

FIGS. 9A–9B. Effect of Factor IXai on Intracerebral hemorrhage.

FIG. 9A. Spectrophotometric hemoglobin assay was performed as described in the Methods section. O.D. at 550 nm is linearly related to brain hemoglobin content[11,12] (see references following example in which figure is discussed).

FIG. 9B. Visually-determined ICH score by a blinded observer, as described in the methods section. ICH score correlates with spectrophotometrically-determined brain hemoglobin content[11,12]. Means±SEM are shown. *$p<0.05$ vs vehicle-treated animals.

Figure 10:
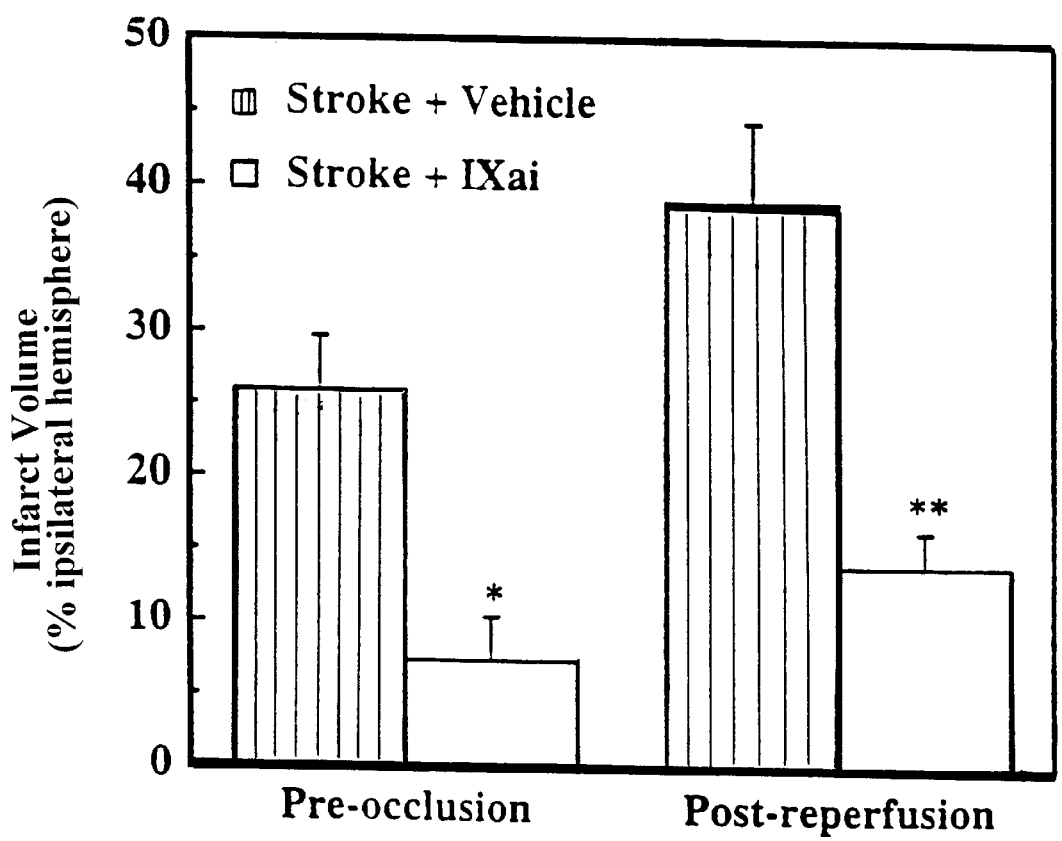

FIG. 10. Effect of timing of Factor IXai administration on cerebral infarct volumes when given after the onset of stroke. Mice were subjected to focal cerebral ischemia and reperfusion as described in the Methods section. The pre-occlusion administration (leftmost 2 bars) data is that shown in FIG. 8B. In additional experiments to determine the effects of Factor IXai administered after stroke, immediately following withdrawal of the intraluminal occluding suture, vehicle (normal saline, n=13) or Factor IXai (300 μg/kg, n=7) was administered intravenously. Cerebral infarct volumes (based on TTC-stained serial sections obtained at 22 hrs) were determined. Means±SEM are shown. *$p<0.05$, **$p<0.05$ vs vehicle-treated animals.

FIGS. 11A–11D.

Figure 11A:
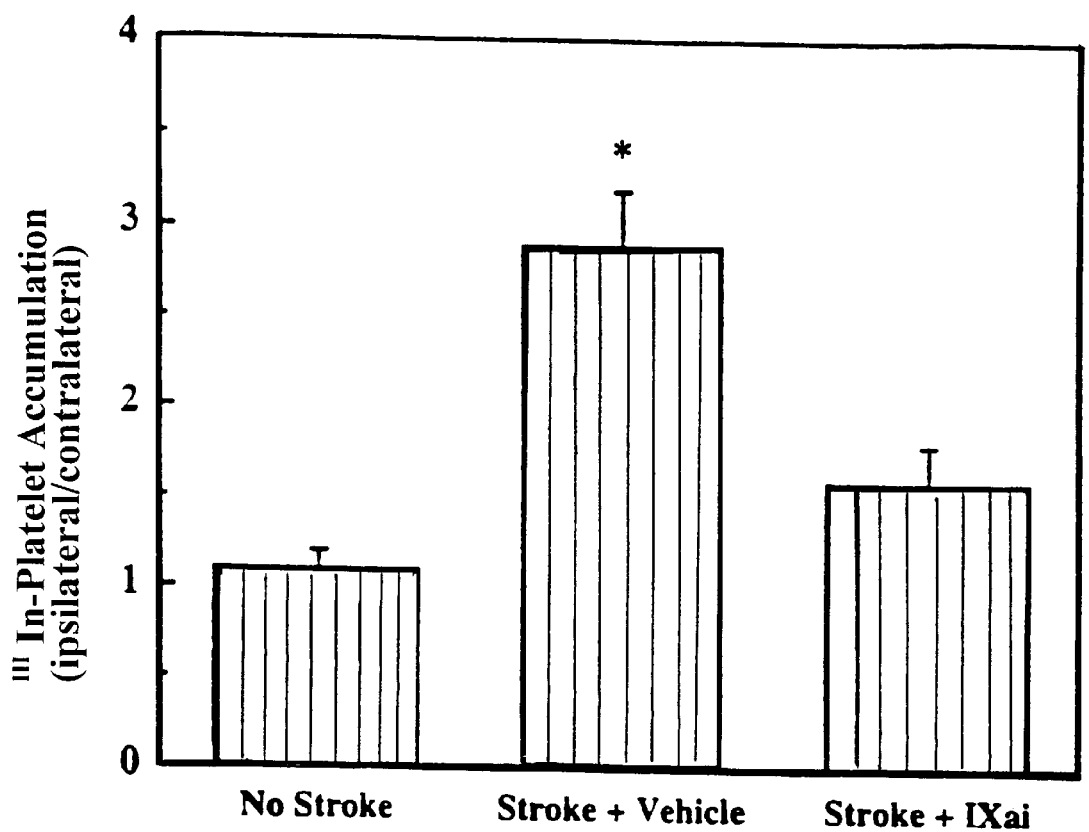

FIG. 11A. Effect of stroke on the accumulation of radiolabeled platelets, and the inhibitory effects of Factor IXai. [111]Indium-platelets were administered to either control animals without stroke (n=4), or to animals immediately prior to stroke treated with vehicle (n=7) or with preoperative administration of Factor IXai (300 μg/kg, n=7). Platelet accumulation is expressed as the ipsilateral cpm/contralateral cpm. Means±SEM are shown. *$p<0.05$ vs No Stroke and vs Stroke+IXai.

Figure 11B:
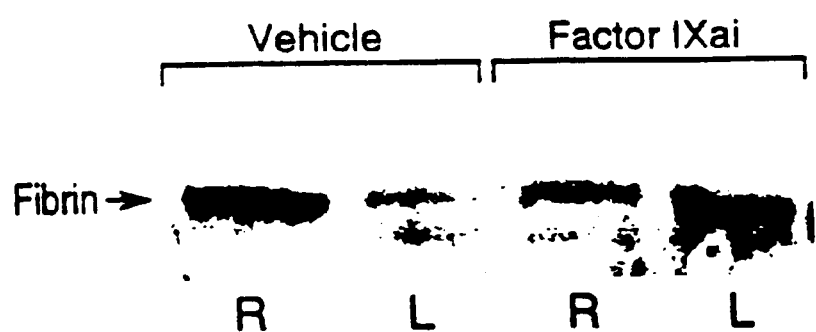

FIG. 11B. Accumulation of fibrin in infarcted cerebral tissue. After 45 minutes of right middle cerebral artery occlusion and 23 hours of reperfusion, brains were harvested from representative mice which had been treated prior to surgery with either vehicle (leftmost two lanes) or Factor IXai (300 μg/kg, rightmost two lanes). The brains were divided into ipsilateral (R) and contralateral (L) hemispheres, and plasmin digestion performed to solubilize accumulated fibrin. Immunoblotting was performed using a primary antibody directed against a neoepitope expressed on the gamma—gamma chain dimer of crosslinked fibrin.

Figure 11C:
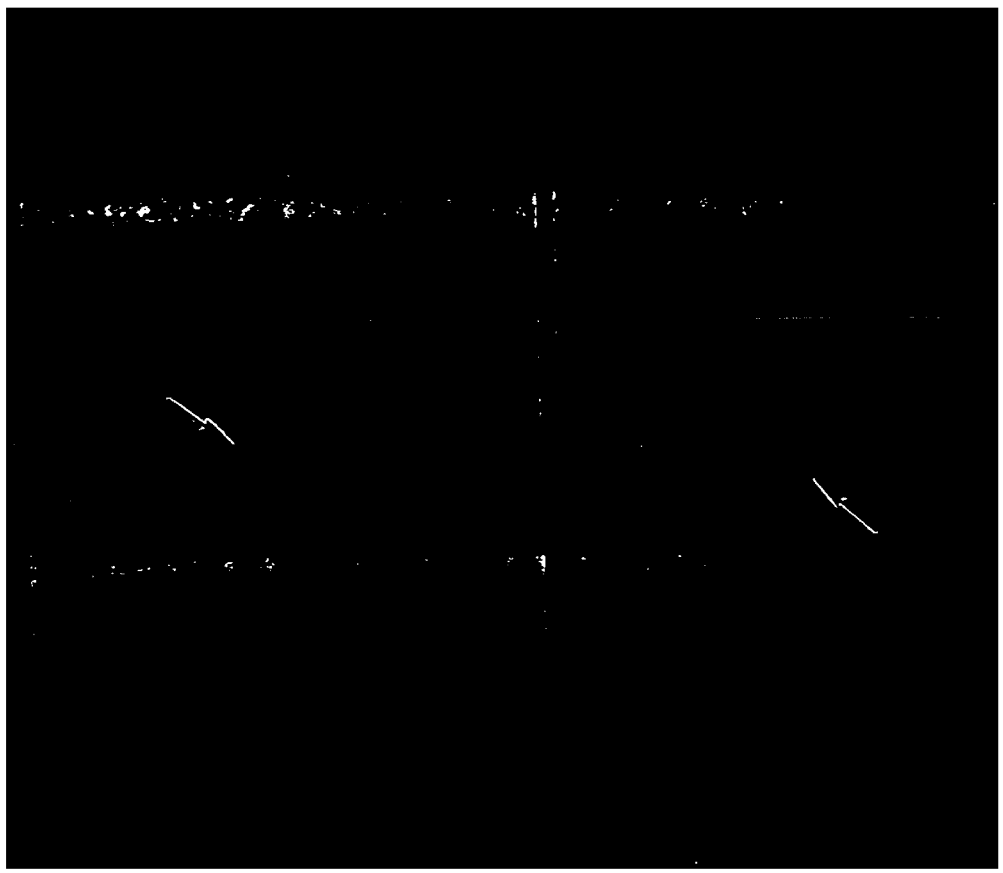

FIG. 11C. Immunohistochemical identification of sites of fibrin formation in stroke. Using the same procedures as described in FIG. 1b, brains were harvested at 24 hours, formalin fixed/paraffin embedded, and fibrin was detected immunohistochemically using the primary antibody used for immunoblotting (FIG. 11B). Arrows identify cerebral microvessels, with fibrin (red staining) observed in the in the ipsilateral microvasculature (right panel), but not in the contralateral (nonischemic, left panel) microvasculature.

Figure 11D:
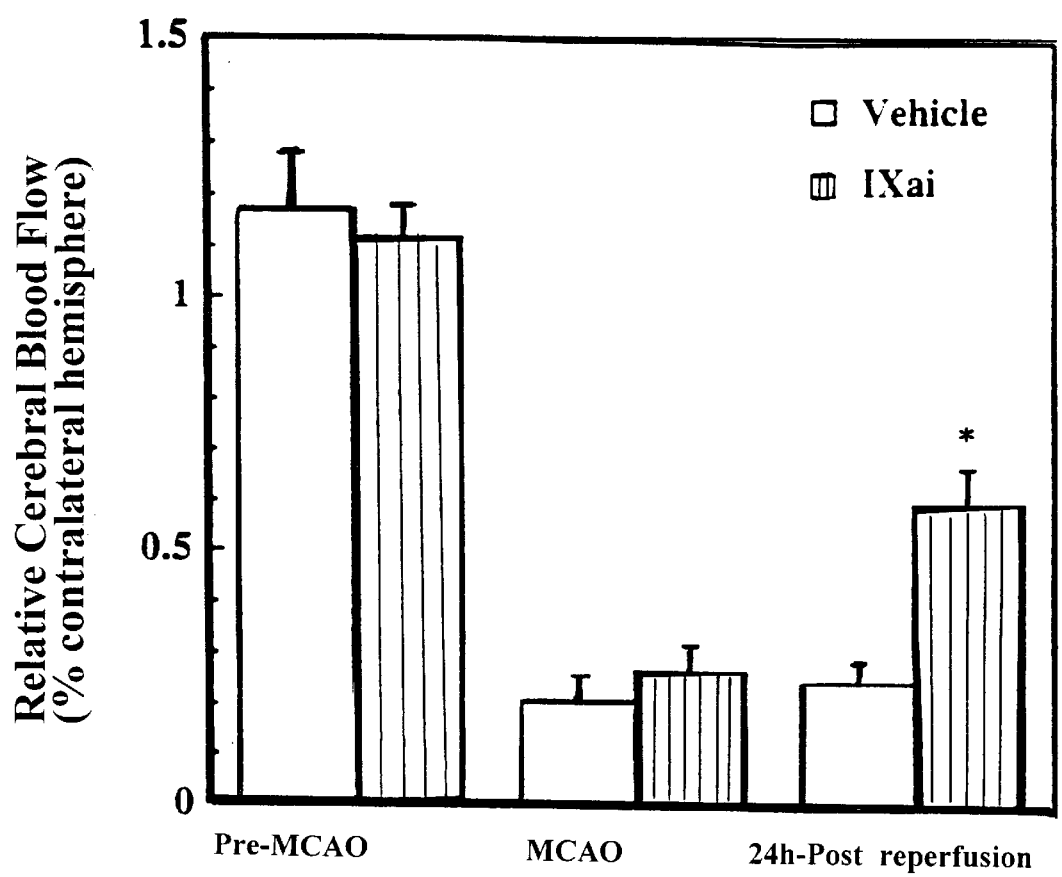

FIG. 11D. Effect of Factor IXai on CBF in a murine stroke model. Serial measurements of relative CBF were made using a laser doppler over precisely defined neuroanatomic landmarks (13), expressed as ipslateral/contralateral CBF; Experiments were performed as described in FIG. 1$b$; n=48 for Factor IXai-treated animals (300 $\mu$g/kg); n=62 for vehicle-treated animals subjected to identical procedures. Means±SEM are shown. *$p<0.05$.

Figure 12:
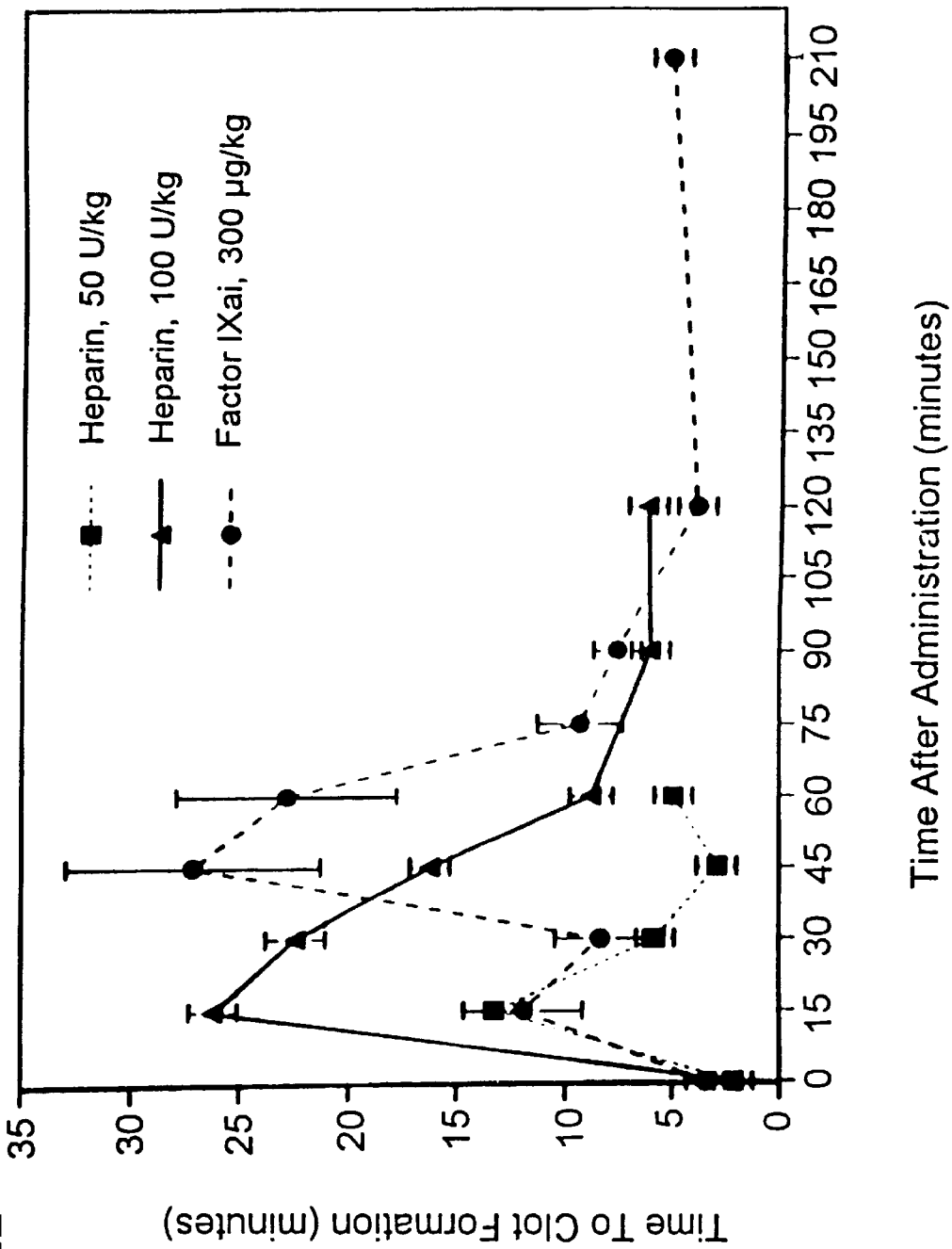

FIG. 12. Modified cephalin clotting time to examine the antithrombotic effects of intravenous Factor IXai and heparin. Factor IXai (300 $\mu$g/kg, n=5) or heparin (50 U/kg, n=4, or 100 U/kg, n=3) was administered to mice as an intravenous single bolus, plasma obtained, and the time to clot formation measured in an in vitro reaction in which the activity of Factor IXa is rate-limiting.

Figure 13A:
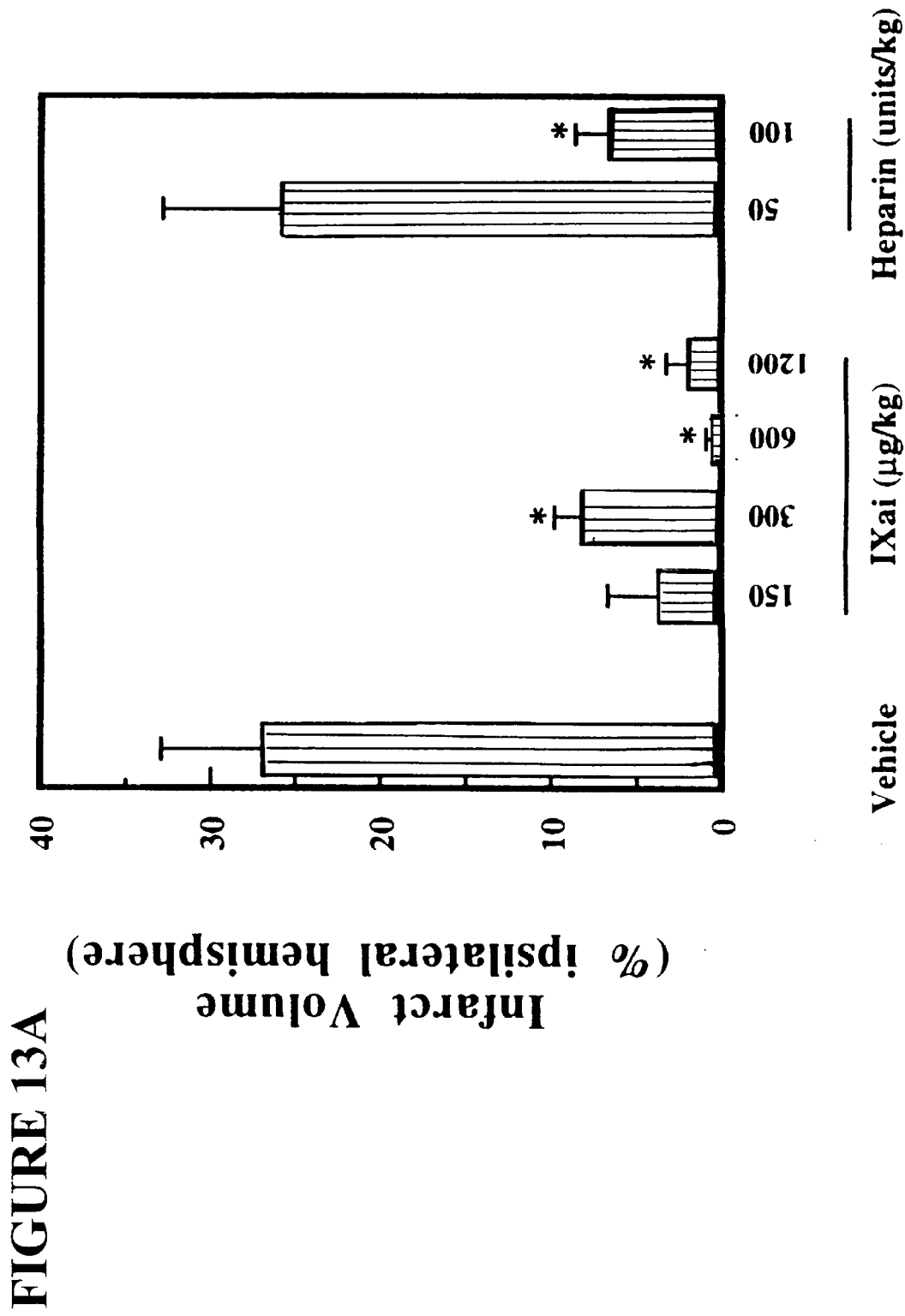
Figure 13B:
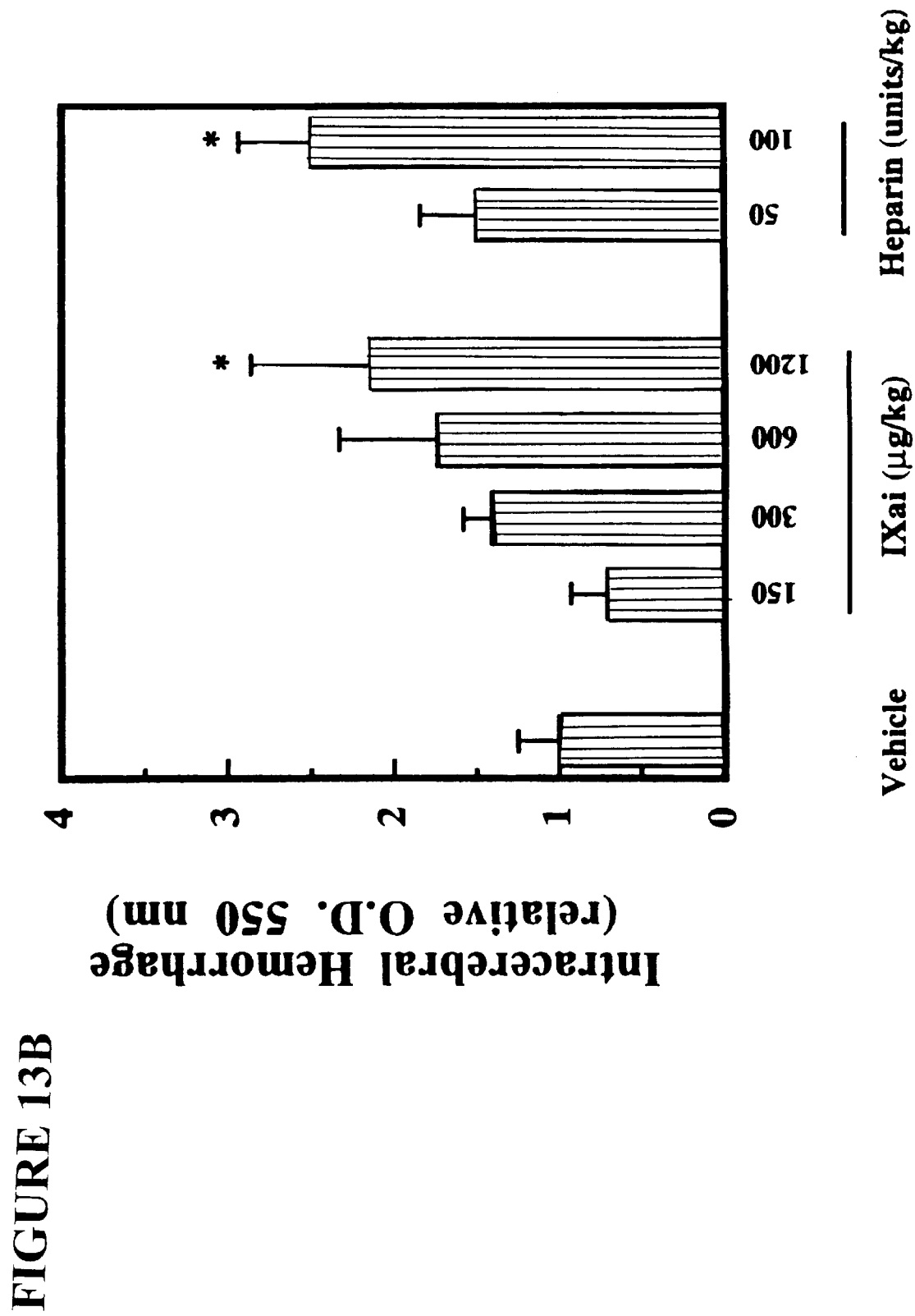
Figure 13C:
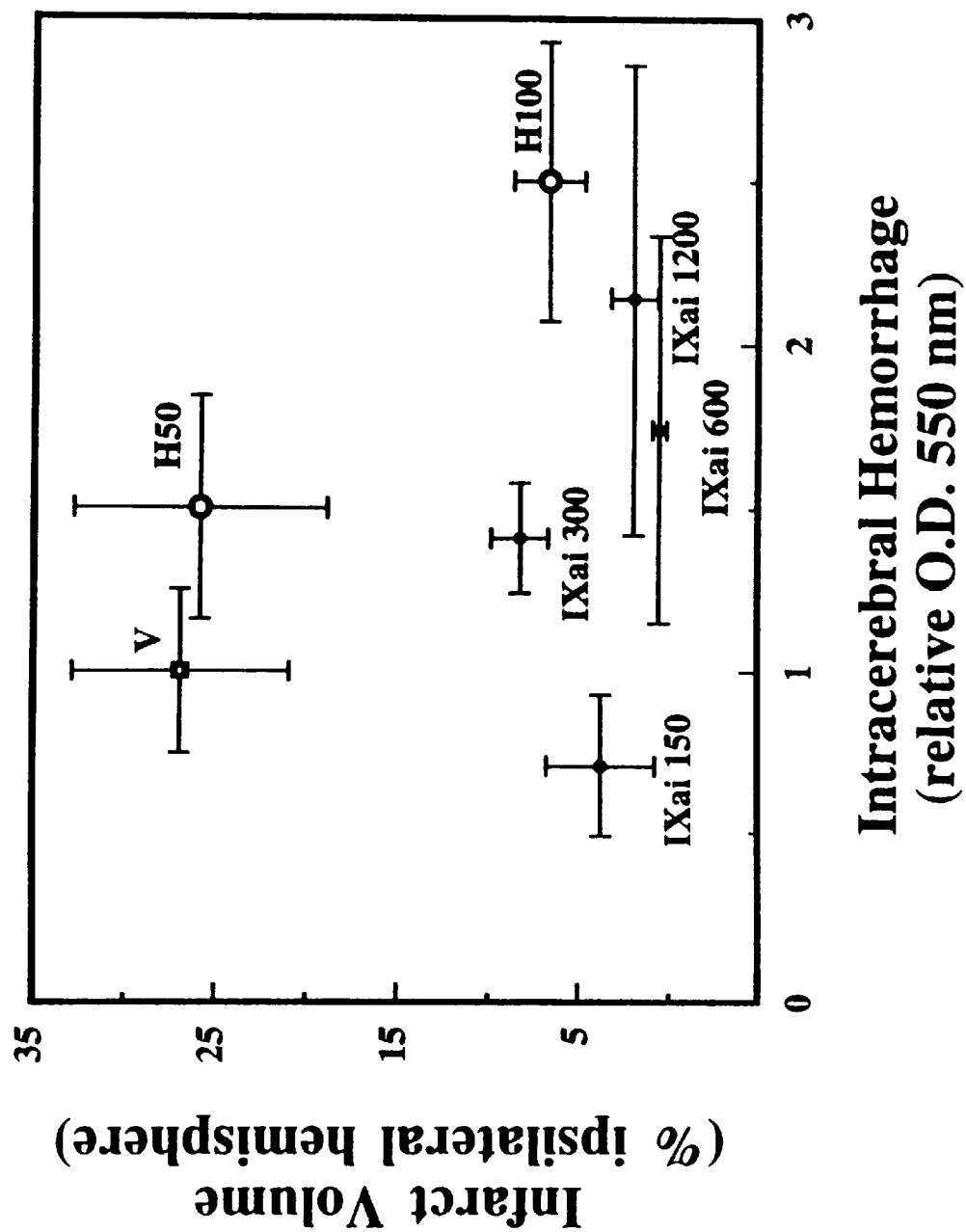

FIGS. 13A–13C. Effect of Factor IXai on infarct volume an intracerebral hemorrhage in a murine stroke model.

FIG. 13A. Effect of Factor IXai on cerebral infarct volumes, measured by TTC staining of serial coronal sections of brain. Prior to stroke, animals were given either vehicle (n=62), Factor IXai at 150 $\mu$g/kg (n=5), 300 $\mu$g/kg (n=48), 600 $\mu$g/kg (n=6), or 1200 $\mu$g/kg (n=6), or heparin at 50 U/kg (n=14) or 100 U/kg (n=15). Means±SEM are shown. *$p<0.05$ vs vehicle-treated animals.

FIG. 13B. Effect of Factor IXai on intracerebral hemorrhage 24 hours after stroke, as measured by a quantitative spectrophotometric hemoglobin assay (17, see references following Example 4), in which O.D. at 550 nm is linearly related to brain hemoglobin content. Relative O.D. was determined as the ratio of the O.D. of a given experiemtnal condition relative to the mean O.D. of vehicle-treated animals. Prior to stroke, animals were given either vehicle (n=9), Factor IXai at 150 $\mu$g/kg (n=4), 300 $\mu$g/kg (n=9), 600 $\mu$g/kg (n=3), or 1200 $\mu$g/kg (n=3), or heparin at 50 U/kg (n=5) or 100 U/kg (n=11). Means±SEM are shown. *$p<0.05$ vs vehicle-treated animals.

FIG. 13C. Infarct volume/ICH plot of data shown in FIGS. 13A and 13B. Infarct volumes were plotted against intracerebral hemorrhage to display the how a given agent: at a given dose effects both infarct volume and ICH simultaneously. V=vehicle, H=heparin, and IXai=Factor IXai; doses are shown. Significant values are shown in FIGS. 13A and 13B, but are omitted here for clarity.

Figure 14:
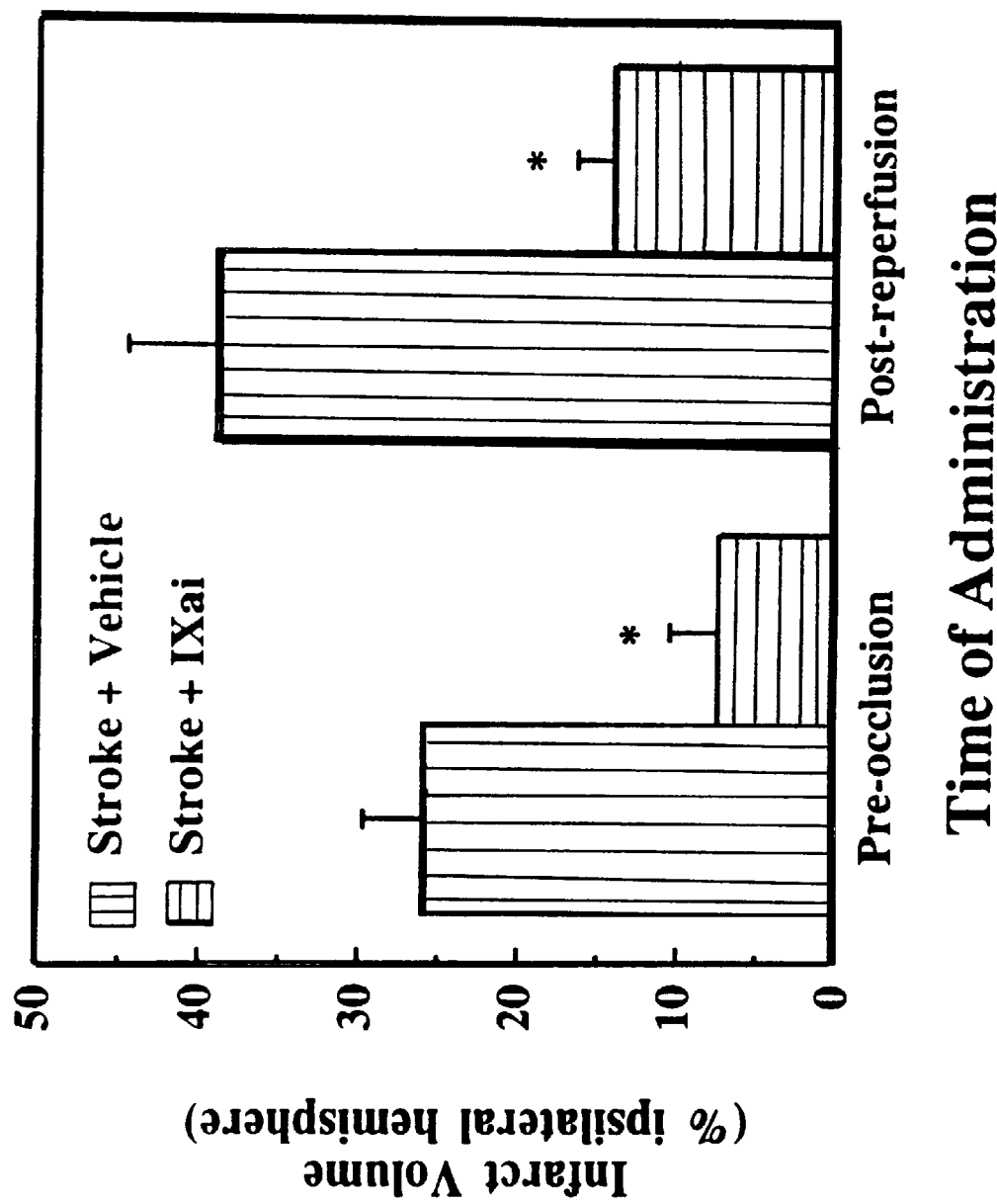

FIG. 14. Effect of timing of Factor IXai administration on cerebral infarct volumes. Mice were either pretreated with intravenous vehicle (n=62) or Factor IXai (300 $\mu$g/kg, n=48) prior to focal cerebral ischemia and reperfusion, or immediately upon withdrawal of the intraluminal middle cerebral arterial occluding suture (n=13 for vehicle, n=7 for Factor IXai). Cerebral infarct volumes were determined from TTC-stained serial cerebral sections. Means±SEM are shown. *$p<0.05$ vs similarly vehicle-treated animals. (The preocclusion administration data is the same data that is shown in FIG. 13A for the 300 $\mu$g/kg dose, but is repeated here to facilitate comparison with the postreperfusion data.

Figure 15A:
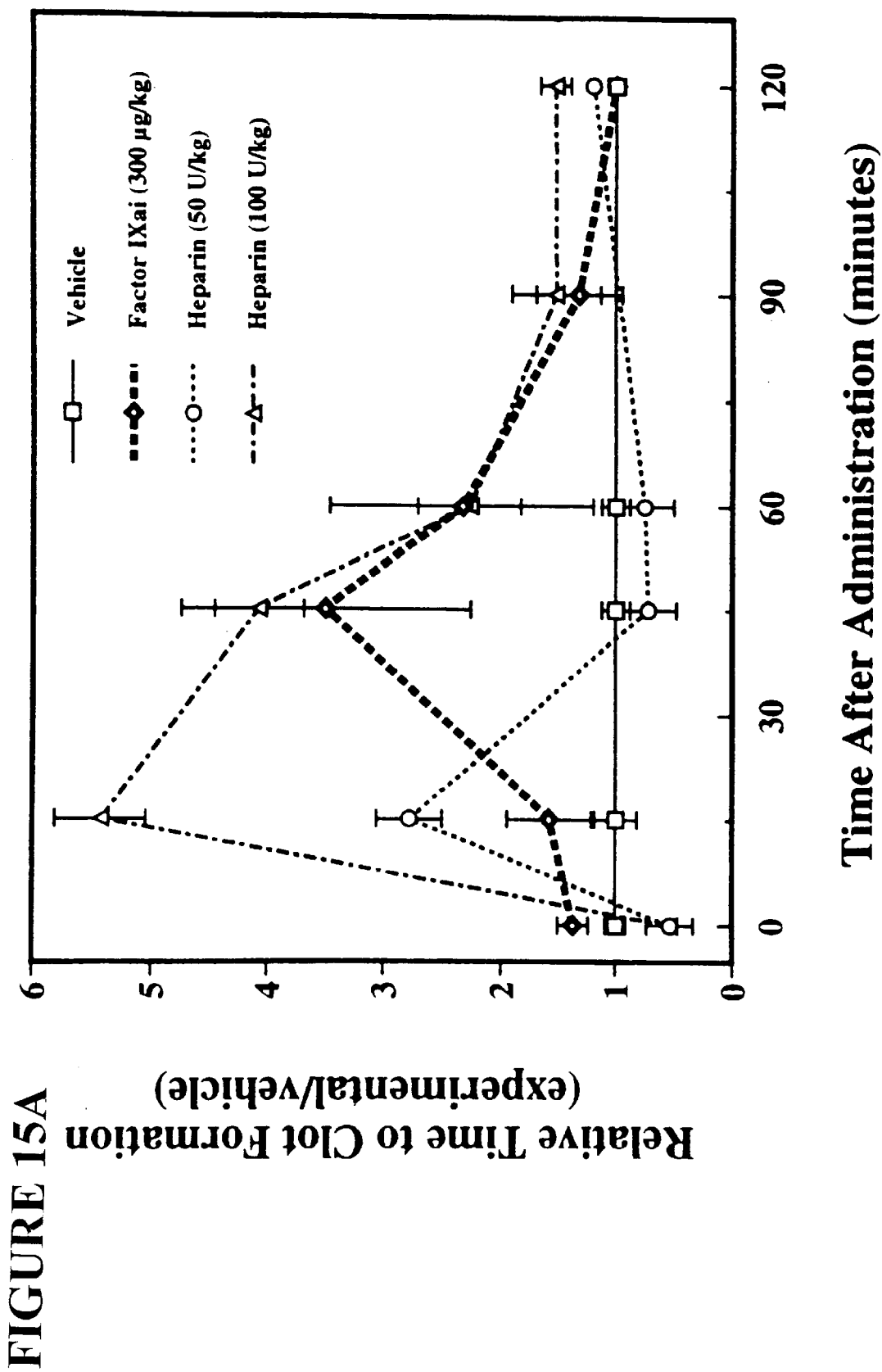
Figure 15B:
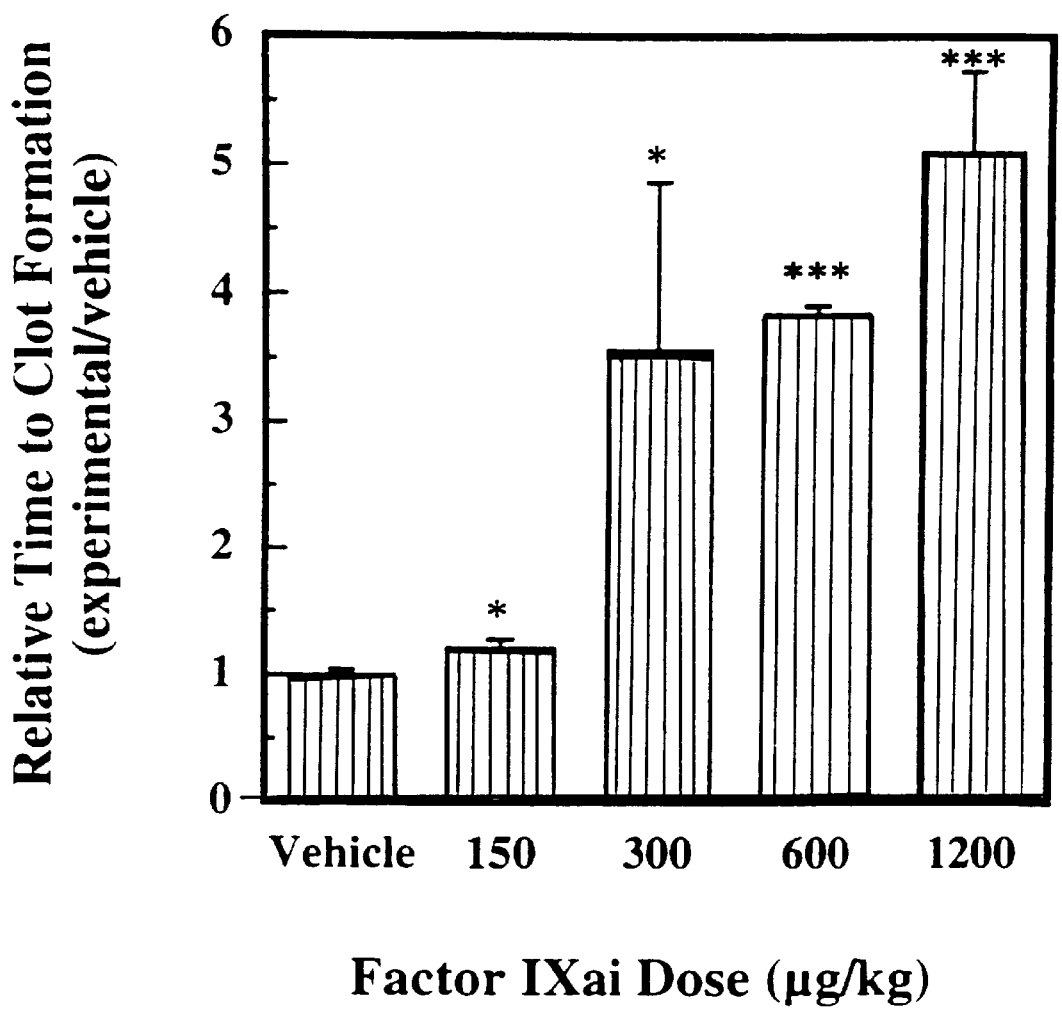

FIGS. 15A–15B. Modified cephalin clotting time assay.

FIG. 15A. The effects of heparin and Factor IXai were compared. These agents (at the indicated doses) were given intravenously to mice, and blood sampled at the indicated time points. Relative time to clot formation using the modified cephalin clotting time assay was determined.

FIG. 15B. The effect of the indicated doses on clotting time of blood samples taken at 45 minutes after the intravenous administration of the indicated dose of vehicle or Factor IXai.

DETAILED DESCRIPTION OF THE INVENTION

The present invention provides a method for treating an ischemic disorder in a subject which comprises administering to the subject a pharmaceutically acceptable form of a Factor IXa compound in a sufficient amount over a sufficient period of time to inhibit coagulation so as to treat the ischemic disorder in the subject.

The present invention also provides a method for treating an ischemic disorder in a subject which comprises administering to the subject a pharmaceutically acceptable form of a Factor IXa compound in a sufficient amount over a sufficient period of time to inhibit coagulation so as to treat the ischemic disorder in the subject.

The present invention provides a method for treating an ischemic disorder in a subject which comprises administering to the subject a pharmaceutically acceptable form of a Factor IXa compound and a pharmaceutically acceptable form of an indirect or direct fibrinolytic agent, each in a sufficient amount over a sufficient period of time to inhibit coagulation so as to treat the ischemic disorder in the subject.

In another embodiment, the ischemic disorder comprises a peripheral vascular disorder, a pulmonary embolus, a venous thrombosis, a myocardial infarction, a transient ischemic attack, unstable angina, a reversible ischemic neurological deficit, sickle cell anemia or a stroke disorder.

In another embodiment, the ischemic disorder is iatogenically induced. In another embodiment, the subject is undergoing angioplasty, heart surgery, lung surgery, spinal surgery, brain surgery, vascular surgery, abdominal surgery, or organ transplantation surgery. In another embodiment, the organ transplantation surgery comprises heart, lung, pancreas or liver transplantation surgery.

In another embodiment, the period of time comprises from about 5 days before surgery or onset of the disorder to about 5 days after surgery or the onset of the disorder. In another embodiment, the period of time comprises from about 1 hour before surgery or the onset of the disorder to about 12 hours after surgery or the onset of the disorder. In another embodiment, the period of time comprises from about 12 hours before surgery or the onset of the disorder to about 1 hour after surgery or the onset of the disorder. In another embodiment, the period of time comprises from about 1 hour before surgery or the onset of the disorder to about 1 hour after surgery or the onset of the disorder.

In one embodiment, the subject is a mammal. In another embodiment, the mammal is a human. In another embodiment, the amount comprises from about 75 $\mu$g/kg to about 550 $\mu$g/kg. In another embodiment, the amount comprises 300 $\mu$g/kg.

In one embodiment, the direct fibrinolytic agent comprises plasmin or viper venom. In another embodiment, the indirect fibrinolytic agent comprises tissue plasminogen activator, urokinase, streptokinase, RETROVASE®, or recombinant tissue plasminogen activator.

The present invention also provides for a method for identifying a compound that is capable of improving an ischemic disorder in a subject which comprises: a) administering the compound to an animal, which animal is a stroke animal model; b) measuring stroke outcome in the animal, and c) comparing the stroke outcome in step (b) with that of the stroke animal model in the absence of the compound so as to identify a compound capable of improving an ischemic disorder in a subject. In another embodiment, the compound is a Factor IXa compound.

In one embodiment, the stroke animal model comprises a murine model of focal cerebral ischemia and reperfusion. In another embodiment, the stroke outcome is measured by physical examination, magnetic resonance imaging, laser doppler flowmetry, triphenyl tetrazolium chloride staining, chemical assessment of neurological deficit, computed tomography scan, or cerebral cortical blood flow.

The present invention provides a method for treating a reperfusion injury in a subject which comprises administering to the subject a Factor IXa compound in a sufficient amount over a sufficient period of time to inhibit coagulation so as to treat the reperfusion injury in the subject. In one embodiment, the Factor IXa compound comprises recombinant inactivated Factor IXa. In another embodiment, the Factor IXa compound is a peptide, a peptidomimetic, a nucleic acid, a small molecule, a mutated peptide or nucleic acid, a mutein, an antibody or fragment thereof. In another embodiment, the Factor IXa compound is a synthetic molecule.

The present invention provides for a proteolytically inactive recombinant mutein of Factor IX, which has substantially the same amino acid sequence as normal Factor IX but which has an amino acid substitution for one or more of His221, Asp269 or Ser365. In one embodiment, the mutein has a Ser365 to Ala substitution.

The present invention also provides a proteolytically inactive recombinant mutein of Factor IXa which has substantially the same amino acid sequence as normal human Factor IXa but which has an amino acid substitution for one or more of His41, Asp89 or Ser185 in the heavy chain of Factor IXa. In one embodiment, the mutein. has a Ser185 to Ala substitution.

In another embodiment, an isolated cDNA encodes the mutein. In another embodiment, a replicable vector comprises the cDNA. In another embodiment, a microorganism is transfected with the vector. In another embodiment, an expression vector comprises DNA which encodes the mutein. In another embodiment, a microorganism is transfected with the vector. In one embodiment, the Factor IXa compound comprises the mutein.

The present invention provides a method of inhibiting clot formation in a subject which comprises adding to blood an amount of an inactive recombinant mutein in an amount effective to inhibit clot formation in the subject but which does not significantly interfere with hemostasis when the blood is administered to a patient. In another embodiment, the patient has experienced an ischemic event.

The present invention provides for an assay to monitor the effect of a Factor IXa compound administered to a subject to treat an ischemic disorder in the subject which comprises: a) measuring the ischemic disorder in the subject; b) administering the Factor IXa compound to the subject and measuring the ischemic disorder, and c) comparing the measurement of the ischemic disorder in step (b) with that measured in step (a) so as to monitor the effect of the Factor IXa compound. In one embodiment, the ischemic disorder is measured by physical examination, magnetic resonance imaging, laser doppler flowmetry, triphenyl tetrazolium chloride staining, chemical assessment of neurological deficit, computed tomography scan, or cerebral cortical blood flow.

As used herein, the "ischemic disorder" encompasses and is not limited to a peripheral vascular disorder, a venous thrombosis, a pulmonary embolus, a myocardial infarction, a transient. ischemic attack, lung ischemia, unstable angina, a reversible ischemic neurological deficit, adjunct thromolytic activity, excessive clotting conditions, reperfusion injury, sickle cell anemia, a stroke disorder or an iatrogenically induced ischemic period such as angioplasty.

In one embodiment of the present invention, the subject is undergoing heart surgery, angioplasty, lung surgery, spinal surgery, brain surgery, vascular surgery, abdominal surgery, or organ transplantation surgery. The organ transplantation surgery may include heart, lung, pancreas or liver transplantation surgery.

In the intrinsic pathway, Factor XIa cleaves Factor IX between Arg145 and Ala146 and between Arg 180–Val181, releasing a 35 amino acid peptide and producing Factor IXa having a 145 amino acid light chain (amino acids 1–145) and a 235 amino acid heavy chain (amino acids 181–415) joined by a disulfide bond between cysteine residues at positions 132 and 289. Factor IXa is a serine protease which, when complexed with Factor VIIIa on membrane surfaces, converts Factor X to its active form Factor Xa. The enzyme active site of Factor IXa is located on the heavy chain. Three amino acids in the heavy chain are principally responsible for the catalytic activity, His221, Asp269 and Ser365 (H221, D269 and S365, the catalytic triad). If the amino acids of the heavy chain are numbered from 1 to 235, the catalytic triad is His41, Asp89 and Ser185, and the disulfide bond joining the heavy chain to the light chain is at Cys109 on the heavy chain.

As used herein "a Factor IXa compound" means a compound which inhibits or reduces the conversion of Factor X to Factor Xa by naturally occurring Factor IX. As used herein, a Factor IXa compound may be chosen from one of several subsets. One subset is a chemically modified form of naturally occurring Factor IXa which chemical modification results in the inactivation of Factor IXa (e.g., inactivated Factor IXa, active-site blocked Factor IXa or Factor IXai). Another subset of a Factor IXa compound is any recombinant mutated form of Factor IXa (e.g., a mutein form of Factor IXa, a recombinant Factor IXa with a deletion or Factor IXami). In addition, there are other subsets of a Factor IXa compound which include but are not limited to, for example: (1) nucleic acids, (2) anti-Factor IXa antibodies or fragments thereof, (3) saccharides, (4) ribozymes, (5) small organic molecules, or (6) peptidomimetics.

Thus, a Factor IXa compound may encompass the following: a Glu-Gly-Arg chloromethyl ketone-inactivated human factor IXa, an inactive Christmas factor, a Glu-Aly-Arg chloromethyl ketone-inactivated factor IXa, a glutamyl-glycyl-arginyl-Factor IXa, a dansyl Glu-Gly-Arg chloromethyl ketone-inactivated bovine factor IXa (IXai), a Factor IXai, a competitive inhibitor of Factor IXa, a peptide mimetic of Factor IXa, a carboxylated Christmas factor, a competitive inhibitor of the formation of a Factor IXa/VIIIa/X complex, a des-γ-carboxyl Factor IX, Factor IX lacking a calcium-dependent membrane binding function, inactive Factor IX including only amino acids 1–47, apo-Factor IX including amino acids 1–47, Factor IX Bm Kiryu, a Val-313-to-Asp substitution in the catalytic domain of Factor IX, a Gly-311-to-Glu substitution in the catalytic domain of Factor IX, a Gly-311 to Arg-318 deletion mutant of Factor IX, an anti-Factor IXa antibody, an anti-Factor IXa monoclonal or polyclonal antibody. The Factor IXa compound may also include inactive species of Factor IX described in the references provided herein, especially Freedman et al., 1995; Furie and Furie, 1995; Miyata et al., 1994 and Wacey et al., 1994. Factor IX or Factor IXa may be obtained from blood.

Thus, a Factor IXa compound may be Factor IXa in which the active site is blocked and may be prepared as described in Experimental Details below. The Factor IXa compound may be a Factor IXa which includes post-translational modifications including glycosylation, β-hydroxylation of aspartic acid, γ-carboxylation of glutamic acid and propeptide cleavage. The Factor IXa compound may be concentrated via heparin affinity chromatography or hydrophobic interaction chromatography. The Factor IXa compound may be a genetically engineered, a recombinant Factor IXa in which amino acids at the active site, especially the serine amino acid at the active site, have been altered to render the recombinant Factor IXa functionally inactive, but still capable of competing with intact, native Factor IXa for cell surface binding. In another embodiment, the Factor IXa compound is a synthetic molecule. In another embodiment, the carrier comprises an aerosol, intravenous, oral or topical carrier.

In one embodiment of the present invention the Factor IXa compound is a form of Factor IXa inactivated by the standard methods known to one of skill in the art, such as mutation of the gene which encodes Factor IXa.

As used herein an "indirect fibrinolytic agent" is an agent whose activity indirectly results in fibrin lysis. In one embodiment, an indirect fibrinolytic agent comprises tissue plasminogen activator (tPA), urokinase, streptokinase, RETROVASE®, or recombinant tissue plasminogen activator. As used herein "direct fibrinolytic agent" is an agent that is capable of fibrinolysis. In one embodiment, a direct fibrinolytic agent is plasmin or viper venom. In one embodiment, the amount of fibrinolytic agent administered to a subject is up to the amount necessary to lyse an intravascular fibrin clot or an amount to cause lysis of a formed intravascular fibrin clot.

One embodiment of the present invention is wherein the Factor IXa compound is inactivated by the standard methods known to one of skill in the art, such as mutation. Factor IXa compound may be an antagonist of Factor IXa. Such antagonist may be a peptide mimetic, a nucleic acid molecule, a ribozyme, a polypeptide, a small molecule, a carbohydrate molecule, a monosaccharide, an oligosaccharide or an antibody.

A preferred embodiment of the present invention is wherein the Factor IXa compound is an active site-blocked Factor IXa or a Glu-Gly-Arg chloromethyl ketone-inactivated human factor IXa. In a preferred embodiment, the effective amount is from about 0.1 μg/ml plasma to about 250 μg/ml plasma or from about 0.5 μg/ml plasma to about 25 μg/ml plasma or preferably from 0.7 μg/ml plasma to about 5 g/ml plasma.

Another embodiment of present invention is where the sufficient amount includes but is not limited to from about 75 μg/kg to about 550 μg/kg. The amount may be 300 μg/kg.

In an embodiment of the present invention the Factor IXa compound is an inactive mutein form of Factor IXa which is useful as selective antithrombotic agent. As used herein, "mutein form" of Factor IXa means a protein which differs from natural factor IXa by the presence of one or more amino acid additions, deletions, or substitutions which reduce or eliminate the ability of the protein to participate in the conversion of Factor X to Factor Xa.

In another embodiment of the present invention the Factor IXa compound is a proteolytically inactive, recombinant mutein form of Factor IX, which has substantially the same amino acid sequence as normal or native human Factor IX but in which a different amino acid has been substituted for one or more of His221, Asp269 and Ser365. The present invention also provides a proteolytically inactive, recombinant mutein form of Factor IXa, which has substantially the same amino acid sequence as normal or native human factor IXa but in which a different amino acid has been substituted for one or more of His41, Asp89 or Ser185 in the heavy chain of Factor IXa. The term "proteolytically inactive" means that the muteins are incapable of converting Factor X to Factor Xa.

The invention also provides a method of inhibiting thrombosis in a human patient which comprises administering to the patient, or adding to the blood which is to be administered to the patient, an amount of an inactive recombinant mutein of this invention which is effective to inhibit thrombosis but which does not significantly interfere with hemostasis in the patient.

Recombinant muteins of Factor IX useful in this invention are referred to collectively as Factor Ixmi (i.e., Factor IX mutationally inactivated). Recombinant muteins of Factor IXa useful in this invention are referred to collectively as Factor IXami. Examples of Factor IXa compounds which are recombinant muteins are as follows:

Factor IXmi (Ser365→Xxx)
Factor IXmi (Asp269→Yyy)
Factor IXmi (His221→Zzz)
Factor IXmi (Ser365→Xxx, Asp269→Yyy)
Factor IXmi (Ser 365→Xxx, His221Zzz)
Factor IXmi (Asp269→Yyy, His→Zzz)
Factor IXmi (Ser365→Xxx, Asp269→Yyy, His→Zzz)
Factor IXami (Ser365→Xxx)
Factor IXami (Asp269→Yyy)
Factor IXami (His221→Zzz)
Factor IXami (Ser365→Xxx, Asp269→Yyy)
Factor IXami (Ser365→Xxx, His221→Zzz)
Factor IXami (Asp269→Yyy, His→Zzz)
Factor IXami (Ser365→Xxx, Asp269→Yyy, His→Zzz)

wherein Xxx is any one of the standard amino acids other than serine, Yyy is any one of the standard amino acids other than aspartic acid, and Zzz is any of the standard amino acids other than histidine. Preferred recombinant muteins are Factor IXmi(Ser365→Ala) and Factor IXami (Ser365→Ala).

Factor IXmi and Factor IXami are functionally similar to Factor IXai in terms of their ability to establish effective anti-coagulation intravascularly and in ex vivo equipment connected to the blood stream while permitting retention of effective hemostasis. The advantages of Factor IXmi and Factor IXami over Factor IXai are the following:

- Factor IXmi and Factor IXami can be produced directly in a genetically engineered organism, thus avoiding several processing and purification steps with their attendant losses, thereby improving yield of product.
- The cost of production of Factor IXmi and Factor IXami in an appropriate genetically engineered organism is lower than the cost of production of Factor IXai from human plasma.
- Factor IXmi and Factor IXami, produced in a genetically engineered organism, will not be subject to the risk cf contamination with various infectious agents such as viruses or prions (for example the agents for HIV disease and for bovine and/or human spongiform encephalopathies).

Factor IXmi and Factor IXami, being less different from wild-type human Factor IX and Factor IXa than is the chemically modified Factor IXai, will have a lower probability of eliciting an immune response in patients who are dosed with the modified protein for extended periods of time, thereby reducing the risk of delayed type hypersensitivity reactions and improving the safety for indications such as anticoagulation in hemodialysis that will require repeated, long-term use.

The recombinant muteins of this invention can be produced by known genetic engineering techniques, using as starting material recombinant cDNA for Factor IX in an appropriate cloning vector. For example, starting materials which may be used in the production of a Factor IXa compound may be the product of Example 5 of U.S. Pat. No. 4,770,9990 which are recombinant plaques of *E. coli* infected with bacteriophage M12mp11 Pst vector containing the entire sequence of recombinant Factor IX cDNA ligated to Pst: adapters. The recombinant plaques are used to prepare single-stranded DNA by either the small-scale or large-scale method described in Sambrook et al., *Molecular Cloning, A Laboratory Manual, Second Edition*, Cold Spring Harbor Press, 1989, pages 4.29–4.30 and 4.32.

The single-stranded M13mp11 containing Factor IX cDNA is then used to carry out oligonucleotide-mediated mutagenesis using the double primer method of Zoller and Smith as described in Sambrook et al., 1989, pages 15.51–15.73. Mutagenic primers which can be used include the following:

1) Oligonucleotides for producing Factor IXmi (Ser365→Xxx)

3'-W ACA GTT CCT CTA XXX CCC CCT GGG GTA V-5' (SEQ ID NO: 1–9)

where

W is T, 3'-GT or 3'-AGT

V is C, 3'-CA, or 3'-CAA

XXX is the complement to a DNA codon for any one of the standard amino acids other than serine.

2) Oligonucleotides for producing FACTOR IXmi (Asp269→Yyy)

3'-W TTC ATG TTA GTA YYY TAA CGC GAA GAC V-5' (SEQ ID NO: 10–18)

where

W IS A, 3'=TA, OR 3'-TTA

V is C, 3'-CT, or 3'-CTT

YYY is the complement to a DNA codon for any one of the standard amino acids other than aspartic acid and cysteine.

3) Oligonucleotides for producing Factor IXmi (His221Zzz)

3'-TTA CAT TGA CGA CGG ZZZ ACA CAA CTT TGA CCA-5' (SEQ ID NO: 19)

where

W is A, 3'-AA, or 3'-TAA

V is C, 3'-CC, or 3'-CCA

ZZZ is the complement to a DNA codon for any one of the standard amino acids other than histidine and cysteine.

Oligonucleotide primers for producing the preferred Factor IXmi of this invention, Factor IXmi(Ser365→Ala), are those of No. 1 above, wherein XXX is the complement of a codon for alanine, i.e., 3'-CGA, 3'-CGC, 3'-CGT or 3'-CGC. A specific primer for producing Factor IXmi (Ser365→Ala) is:

3'-GT ACA GTT CCT CTA CGA CCC CCT GGG GTA C-5' (SEQ ID NO: 20)

A skilled artisan would recognize and know how to carry out the remaining steps of oligonucleotide-mediated mutagenesis as follows:

Hybridization of mutagenic oligonucleotides to the target DNA.

Extension of the hybridized oligonucleotides to the target DNA.

Transfection of susceptible bacteria.

Screening of plaques for the desired mutation.

Preparation of single-stranded DNA from a mutant plaque.

Sequencing the single-stranded DNA.

Recovery of double-stranded Factor IXmi cDNA.

Inserting the double-stranded Factor IXmi cDNA into the expression vector used by Kaufman (for example).

Expression of Factor IXmi.

Treating the Factor IXmi with Factor XIa to produce Factor IXami.

Another embodiment of the present invention wherein the Factor IXa compound is capable of inhibiting the active site of Factor IXa. Such a compound is obtainable from the methods described herein. The Factor IXa compound may be a peptide, a peptidomimetic, a nucleic acid or a small molecule. The agent may be an antibody or portion thereof. The antibody may be a monoclonal antibody or a polyclonal antibody. The portion of the antibody may include a Fab.

One embodiment of the present invention is wherein the Factor IXa compound is a peptidomimetic having the biological activity of a Factor IXa or a Glu-Gly-Arg chloromethyl ketone-inactivated human Factor IXa wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods. The present invention provides for peptidomimetic compounds which have substantially the same three-dimensional structure as those compounds described herein.

In addition to the compounds disclosed herein having naturally-occurring amino acids with peptide or unnatural linkages, the present invention also provides for other structurally similar compounds such as polypeptide analogs with unnatural amino acids in the compound. Such compounds may be readily synthesized on a peptide synthesizer available from vendors such as Applied Biosystems, Dupont and Millipore.

Another embodiment of the present invention is a pharmaceutical composition which may include an effective amount of a Factor IXa compound and a pharmaceutically acceptable carrier. The carrier may include a diluent. Further, the carrier may include an appropriate adjuvant, a herpes virus, an attenuated virus, a liposome, a microencapsule, a polymer encapsulated cell or a retroviral vector. The carrier may include an aerosol, intravenous, oral or topical carrier.

The present invention provides for a method for identifying a compound that is capable of improving an ischemic disorder in a subject which includes: a) administering the compound to an animal, which animal is a stroke animal model; b) measuring stroke outcome in the animal, and c) comparing the stroke outcome in step (b) with that of the stroke animal model in the absence of the compound so as to identify a compound capable of improving an ischemic disorder in a subject. The stroke animal model includes a murine model of focal cerebral ischemia and reperfusion. The stroke outcome may be measured by physical examination, magnetic resonance imaging, laser doppler flowmetry, triphenyl tetrazolium chloride staining, clinical assessment of neurological deficit, computed tomography scan, or cerebral cortical blood flow. The stroke outcome in a human may be measured also by clinical measurements, quality of life scores and neuropsychometric testing.

The present invention provides for treatment of ischemic disorders by inhibiting the ability of the neutrophil, monocyte or other white blood cell to adhere properly. This may be accomplished removing the counter ligand, such as CD18. It has been demonstrated as discussed hereinbelow, that "knock-out" CD18 mice (mice that do not have expression of the normal CD18 gene) are protected from adverse ischemic conditions. The endothelial cells on the surface of the vessels in the subject may also be a target for treatment. In a mouse model of stroke, administration of TPA as a thrombolytic agent caused some visible hemorrhaging along with improvement of the stroke disorder. The present invention may be used in conjunction with a thrombolytic therapy to increase efficacy of such therapy or to enable lower doses of such therapy to be administered to the subject so as to reduce side effects of the thrombolytic therapy.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds capable of treating ischemic disorder or improving stroke outcome in the subject of the invention together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of alleviating the symptoms of the stroke disorder or improving the stroke outcome in the subject. Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with 125I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

By means of well-known techniques such as titration and by taking into account the observed pharmacokinetic characteristics of the agent in the individual subject, one of skill in the art can determine an appropriate dosing regimen. See, for example, Benet, et al., "Clinical Pharmacokinetics" in ch. 1 (pp. 20–32) of Goodman and Gilman's The Pharmacological Basis of Therapeutics, 8th edition, A. G. Gilman, et al. eds. (Pergamon, New York 1990).

The present invention provides for a pharmaceutical composition which comprises an agent capable of treating an ischemic disorder or improving stroke outcome and a pharmaceutically acceptable carrier. The carrier may include but is not limited to a diluent, an aerosol, a topical carrier, an aqueous solution, a nonaqueous solution or a solid carrier.

This invention is illustrated in the Experimental Detail section which follows. These sections are set forth to aid in an understanding of the invention but are not intended to, and should not be construed to, limit in any way the invention as set forth in the claims which follow thereafter.

Experimental Details
Abbreviations:

EC, endothelial cell; PMN, polymorphonuclear leukocyte; WP, Weibel-Palade body; vWF, von Willebrand factor; EGTA, ethyleneglycol bis (aminoethylether) tetraacetic acid; HBSS, Hank's balanced salt solution; CS, coronary sinus; IL, interleukin; PAF, platelet activating factor; HUVEC, human umbilical vein EC; LR, lactated Ringer's solution; MCAO, middle cerebral artery occlusion; rt-PA, recombinant tissue plasminogen activator; ICH, intracerebral hemorrhage; OD, optical density; MCA, middle cerebral artery; rt-PA, recombinant tissue-type plasminogen activator; TIA, transient ischemic attack; TTC, triphenyltetrazolium chloride.

EXAMPLE 1

Procedural and Strain-Related Variables Significantly Effect Outcome in a Murine Model of Focal Cerebral Ischemia The recent availability of transgenic mice has led to a burgeoning number of reports describing the effects of specific gene products on the pathophysiology of stroke. Although focal cerebral ischemia models in rats have been well-described, descriptions of a murine model of middle cerebral artery occlusion are scant, and sources of potential experimental variability remain undefined. It was hypothesized that slight technical modifications would result in widely discrepant results in a murine model of stroke, and that controlling surgical and procedural conditions could lead to reproducible physiologic and anatomic stroke outcomes. To test this hypothesis, a murine model was established which would permit either permanent or transient focal cerebral ischemia by intraluminal occlusion of the middle cerebral artery (MCA). This study provides a detailed description of the surgical technique, and reveals important differences between strains commonly used in the production of transgenic mice. In addition to strain-related differences, infarct volume, neurologic outcome, and cerebral blood flow appear to be importantly affected by temperature during the ischemic and post-ischemic periods, mouse size, and size of the suture which obstructs the vascular lumen. When these variables were kept constant, there was remarkable uniformity of stroke outcome. These data emphasize the protective effects of hypothermia in stroke, and should help to standardize techniques among different laboratories to provide a cohesive framework for evaluating the results of future studies in transgenic animals.

Introduction:

The recent advent of genetically altered mice provides a unique opportunity to evaluate the role of single gene products in the pathophysiology of stroke. Although there is an increasing number of reports about the effect of cerebral ischemia in transgenic mice, to date, there exists no detailed description of the murine models involved, nor is there a detailed analysis of potentially important procedural variables which may effect stroke outcome. Most descriptions of a murine model (1,4,8,9,14,17–19,23,24; see references listed at end of Example 1) are devolved descriptions of the widely used rat models of focal cerebral ischemia (22,26). Although there has been some attention paid to strain related differences in the susceptibility of mice to cerebral ischemia (4), few technical considerations have been addressed in published studies. Because pilot data demonstrated that minor differences in operative procedure or postoperative care translated into major differences in stroke outcome, the current study was undertaken to systematically identify important surgical, technical, and anatomic considerations required to obtain consistent results in a murine model of focal cerebral ischemia. When strokes are created in a rigidly controlled manner, differences, due to the absence (or overexpression) of a single gene product, should be readily discernable.

This study presents a detailed rendering of a reproducible murine model of focal cerebral infarction based on modifications of the original rat model (26). This study identifies procedural variables that have a large impact on stroke outcome which have not been previously reported in technical descriptions of murine stroke models. These variables include suture length and gauge, methods of vascular control, temperature regulation in mice, and differences between strains commonly used in the breeding of transgenic animals. As the model described lends itself to the study of either permanent or transient focal cerebral ischemia, evidence is presented that with carefully chosen ischemia times, infarct volume and mortality in reperfused animals can be made to approximate those seen with permanent occlusion. Understanding potential model-dependent sources of variability in stroke outcome can help to clarify divergent results between different laboratories. Adoption of a standardized model which yields consistent results is an important first step towards the use of transgenic mice in the study of the pathophysiology of stroke.

Materials and Methods:

Animal Purchase and Anesthesia: Male mice of three different strains (C57 BlackJ6, CD-1 and 129J) were purchased from Jackson Laboratories (Bar Harbor, Me.). Animals were eight to ten weeks of age and weighed between 18–37 grams (as indicated) at the time of experiments. Mice were anesthetized with an intraperitoneal injection of 0.3 ml of ketamine (10 mg/cc) and xylazine (0.5 mg/cc). An additional dose of 0.1 cc was given prior to withdrawal of the catheter in animals undergoing transient ischemia. On the day following surgery, anesthesia was repeated immediately prior to laser doppler flow measurement and humane euthansia. These procedures have been approved by the Institutional Animal Care and Use Committee at Columbia University, and are in accordance with AALAC guidelines for the humane care and use of laboratory animals.

Figure 1A:
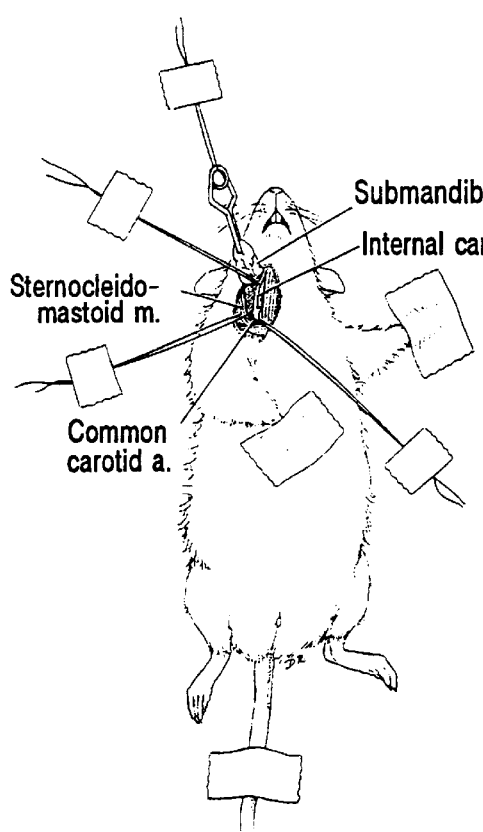
FIGS. 1A, 1B, 1C and 1D. Overview of operative setup for murine focal cerebral ischemia model.
Figure 1B:
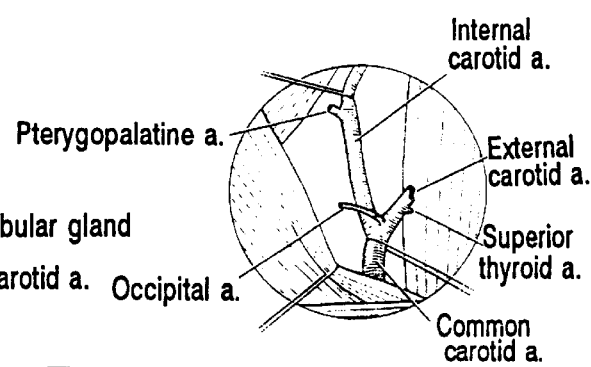

Surgical Set-up:

The animal was positioned supine on a gauze pad which rests on a temperature controlled operating surface (Yellow Springs Instruments, Inc.[YSI], Yellow Springs, Ohio). A rectal temperature probe (YSI) was inserted, in order to regulate the temperature of the operating surface to maintain a constant animal core temperature of 36–38° C. To facilitate exposure, the right hindpaw and left forepaw were taped to the operating surface, the right forepaw was taped to the animal's chest, and the tail was taped to the rectal probe (FIG. 1A). A midline neck incision was made by gently lifting the loose skin between the manubrium and the jaw and excising a 1 $cm^2$ circle of skin. The paired midline submandibular glands directly underlying this area were bluntly divided, with the left gland left in situ. The right gland was retracted cranially with an small straight Sugita aneurysm clip (Mizutto America, Inc., Beverly, Mass) secured to the table by a 4.0 silk and tape. The sternocleidomastoid muscle was then identified, and a 4.0 silk ligature placed around its belly. This ligature was drawn inferolaterally, and taped to the table, to expose the omohyoid muscle covering the carotid sheath. The exposure is shown in FIG. 1B.

Operative Approach:

Once the carotid sheath was exposed, the mouse and the temperature control surface were placed under an operating microscope (16–25×zoom, Zeiss, Thornwood, N.Y.), with a coaxial light source used to illuminate the field. Under magnification, the omohyoid muscle was carefully divided with pickups. The common carotid artery (CCA) was carefully freed from its sheath, taking care not to apply tension to the vagus nerve (which runs lateral to the CCA). Once freed, the CCA was isolated with a 4.0 silk, taped loosely to the operating table. Once proximal control of the CCA was obtained, the carotid bifurcation was placed in view. The occipital artery, which arises from the proximal external carotid artery and courses postero-laterally across the proximal internal carotid artery (ICA) to enter the digastric muscle, was isolated at its origin, and divided using a Malis bipolar microcoagulator (Codman-Schurtleff, Randolph, Mass.). This enabled better visualization of the ICA as it courses posteriorly and cephalad underneath the stylohyoid muscle towards the skull base. Just before the ICA enters the skull it gives off a pterygopalatine branch, which courses laterally and cranially. This branch was identified, isolated, and divided at its origin, during which time the CCA-ICA axis straightens. A 4.0 silk suture was then placed around the internal carotid artery for distal control, the end of which was loosely taped to the operating surface.

Next, the external carotid artery was placed in view. Its cranio-medial course was skeletonized and its first branch, the superior thyroid artery, was cauterized and divided. Skeletonization was subsequently carried out distally by elevation of the hyoid bone to expose the artery's bifurcation into the lingual and maxillary arteries. Just proximal to this bifurcation the external carotid was cauterized and divided. Sufficient tension was then applied to the silk sutures surrounding the proximal common, and distal internal, carotid arteries to occlude blood flow, with care taken not to traumatize the arterial wall. Tape on the occluding sutures was readjusted to maintain occlusion.

Figure 1D:
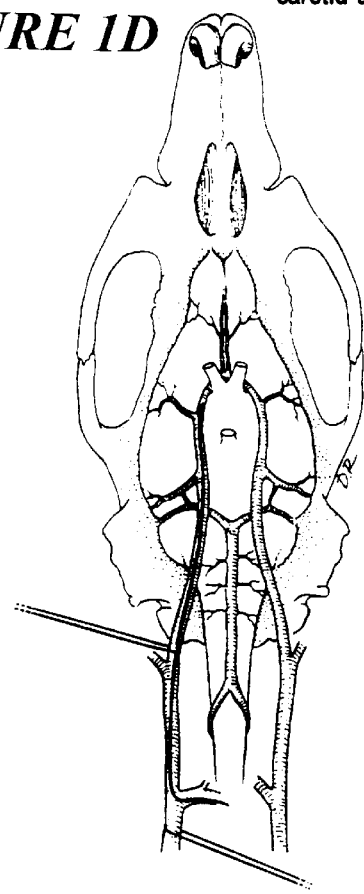
Figure 1C:
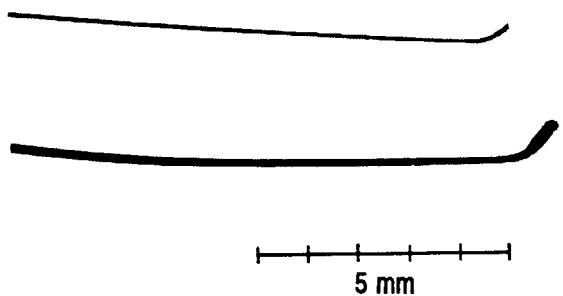

Introduction and Threading of the Occluding Intraluminal Suture:

Immediately following carotid occlusion, an arteriotomy was fashioned in the distal external carotid wall just proximal to the cauterized area. Through this arteriotomy, a heat-blunted 5.0 or 6.0 nylon suture (as indicated in the Results section) was introduced (FIGS. 1C and 1D). As the suture was advanced to the level of the carotid bifurcation, the external stump was gently retracted caudally directing the tip of the suture into the proximal ICA. Once the occluding suture entered the ICA, tension on the proximal and distal control sutures was relaxed, and the occluding suture was slowly advanced up the ICA towards the skull base under direct visualization (beyond the level of the skull base, sight of the occluding suture is lost). Localization of the distal tip of the occluding suture across the origin of the middle cerebral artery (MCA) (proximal to the origin of the anterior cerebral artery) was determined by the length of suture chosen (12 mm or 13 mm as indicated in the Results section, shown in FIG. 1C), by laser doppler flowmetry (see Ancillary physiological procedures section), and by post-sacrifice staining of the cerbral vasculature (see below). After placement of the occluding suture was complete, the external carotid artery stump was cauterized to prevent bleeding through the arteriotomy once arterial flow was reestablished.

Completion of Surgical Procedure:

For all of the experiments shown, the duration of carotid occlusion was less than two minutes. To close the incision, the sutures surrounding the proximal and distal CCA, as well as the sternocleidomastoid muscle, were cut and withdrawn. The aneurysm clip was removed from the submandibular gland and the gland was laid over the operative field. The skin edges were then approximated with one surgical staple and the animal removed from the table.

Removal of the Occluding Suture to Establish Transient Cerebral Ischemia:

Transient cerebral ischemia experiments required reexploration of the wound to remove the occluding suture. For these experiments, initial wound closure was performed with a temporary aneurysm clip rather than a surgical staple to provide quick access to the carotid. Proximal control with a 4-0 silk suture was reestablished prior to removal of the occluding suture to minimize bleeding from the external carotid stump. During removal of the occluding suture, cautery of the external carotid artery stump was begun early, before the distal suture has completely cleared the stump. Once the suture was completely removed, the stump is more extensively cauterized. Reestablishment of flow in the extracranial internal carotid artery was confirmed visually and the wound was closed as for permanent focal ischemia described above. Confirmation of intracranial reperfusion was accomplished with laser doppler flowmetry (see Ancillary physiological procedures section).

Calculation of Stroke Volume:

Twenty-four hours after middle cerebral artery occlusion, surviving mice were reanesthetized with 0.3 cc of ketamine (10 mg/ml) and xylazine (0.5 mg/ml). After final weights, temperatures and cerebral blood flow readings were taken (as described below), animals were perfused with 5 ml of a 0.15% solution of methylene blue and saline to enhance visualization of the cerebral arteries. Animals were then decapitated, and the brains were removed. Brains were then inspected for evidence of correct catheter placement, as evidenced by negative staining of the vascular territory subtended by the MCA, and placed in a mouse brain matrix (Activational Systems Inc., Warren, Minn.) for 1 mm sectioning. Sections were immersed in 2% 2,3,5-triphenyltetrazolium chloride (TTC) in 0.9% phosphate-buffered saline, incubated for 30 minutes at 37° C., and placed in 10 formalin (5). After TTC staining, infarcted brain was visualized as an area of unstained (white) tissue in a surrounding background of viable (brick red) tissue. Serial sections were photographed and projected on tracing paper at a uniform magnification; all serial sections were traced, cut out, and the paper weighed by a technician blinded to the experimental conditions. Under these conditions, infarct volumes are proportional to the summed weights of the papers circumscribing the infarcted region, and were expressed as a percentage of the right hemispheric volume. These methods have been validated in previous studies (3,12,15,16).

Ancillary Physiological Studies:

Ancillary physiogical studies were performed on each of the three different strains used in the current experiments, immediately prior to and after the operative procedure. Systemic blood pressures were obtained by catheterization of the infrarenal abdominal aorta, and measured using a Grass Model 7 polygraph (Grass Instrument Co., Quincy, Mass.). An arterial blood sample was obtained from this infrarenal aortic catheter; arterial pH, $PCO_2$ (mm Hg), $pO_2$ (mm Hg) and hemoglobin oxygen saturation (%) were measured using a Blood Gas Analyser and Hemoglobinometer (Grass Instrument Co., Quincy, Mass.). Because of the need for arterial puncture and abdominal manipulation to measure these physiologic parameters, animals were designated solely for these measurements (stroke volumes, neurologic outcome, and cerebral blood flows were not measured in these same animals).

Transcranial measurements of cerebral blood flow were made using laser doppler flowmetry (Perimed, Inc., Piscataway, N.J.) after reflection of the skin overlying the calvarium, as previously described (10) (transcranial readings were consistently the same as those made after craniectomy in pilot studies). To accomplish these measurements, animals were placed in a stereotactic head frame, after which they underwent midline skin incision from the nasion to the superior nuchal line. The skin was swept laterally, and a 0.7 mm straight laser doppler probe (model #PF2B) was lowered onto the cortical surface, wetted with a small amount of physiologic saline. Readings were obtained 2 mm posterior to the bregma, both 3 mm and 6 mm to each side of midline using a sterotactic micromanipulator, keeping the angle of the probe perpendicular to the cortical surface. Relative cerebral blood flow measurements were made immediately after anesthesia, after occlusion of the MCA, and immediately prior to euthanasia, and are expressed as the ratio of the doppler signal intensity of the ischemic compared with the nonischemic hemisphere. For animals subjected to transient cerebral ischemia, additional measurements were made just before and just after withdrawal of the suture, initiating reperfusion.

The surgical procedure/intraluminal MCA occlusion was considered to be technically adequate if $\geq 50\%$ reduction in relative cerebral blood flow was observed immediately following placement of the intraluminal occluding catheter (15 of the 142 animals used in this study [10.6%] were exluded due to inadequate drop in blood flow at the time of occlusion). These exclusion criteria were shown in preliminary studies to yield levels of ischemia sufficient to render consistent infarct volumes by TTC staining. Reperfusion was considered to be technically adequate if cerebral blood flow at catheter withdrawal was at least twice occlusion cerebral blood flow (13/17 animals in this study [76%]).

Temperature:

Core temperature during the peri-infarct period was carefully controlled throughout the experimental period. Prior to surgery, a baseline rectal temperature was recorded (YSI Model 74 Thermistemp rectal probe, Yellow Springs Instruments, Inc., Yellow Springs, OH). Intraoperatively, temperature was controlled using a thermocouple-controlled operating surface. Following MCA occlusion, animals were placed for 90 minutes in an incubator, with animal temperature maintained at 37° C. using the rectal probe connected via thermocouple to a heating source in the incubator. Temperature was similarly controlled in those animals subjected to transient ischemia, including a 45 minute (ischemic) period as well as a 90 minute post-ischemic period in the incubator. Following placement in the core-temperature incubator, animals were returned to their cages for the remaining duration of pre-sacrifice observation.

Neurological Exam: Prior to giving anesthesia at the time of euthanasia, mice were examined for obvious neurological deficit using a four-tiered grading system: (1) normal spontaneous movements, (2) animal circling towards the right, (3) animal spinning to the right, (4) animal crouched on all fours, unresponsive to noxious stimuli. This system was shown in preliminary studies to accurately predict infarct size, and is based on systems developed for use in rats (6).

Data Analysis:

Stroke volumes, neurologic outcome scores, cerebral blood flows and arterial blood gas data were compared using an unpaired Student's t-test. Values are expressed as means±SEM, with a $p<0.05$ considered statistically significant. Mortality data, where presented was evaluated using chi-squared analysis.

Figure 2:
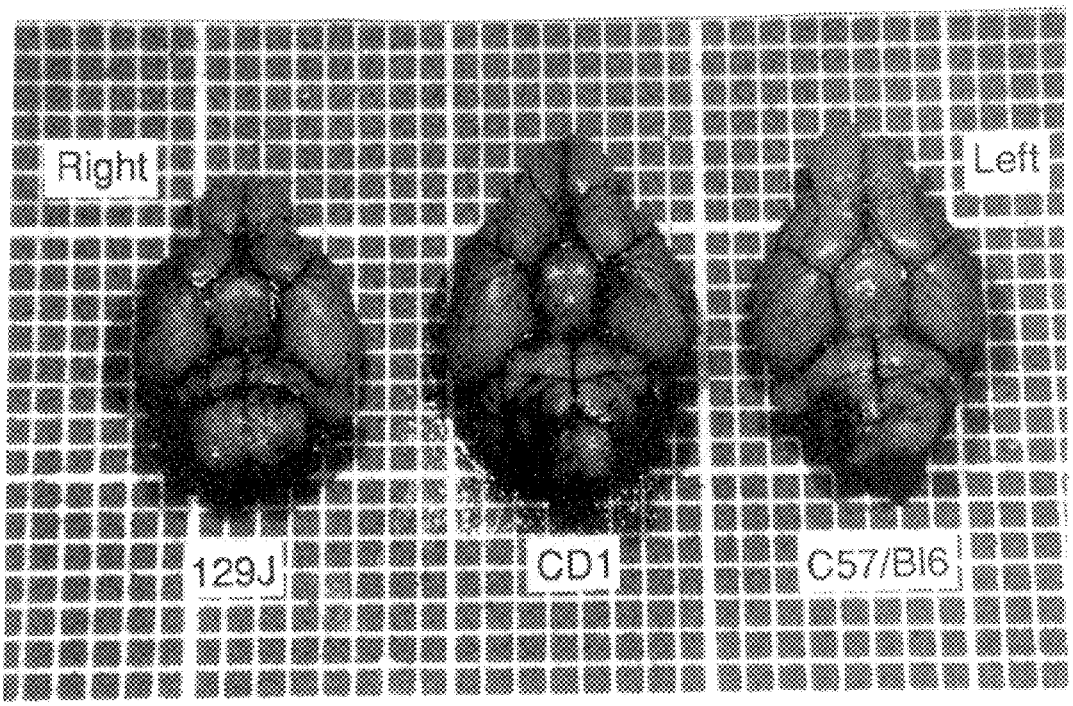
FIG. 2. Comparison of cerebrovascular anatomy between strains of mice. Following anesthesia, mice were given an intracardiac injection of India ink followed by humane euthanasia. An intact Circle of Willis can be observed in all strains, including bilateral posterior communicating arteries, indicating that there are no gross strain-related differences in cerebrovascular anatomy.

Results:

Effects of Strain:

Three different commonly used mouse strains (CD1, C57/Bl6, and 129J) were used to compare the variability in stroke outcome following permanent focal cerebral ischemia. To establish that there were no gross anatomic differences in collateralization of the cerebral circulation, the Circle of Willis was visualized using India ink in all three strains (FIG. 2). These studies failed to reveal any gross anatomic differences. Mice of similar sizes (20±0.8 g, 23±0.4 g, and 23±0.5 g for 129J, CD1, and C57Bl mice, respectively) were then subjected to permanent focal ischemia under normothermic conditions using a 12 mm length of 6-0 nylon occluding suture. Significant strain-related differences in infarct volume were noted, with infarcts in 129J mice being significantly smaller than those observed in CD1 and C57/Bl6 mice despite identical experimental conditions (FIG. 3A). Differences in infarct size were paralleled by neurological exam, with the highest scores (i.e., most severe neurologic damage) being seen in the C57/Bl6 and CD1 mice (FIG. 3B).

To determine the relationship between infarct volume and cerebral blood flow to the core region, laser doppler flowmetry was performed through the thin murine calvarium. No preoperative strain-related differences in cerebral blood flow were observed, corresponding to the lack of gross anatomic differences in vascular anatomy (FIG. 2). Measurement of cerebral blood flow immediately following insertion of the occluding catheter revealed that similar degees of flow reduction were created by the procedure (the percentage of ipsilateral/contralateral flow immediately following insertion of the obstructing catheter was 23±2%, 19±2%, 17±3% for 129J, CD1, and C57/Bl6 mice, respectively). Not surprisingly, blood flow to the core region measured at 24 hours just prior to euthanasia demonstrated the lowest blood flows in those animals with the most severe neurologic injury (FIG. 3C).

Anatomic and Physiologic Characteristics of Mice:

Baseline arterial blood pressures, as well as arterial blood pressures following middle cerebral artery occlusion, were nearly identical for all animals studied, and were not effected by mouse strain or size (Table I). Analysis of arterial blood for pH, $pCO_2$, and hemoglobin oxygen saturation (%) similarly revealed no significant differences (Table I).

Effect of Animal Size and Bore of the Occluding Suture:

To investigate the effects of mouse size on stroke outcome, mice of two different sizes (23±0.4 g and 31±0.7 g) were subjected to permanent focal cerebral ischemia. To eliminate other potential sources of variability in these experiments, experiments were performed under normothermic conditions in mice of the same strain (CD1), using occluding sutures of identical length and bore (12 mm 6-0 nylon). Under these conditions, small mice (23±0.4 g) sustained consistently large infarct volumes (28±9% of ipsilateral hemisphere). Under identical experimental conditions, large mice (31±0.7 g) demonstrated much smaller infarcts (3.2±3%, p=0.02, FIG. 4A), less morbidity on neurological exam (FIG. 4B), and a tendency to maintain higher ipsilateral cerebral blood flow following infarction than smaller animals (FIG. 4C).

Because it was hypothesized that the reduction in infarct size infarcts in these large animals was related to a mismatch in diameter/length between occluding suture and the cerebral blood vessels, longer/thicker occluding sutures were fashioned (13 mm, 5-0 nylon) for use in these larger mice. Large CD1 mice (34±0. 8 g) which underwent permanent occlusion with these larger occluding sutures sustained a marked increase in infarct volumes (50±10% of ipsilateral hemisphere, p<0.0001 compared with large mice infarcted with the smaller occluding suture, FIG. 4A). These larger mice infarcted with larger occluding sutures demonstrated higher neurologic deficit scores (FIG. 4B) and lower ipsilateral cerebral blood flows (FIG. 4C) compared with similarly large mice infarcted with smaller occluding sutures.

Effects of Temperature:

To establish the role of perioperative hypothermia on the stroke volumes and neurologic outcomes following MCA occlusion, small C57/Bl6 mice (22±0.4 g) were subjected to permanent MCA occlusion with 12 mm 6-0 gauge suture, with normothermia maintained for two different durations; Group 1 ("Normothermia") was operated as described above, maintaining temperature at 37° C. from the preoperative period until 90 minutes post-occlusion. Group 2 animals ("Hypothermia") were maintained at 37° C. from preop to only 10 minutes post-occlusion, as has been described previously (14). Within 45 minutes following removal from the thermocouple-controlled warming incubator, core temperature in this second group of animals dropped to 33.1±0.4° C. (and dropped further to 31.3±0.2° C. at 90 minutes). Animals operated under conditions of prolonged normothermia (Group 1) exhibited larger infarct volumes (32±9%) than hypothermic (Group 2) animals (9.2±5%, p=0.03, FIG. 5A). Differences in infarct volume were mirrored by differences in neurological deficit (3.2±0.4 vs. 2.0±0.8, p=0.02, FIG. 5B), but were largely independent of cerebral blood flow (52±5 vs. 52±7, p=NS, FIG. 5C).

Effects of Transient MCA Occlusion:

Because reperfusion injury has been implicated as an important cause of neuronal damage following cerebrovascular occlusion (25), a subset of animals was subjected to a transient (45 minute) period of ischemia followed by reperfusion as described above, and comparisons made with those animals which underwent permanent MCA occlusion. The time of occlusion was chosen on the basis of preliminary studies (not shown) which demonstrated unacceptibly high mortality rates (>85%) with 180 minutes of ischemia and rare infarction (<15%) with 15 minutes of ischemia. To minimize the confounding influence of other variables, other experimental conditions were kept constant (small (22.5±0.3 g) C57/Bl6 mice were used, the occluding suture consisted of 12 mm 6-0 nyon, and experiments were performed under normothermic conditions). The initial decline in CBF immediately post-occlusion were similar in both groups (16±2% vs 17±3%, for transient vs permanent occlusion groups, respectively, p=NS). Reperfusion was confirmed both by laser doppler (2.3-fold increase in blood flow following removal of the occluding suture to 66±13%), and visually by intracardiac methylene blue dye injection in representative animals. Infarct sizes (29±10% vs. 32±9%), neurologic deficit scores (2.5±0.5 vs. 3.2±0.4), and sacrifice cerebral blood flow (46±18% vs. 53±5%) were quite similar between animals subjected to transient cerebral ischemia and reperfusion and those subjected to permanent focal cerebral ischemia (p =NS, for all groups) (FIGS. 6A–6C).

Discussion:

The growing availability of genetically altered mice has led to an increasing use of murine models of focal cerebral ischemia to impute specific gene products in the pathogenesis of stroke. Although recent publications describe the use of an intraluminal suture to occlude the middle cerebral artery to create permanent and/or transient cerebral ischemia in mice, there has been only scant description of the necessary modifications of the original technical report in rats (8,14,17–19,24,26). The experiments described herein not only provide a detailed technical explanation of a murine model suitable for either permanent or transient focal middle cerebral artery ischemia, but also address potential sources of variability in the model.

Importance of Strain:

One of the most important potential sources of variability in the murine cerebral ischemia model described herein is related to the strain of animal used. The data suggest that, of the three strains tested, 129J mice are particularly resistant to neurologic injury following MCA occlusion. Although Barone similarly found differences in stroke volumes between 3 strains of mice (BDF, CFW and BALB/C), these differences were ascribed to variations in the posterior communicating arteries in these strains (4). As anatomical differences in cerebrovascular anatomy were not grossly apparent in the study (FIG. 2), the data suggests that non-anatomic strain-related differences are also important in outcome following MCA occlusion.

As stroke outcome differs significantly between 2 strains of mice (129J and C57/Bl6) commonly used to produce transgenic mice via homologous recombination in embryonic stem cells (11), the data suggest an important caveat to experiments performed with transgenic mice. Because early founder progeny from the creation of transgenic animals with these strains have a mixed 129J/C57/Bl6 background, ideally experiments should be performed either with sibling controls or after a sufficient number of backcrossings to ensure strain purity.

Importance of Size:

Larger animals require a longer and thicker intralumenal suture to sustain infarction volumes which are consistent with those obtained in smaller animals with smaller occluding sutures. Size matching of animal and suture appear to be important not only to produce consistent cerebral infarction, but whereas too small a suture leads to insufficient ischemia, too large a suture leads to frequent intracerebral hemorrhage and vascular trauma.

The use of animals of similar size is important not only to minimize potential age-related variability in neuronal susceptibility to ischemic insult, but also to ensure that small differences in animal size do not obfuscate meaningful data comparison. In this example, it is demonstrated that size differences of as little as 9 grams can have a major impact on infarct volume and neurologic outcome following cerebral ischemia. Further experiments using larger bore occluding suture in larger animals suggest that the increased propensity of smaller animals to have larger strokes was not due to a relative resistance of larger animals to ischemic neuronal damage, but was rather due to small size of the suture used to occlude the MCA in large animals. Although these data were obtained using CD1 mice, similar studies have been performed and found these results to be true with other mouse strains as well, such as C57/Bl6. Previously published reports use mice of many different sizes (from 21 g to 35 g), as well as different suture diameters and lengths which are often unreported (14,17). The studies indicate that animal and suture size are important methodological issues which must be addressed in scientific reports.

Importance of Temperature:

It has long been recognized that hypothermia protects a number of organs from ischemic injury, including the brain. Studies performed in rats have demonstrated that intraischemic hypothermia up to 1 hour post-MCA occlusion is protective (2,15), reducing both mortality and infarct volumes with temperatures of 34.5 degrees. Although these results have been extrapolated to murine models of cerebral ischemia in that studies often describe maintenance of normothermia in animals, the post-MCA occlusion temperature monitoring periods have been extremely brief ("immediately after surgery" or "10 minutes after surgery") (4,14). The results indicate that animals fail to autoregulate their temperature beyond these brief durations, becoming severely hypothermic during the postoperative period, and that temperature differences up to 90 minutes following MCA occlusion can have a profound effect on indices of stroke outcome following MCA occlusion (longer durations of normothermia were not studied). While others have ensured normothermia using a feedback system based on rectal temperature similar to the one described herein, the duration of normothermia is often not specified (17). The results argue for clear identification of methods for monitoring and maintaining temperature, as well as the durations involved, so that experimental results can be compared both within and between Centers studying the pathophysiology of stroke.

Transient vs Permanent Occlusion:

The pathophysiology of certain aspects of permanent cerebral ischemia may well be different from that of cerebral ischemia followed by reperfusion, so it was important that a model be described which permitted analysis of either condition. Although differences between these two models were not extensively tested in the current series of experiments, under the conditions tested (45 minutes of ischemia followed by 23 hours of reperfusion), no significant differences were found in any index of stroke outcome. Variable durations of ischemia and reperfusion have been reported in other murine models of transient cerebral ischemia, with ischemic times ranging from 10 minutes to 3 hours and reperfusion times ranging from 3 to 24 hours (17,24). Studies in rats have shown that short periods of ischemia followed by reperfusion are associated with smaller infarcts than permanent occlusion (21,25). However as the duration of ischemia increases beyond a critical threshold (between 120 and 180 minutes), reperfusion is associated with larger infarcts (7,21,26). For the current series of experiments, the durations of ischemia and reperfusion were chosen so as to obtain infarcts comparable to those observed following permanent MCA occlusion, which is likely to explain why the data failed to show differences between permanent and transient ischemia. These durations in the transient model were chosen after pilot experiments revealed that shorter ischemic durations (15 minutes) rarely led to infarction, whereas 180 minutes of occlusion followed by reperfusion led to massive infarction and nearly 100% mortality within 4–6 hours in normothermic animals (unpublished observation). Although indices of stroke outcome may be measured earlier than 24 hours, the 24 hour observation time was elected because observation at this time permits the study of delayed penumbral death, which is likely to be clinically relevant to the pathophysiology of stroke in humans. Furthermore, 24 hours has been shown in a rat model to be sufficient for full infarct maturation (3,12,15,16).

Technical Aspects of the Murine Model:

Technical aspects of the surgery needed to create focal cerebral ischemia in mice differ in certain important respects from that in rats. Self-retaining retractors, which have been advocated in previous reports in rats (26), are unweildy in mice. Suture-based retraction secured with tape provides a superior alternative. In rats, clip occlusion of the proximal and distal carotid artery after mobilization of the external carotid artery has been reported (26), but creates more carotid trauma and hemmorhage in mice. Without distal internal carotid control, which has not been previously described in mice, backbleeding from the external carotid artery is consistently uncontrollable. Using the techniques described in this paper, surgery can be completed with virtually no blood loss, which is especially important given the small blood volume in mice.

Unlike the rat model, the occlusion and transection of the external carotid artery branches and the pterygopalatine artery in the murine model is achieved with electrocautery alone. Previous reports of murine surgery have been unclear as to whether or not the pterygopalatine artery was taken (17,24). Others have described a method with permanent occlusion of the common carotid artery and trans-carotid insertion of the suture without attention to either the external carotid system or the pterygopalatine artery. While effective for permanent occlusion, this latter method makes reperfusion studies impossible.

The method of reperfusion originally described in the rat requires blind catheter withdrawal without anesthesia (26). When attempted in pilot studies in mice, several animals hemorrhaged. Therefore, a method of suture removal under direct visualization in the anesthetized animal was developed, which not only allows visual confirmation of extracranial carotid artery reperfusion, but also affords meticulous hemostasis. Further, the method permits immediate pre- and post-reperfusion laser doppler flowmetry readings in the anesthetized animal.

These laser doppler flowmetry readings are similar to those described by Kamii et al. and Yang et al. in that the readings are made intermittantly and with the use of a stereotactic micromanipulator (17,24). The readings differ, however, in that the coordinates used (2 mm posterior and 3 and 6 mm lateral to the bregma) are slightly more lateral and posterior than the previously published core and penumbral coordinates (1 mm posterior and 2 mm and 4.5 mm lateral to the bregma). These coordinates, which were adopted based on pilot studies, are the same as those used by Huang et al (14).

Conclusion:

These studies demonstrate specific technical aspects of a murine model of focal cerebral ischemia and reperfusion which permits reproducibility of measurements between different laboratories. In addition, these studies provide a framework for understanding important procedural variables which can greatly impact on stroke outcome, which should lead to a clear understanding of non-procedure related differences under investigation. Most importantly, this study points to the need for careful control of mouse strain, animal and suture size, and temperature in experimental as well as control animals. Conditions can be established so that stroke outcome is similar between models of permanent focal cerebral ischemia and transient focal cerebral ischemia, which should facilitate direct comparison and permit the study of reperfusion injury. The model described in this study should provide a cohesive framework for evaluating the results of future studies in transgenic animals, to facilitate an understanding of the contribution of specific gene products in the pathophysiology of stroke.

Table I.

Pre- and post-operative physiologic parameters. MAP, mean arterial pressure; $pCO_2$, partial pressure of arterial $CO_2$ (mm Hg); $O_2$ Sat, $O_2$ saturation (%); Hb, hemoglobin concentration (g/dl); Preoperative, anesthetized animals prior to carotid dissection; Sham, anesthetized animals undergoing the surgical described in the text, immediately prior to introduction of the occluding suture; Stroke, anesthetized animals undergoing the surgical described in the text, immediately after introduction of the occluding suture. p=NS for all between-group comparisons. (data shown is for small 22 gram C57/Bl6 mice).

| PARAMETER | PREOPERATIVE | SHAM | STROKE |
| --- | --- | --- | --- |
| MAP | 102 ± 5.5 | 94 ± 1.9 | 88 ± 4.9 |
| pH | 7.27 ± 0.02 | 7.23 ± 0.04 | 7.28 ± 0.01 |
| $pCO_2$ | 46 ± 1.3 | 44 ± 1.3 | 47 ± 3.5 |
| $O_2$ Sat | 89 ± 1.6 | 91 ± 1.8 | 85 ± 2.2 |
| Hb | 14.6 ± 0.42 | 14.3 ± .12 | 14.2 ± 0.12 |

REFERENCES

1. Backhaub C, et al. (1992) J Pharmacol Methods 27:27–32.
2. Baker C J, et al. (1992) J Neurosurg 77:438–444.
3. Baker C J, et al. (1995) Neurosurgery 36:1–9.
4. Barone F C, et al. (1993) J Cereb Blood Flow Metab 13:683–692.
5. Bederson J B, et al. (1986) Stroke 17:1304–1308.
6. Bederson J B, et al. (1986) Stroke 17:472–476.
7. Buchan A M, et al. (1992) Stroke 23:273–279.
8. Chan P H, et al. (1993) NeuroReport 5:293–296.
9. Chiamulera C, et al. (1993) Brain Res 606:251–258.
10. Dirnagl U, et al. (1989) J Cereb Blood Flow Metab 9:589–596.
11. Donehower L A, et al. (1992) Nature 356:215–221.
12. Frazzini V I, et al. (1994) Neurosurgery 34:1040–1046.
13. Ginsberg M D and Busto R (1989) Stroke 20:1627–1642.
14. Huang Z, et al. (1994) Science 265:1883–1885.
15. Kader A, et al. (1992) Neurosurgery 31:1056–1061.
16. Kader A, et al. (1993) Stroke 24:1709–1716.
17. Kamii H, et al. (1994) J Cereb Blood Flow Metab 14:478–486.
18. Kinouchi H, et al. (1991) Proc Natl Acad Sci 88: 11158–11162.
19. Martinou J-C, et al. (1994) Neuron 13:1017–1030.
20. Memezawa H, et al. (1992) Stroke 23:552–559.
21. Menzies S A, et al. (1992) Neurosurgery 31:100–107.
22. Tamura A, et al. (1981) J Cereb Blood Flow Metabol 1: 53–60.
23. Welsh F A, et al. (1987) J Neurochem 49:846–851.
24. Yang G, et al. (1994) Stroke 25:165–170.
25. Yang G-Y and Betz A L (1994) Stroke 25: 1658–65.
26. Zea-Longa E, et al. (1989) Stroke 20:84–91.

EXAMPLE 2

Factor IXai

Factor IX is a clotting factor which exists in humans and other mammals, and is an important part of the coagulation pathway. In the normal scheme of coagulation, Factor IX is activated by either Factor XIa or a tissue factor/VIIa complex to its active form, Factor IXa. Factor IXa then can activate Factor X, which triggers the final part of the coagulation cascade, leading to thrombosis. Because Factor X can be activated by one of two pathways, either the extrinsic (via VIIa/tissue factor) or the intrinsic pathways (via Factor IXa), we hypothesized that inhibiting Factor IXa might lead to impairment of some forms of hemostasis, but leave hemostasis in response to tissue injury intact. In other words, it might lead to blockade of some types of clotting, but might not lead to excessive or unwanted hemorrhage. Factor IXai is Factor IXa which has been chemically modified so as to still resemble Factor IXa (and therefore, can compete with native Factor IXa), but which lacks its activity. This can "overwhelm" or cause a competitive inhibition of the normal Factor IXa-dependent pathway of coagulation. Because Factor IXa binds to endothelium and platelets and perhaps other sites, blocking the activity of Factor IXa may also be possible by administering agents which interfere with the binding of Factor IXa (or by interfering with the activation of Factor IX).

In stroke and other ischemic disorders, there may be clinical benefit derived by lysing an existing thrombus, but there is also the potentially devastating complication of hemorrhage. In the current experiments, the mouse model of cerebral ischemia and reperfusion (stroke) was used. Mice received an intravenous bolus of 300 µg/kg of Factor IXai just prior to surgery. Strokes were created by intraluminal occlusion of the right middle cerebral artery. When stroke outcomes were measured 24 hours later, animals that had received Factor IXai had smaller infarct volumes, improved cerebral perfusion, less neurological deficits, and reduced mortality compared with controls which underwent the same surgery but which did not receive Factor IXai. (See Table II.) It was also noted that the Factor IXai animals were free of apparent intracerebral hemorrhage. By contrast, intracerebral hemorrhage was occasionally noted in the control animals not receiving Factor IXai.

TABLE II

| | Control | | Experimental (Factor IXai) | | |
|---|---|---|---|---|---|
| | mean | sd | mean | sd | stats |
| weight | 26.91 | 3.21 | 25.25 | 2.49 | 0.14 |
| dopp | 0.96 | 0.24 | 1.04 | 0.35 | 0.52 |
| occ dop 1 | 0.18 | 0.07 | 0.16 | 0.08 | 0.60 |
| occ dop 2 | 0.40 | 0.22 | 0.43 | 0.20 | 0.68 |
| reper dop | 0.55 | 0.42 | 0.53 | 0.30 | 0.89 |
| sac dop | 0.38 | 0.25 | 0.75 | 0.31 | 0.02 |
| grade | 2.22 | 0.67 | 1.67 | 0.49 | |
| I/C Ratio | 1.18 | 0.20 | 1.08 | | |
| inf vol | 21.16 | 25.14 | 3.47 | 12.03 | 0.0452 |
| count | 11 | | 16 | | |

Abbreviations:
dopp = doppler;
occ dop = occlusion doppler;
reper dop = reperfusion doppler;
sac dop = sacrifice doppler.

EXAMPLE 3
Active-site Blocked Factor IXa Limits Microvascular Thrombosis and Cerebral Injury in Murine Stroke Without Increasing Intracerebral Hemorrhage The clinical dilemma in stroke treatment is that agents which restore vascular patency increase the risk of intracerebral hemorrhage. Active-site blocked Factor IXa (IXai) competes with native Factor IXa to inhibit assembly of Factor IXa into the intrinsic Factor X activation complex. When pretreated with Factor IXai, mice subjected to focal cerebral ischemia and reperfusion demonstrated reduced microvascular fibrin and platelet deposition, increased cerebral perfusion, and significantly smaller cerebral infarcts than vehicle-treated controls. Factor IXai-mediated cerebroprotection was dose-dependent, not associated with intracerebral hemorrhage at therapeutically effective doses, and was seen even when Factor IXai was administered after the onset of cerebral ischemia. Administration of Factor IXai represents a new strategy to treat stroke in evolution without increasing the risk of intracerebral hemorrhage.

Introduction

Timely reestablishment of blood flow to ischemic brain represents the current treatment paradigm for acute stroke[1-3]. Administration of a thrombolytic agent, even when given under optimal conditions, may not achieve this desired clinical result. Perfusion often fails to return to preischemic levels (postischemic hypoperfusion), suggesting that ischemic injury is not produced solely by the original occlusion, but that there is also an element of microcirculatory failure. In addition, thrombolysis of acute stroke is associated with an increased risk of intracerebral hemorrhage (ICH)[1-4], indicating that there remains a clear need to identify new agents which can promote reperfusion without increasing the risk of ICH.

Following an ischemic event, the vascular wall is modified from its quiescent, anti-adhesive, antithrombotic state, to one which promotes leukocyte adhesion and thrombosis. In acute stroke, active recruitment of leukocytes by adhesion receptors expressed in the ipsilateral microvasculature, such as ICAM-1[5] and P-selectin[6], potentiates postischemic hypoperfusion. However, experiments with mice deletionally mutant for each of these genes demonstrate that even in their absence, postischemic cerebral blood flow (CBF) returns only partially to baseline, suggesting the existence of additional mechanisms responsible for postischemic cerebrovascular no-reflow. To explore this possibility, the first set of experiments was designed to test the hypothesis that local thrombosis occurs at the level of the microvasculature (distal to the site of primary occlusion) in stroke.

To assess the deleterious consequences of microvascular thrombosis in stroke, the second set of experiments tested the hypothesis that selective blockade of the intrinsic pathway of coagulation could limit microvascular thrombosis, thereby protecting the brain in stroke. The strategy of selective inhibition of the intrinsic pathway of coagulation was chosen because it is primarily responsible for intravascular thrombosis. Heparin, hirudin, and fibrinolytic agents interfere with the final common pathway of coagulation to inhibit the formation or accelerate the lysis of fibrin, and therefore increase the propensity for ICH. We hypothesized that selective blockade of IXa/VIIIa/X activation complex assembly might provide a novel mechanism to limit intravascular thrombosis while preserving mechanisms of extravascular hemostasis by the extrinsic/tissue factor pathway of coagulation which may be critical in infarcted brain tissue or adjacent regions where small vessels are friable and subject to rupture. We used a novel strategy in which a competitive inhibitor of Factor IXa (active-site blocked IXa, or IXai) was given to mice subjected to stroke to test the hypothesis that it would improve stroke outcome without increasing ICH.

Methods

Murine stroke model: Transient focal cerebral ischemia was induced in mice by intralumenal occlusion of the middle cerebral artery (45 minutes) and reperfusion (22 hrs) as previously reported[7]. Serial measurements of relative cerebral blood flow (CBF) were recorded via laser doppler flowmetry[7], and infarct volumes (k ipsilateral hemisphere) determined by planimetric/volumetric analysis of triphenyl tetrazolium chloride (TTC)-stained serial cerebral sections[7].

$^{111}$Indium-platelet studies: Platelet accumulation was determined using $^{111}$Indium labeled platelets, collected and prepared as previously described[8]. Immediately prior to surgery, mice were given $5\times10^6$ $^{111}$In-labeled-platelets intravenously; deposition was quantified after 24 hours by as ipsilateral cpm/contralateral cpm.

Fibrin Immunoblotting/Immunostaining:

The accumulation of fibrin was measured following sacrifice (of fully heparinized animals) using immunoblotting/immunostaining procedures which have been recently described and validated[9]. Because fibrin is extremely insoluble, brain tissue extracts were prepared by plasmin digestion, then applied to a standard SDS-polyacrylamide gel for electrophoresis, followed by immunoblotting using a polyclonal rabbit anti-human antibody prepared to gamma—gamma chain dimers present in cross-linked fibrin which can detect murine fibrin, with relatively little cross-reactivity with fibrinogen[10]. Fibrin accumulation was reported as an ipsilateral to contralateral ratio. In additional experiments, brains were embedded in paraffin, sectioned, and immunostained using the same anti-fibrin antibody.

Spectrophotometric Hemoglobin Assay and Visual ICH Score:

ICH was quantified by a spectrophotometric-based assay which we have developed and validated[11,12] In brief, mouse brains were homogenized, sonicated, centrifuged, and methemoglobin in the supernatants converted (using Drabkin's reagent) to cyanomethemoglobin, the concentration of which was assessed by measuring O.D. at 550 nm against a standard curve generated with known amounts of hemoglobin. Visual scoring of ICH was performed on 1 mm serial coronal sections by a blinded observer based on maximal hemorrhage diameter seen on any of the sections [ICH score 0, no hemorrhage; 1, <1 mm; 2, 1–2 mm; 3, >2–3 mm; 4, >3 mm].

Preparation of Factor IXai[13]:

Factor IXai was prepared by selectively modifying the active site histidine residue on Factor IXa, using dansyl-glu-gly-arg-chloromethylketone. Proplex was applied to a preparative column containing immobilized calcium-dependent monoclonal antibody to Factor IX. The column was washed, eluted with EDTA-containing buffer, and Factor IX in the eluate (confirmed as a single band on SDS-PAGE) was then activated by applying Factor XIa (incubating in the presence of $CaCl_2$). Purified Factor IXa was reacted with a 100-fold molar excess of dansyl-glu-gly-arg chloromethylketone, and the mixture dialyzed. The final product (IXai), devoid of procoagulant activity, migrates identically to IXa on SDS-PAGE. This material (Factor IXai) was then used for experiments following filtration (0.2 $\mu$m) and chromatography on DeToxi-gel columns, to remove any trace endotoxin contamination (in sample aliquots, there was no detectable lipopolysaccharide). IXai was subsequently frozen into aliquots at $-80°$ C. until the time of use. For those experiments in which IXai was used, it was given as a single intravenous bolus at the indicated times and at the indicated doses.

Results

To create a stroke in a murine model, a suture is introduced into the cerebral vasculature so that it occludes the orifice of the right middle cerebral artery, rendering the subtended territory ischemic. By withdrawing the suture after a 45 minute period of occlusion, a reperfused model of stroke is created; mice so treated demonstrate focal neurological deficits as well as clear-cut areas of cerebral infarction. Because the occluding suture does not advance beyond the major vascular tributary (the middle cerebral artery), this model provides an excellent opportunity to investigate "downstream" events that occur within the cerebral microvasculature in response to the period of interrupted blood flow. Using this model, the role of microvascular thrombosis was investigated as follows. To demonstrate that platelet-rich thrombotic foci occur within the ischemic cerebral hemisphere, $^{111}$In-labeled platelets were administered to mice immediately prior to the introduction of the intraluminal occluding suture, to track their deposition during the ensuing period of cerebral ischemia and reperfusion. In animals not subjected to the surgical procedure to create stroke, the presence of platelets was approximately equal between the right and left hemispheres, as would be expected [FIG. 7A, left bar]. However, when animals were subjected to stroke (and received only vehicle to control for subsequent experiments), radiolabeled platelets preferentially accumulated in the ischemic (ipsilateral) hemisphere, compared with significantly less deposition in the contralateral (nonischemic) hemisphere [FIG. 7A, middle bar]. These data support the occurrence of platelet-rich thrombi in the ischemic territory. When Factor IXai is administered to animals prior to introduction of the intraluminal occluding suture, there is a significant reduction in the accumulation of radiolabelled platelets in the ipsilateral hemisphere [FIG. 7A, right bar].

Another line of evidence also supports the occurrence of microvascular thrombosis in stroke. This data comes from the immunodetection of fibrin, using an antibody directed against a neoepitope on the gamma—gamma chain dimer of cross-linked fibrin. Immunoblots demonstrate a band of increased intensity in the ipsilateral (right) hemisphere of vehicle-treated animals subjected to focal cerebral ischemia and reperfusion [FIG. 7B, "Vehicle"]. In animals treated with Factor IXai (300 $\mu$g/kg) prior to stroke, there is no apparent increase in the ipsilateral accumulation of fibrin [FIG. 7B, "Factor IXai"]. To demonstrate that fibrin accumulation was due to the deposition of intravascular fibrin (rather than due to nonspecific permeability changes and exposure to subendothelial matrix), fibrin immunostaining clearly localized the increased fibrin to the lumina of ipsilateral intracerebral microvessels [FIG. 7C].

To investigate whether Factor IXai can limit intracerebral thrombosis and restore perfusion, IXai was given to mice immediately prior to stroke (300 $\mu$g/kg). These experiments demonstrate both a reduction in $^{111}$In-platelet accumulation in the ipsilateral hemisphere [FIG. 8A] as well as decreased evidence of intravascular fibrin by immunostaining. Furthermore, there is a significant increase in CBF by 24 hours, suggesting the restoration of microvascular patency by Factor IXai [FIG. 8A]. The clinical relevance of this observation is underscored by the ability of Factor IXai to reduce cerebral infarct volumes [FIG. 8B]. These beneficial effects of Factor IXai were dose dependent, with 600 $\mu$g/kg being the optimal dose [FIG. 8C]. Because the development of ICH is a major concern with any anticoagulant strategy in the setting of stroke, the effect of IXai on ICH was measured using our recently validated spectrophotometric method for quantifying ICH[11,12]. These data indicate that at the lowest doses (and the most effective ones), there is no significant increase in ICH [FIG. 9A]. At the highest dose tested (1200 $\mu$g/kg), there is an increase in ICH, which was corroborated by a semiquantitative visual scoring method which we have also recently reported [FIG. 9B][11,12].

Because therapies directed at improving outcome from acute stroke must be given after clinical presentation, and because fibrin continues to form following the initial ischemic event in stroke, we tested whether IXai might be effective when given following initiation of cerebral ischemia. IXai given after middle cerebral artery occlusion (following removal of the occluding suture) provided significant cerebral protection judged by its ability to significantly reduce cerebral infarction volumes compared with vehicle-treated controls [FIG. 10].

Discussion

The data in these studies demonstrate clear evidence of intravascular thrombus formation (both platelets and fibrin) within the post-ischemic cerebral microvasculature. The pathophysiological relevance of microvascular thrombosis in stroke is underscored by the ability of Factor IXai to reduce microvascular thrombosis (both platelet and fibrin accumulation are reduced, with an attendant increase in postischemic CBF) and to improve stroke outcome. These potent antithrombotic actions of Factor IXai are likely to be clinically significant in the setting of stroke, because Factor IXai not only reduces infarct volumes in a dose-dependent manner, but it does so even when given after the onset of stroke. In addition, at clinically relevant doses, treatment with Factor IXai does not cause an increase in ICH, making selective inhibition of Factor IXa/VIIIa/X activation complex assembly with Factor IXai an attractive target for stroke therapy in humans.

There are a number of reasons why targetted anticoagulant strategies might be an attractive alternative to the current use of thrombolytic agents in the management of acute stroke, because of their checkered success in clinical trials. Theoretically, an ideal treatment for acute stroke would prevent the formation or induce dissolution of the fibrin-platelet mesh that causes microvascular thrombosis in the ischemic zone without increasing the risk of intracerebral hemorrhage. However, thrombolytic agents which have been studied in clinical trials of acute stroke have consistently increased the risk of intracerebral hemorrhage [1-4]. Streptokinase, given in the first several (<6) hours following stroke onset, was associated with an increased rate of hemorrhagic transformation (up to 67%); although there was increased early mortality, surviving patients suffered less residual disability. Administration of tissue-type plasminogen activator (tPA) within 7 hours (particularly within 3 hours) of stroke onset resulted in increased early mortality and increased rates of hemorrhagic conversion (between 7–20%), although survivors demonstrated less residual disability. In order to develop improved anticoagulant or thrombolytic therapies, several animal models of stroke have been examined. These models generally consist of the administration of clotted blood into the internal carotid artery followed by administration of a thrombolytic agent. In rats, tPA administration within 2 hours of stroke improved cerebral blood flow and reduced infarct size by up to 77%[14,15]. In a similar rabbit embolic stroke model, tPA was effective at restoring blood flow and reducing infarct size, with occasional appearance of intracerebral hemorrhage[16,17]. However, although there are advantages to immediate clot dissolution, these studies (as well as the clinical trials of thrombolytic agents) indicate that there is an attendant increased risk of intracerebral hemorrhage with this therapeutic approach.

Because of the usually precipitous onset of ischemic stroke, therapy has been targetted primarily towards lysing the major fibrinous/atheroembolic debris which occludes a major vascular tributary to the brain. However, as the current work demonstrates, there is an important component of microvascular thrombosis which occurs downstream from the site of original occlusion, which is likely to be of considerable pathophysiological significance for post-ischemic hypoperfusion (no-reflow) and cerebral injury in evolving stroke. This data is in excellent agreement with that which has been previously reported, in which microthrombi have been topographically localized to the ischemic region in fresh brain infarcts[18]. The use of an agent which inhibits assembly of the Factor IXa/VIIIa/X activation complex represents a novel approach to limiting thrombosis which occurs within microvascular lumena, without impairing extravascular hemostasis, the maintenance of which may be critical for preventing ICH. In the current studies, treatment with Factor IXai reduces microvascular platelet and fibrin accumulation, improves postischemic cerebral blood flow, and reduces cerebral infarct volumes in the setting of stroke without increasing ICH.

The potency of Factor IXai as an anticoagulant agent stems from the integral role of activated Factor IX in the coagulation cascade. Not only does a strategy of Factor IXa blockade appear to be effective in the setting of stroke, but it also appears to be effective at preventing progressive coronary artery occlusion induced following the initial application of electric current to the left circumflex coronary artery in dogs[13]. As in those studies, in which Factor IXai did not prolong the pro time.

The data which demonstrate that IXai given after the onset of stroke is effective leads to another interesting hypothesis, that the formation of thrombus represents a dynamic equilibrium between the processes of ongoing thrombosis and ongoing fibrinolysis. Even under normal (nonischemic) settings, this dynamic equilibrium has been shown to occur in man[19]. The data in the current studies, which show that Factor IXai is effective even when administered after the onset of stroke, suggests that this strategy restores the dynamic equilibrium, which is shifted after cerebral ischemia to favor thrombosis, back towards a more quiescent (antithrombotic) vascular wall phenotype.

As a final consideration, even if thrombolysis successfully removes the major occluding thrombus, and/or anticoagulant strategies are effective to limit progressive microcirculatory thrombosis, blood flow usually fails to return to pre-ischemic levels. This is exemplified by data in the current study, in which although CBF is considerably improved by Factor IXai (which limits fibrin/platelet accumulation), CBF still does not return to preischemic levels. This data supports the existence of multiple effector mechanisms for postischemic cerebral hypoperfusion, including postischemic neutrophil accumulation and consequent microvascular plugging, with P-selectin and ICAM-1 expression by cerebral microvascular endothelial cells being particularly germane in this regard[5,6]. When looked at from the perspective of leukocyte adhesion receptor expression, even when these adhesion receptors are absent, CBF levels are improved following stroke compared with controls but do not return to preischemic levels. Taken together, these data suggests that microvascular thrombosis and leukocyte adhesion together contribute to postischemic cerebral hypoperfusion.

In summary, administration of a competitive inhibitor of Factor IXa, active-site blocked Factor IXa, represents a novel therapy for the treatment of stroke. This therapy not only reduces microcirculatory thrombosis, improves postischemic cerebral blood flow, and reduces cerebral tissue injury following stroke, but it can do so even if given after the onset of cerebral ischemia and without increasing the risk of ICH. This combination of beneficial properties and relatively low downside risk of hemorrhagic transformation makes this an extremely attractive approach for further testing and potential clinical trials in human stroke.

REFERENCES

1. *New Engl. J. Med.* (1995)333:1581–1587.
2. Hacke W, et al. (1995) *JAMA* 274(13):1017–1025.
3. del Zoppo G J (1995) *N. Engl. J. Med.* 333(13):1632–1633.
4. Hommel M, et al. (1996) *N. Engl. J. Med.* 335:145–150.
5. Connolly E S Jr, et al. (1996) *J. Clin. Invest.* 97:209–216.
7. Connolly E S Jr, et al. (1996) *Neurosurg* 38(3):523–532.
8. Naka Y, et al. (1995) *Circ. Res.* 76:900–906.
9. Lawson C A, et al. (1997) *J. Clin. Invest.* 99:1729–1738.
10. Lahiri B, et al. (1981) *Thromb. Res.* 23:103–112.
12. Choudhri T F, et al. (1997) *Annual Meeting Joint Section on Cerebrovascular Surgery.*
13. Benedict C R, et al. (1991) *J Clin Invest* 88:1760–1765.
14. Papadopoulos S M, et al. (1987) *J Neurosurg* 67:394–398.
15. Overgaard K, et al. (1993) *Neurol Res* 15:344–349.
16. Carter L P, et al.(1992) *Stroke* 23:883–888.
17. Phillips D A, et al. (1990) *Stroke* 21:602–605.
18. Heye N, et al. (1992) *Acta Neurologica Scandinavica* 86:450–454.
19. Nossel H L (1981) *Nature* 1981;291:165–167

EXAMPLE 4

Active-site Blocked Factor IXa Limits Microvascular Thrombosis and Cerebral Injury in Murine Stroke Without Increasing Intracerebral Hemorrhage

[Please note the following abbreviations: CBF, cerebral blood flow; Factor IXai, active-site blocked factor IXa; ICAM-1, intercellular adhesion molecule-1; ICH, intracerebral hemorrhage; tPA, tissue plasminogen activator; TTC, triphenyl tetrazolium chloride.]

The clinical dilemma in stroke treatment is that agents which restore vascular patency increase the risk of intracerebral hemorrhage (ICH). It was hypothesized that inhibiting cerebral microvascular thrombosis by inhibiting intrinsic Factor IX-dependent coagulation may restore vascular patency in stroke without impairing extrinsic hemostatic mechanisms that may limit ICH. Active-site blocked Factor IXa (IXai) was formed from purified factor IXa by dansylation of its active site, to compete with native Factor IXa to inhibit assembly of Factor IXa into the intrinsic Factor X activation complex. Although in vitro, Factor IXai had little effect on the PT or PTT, it prolonged clotting time in an assay in which Factor IX-deficient plasma was reconstituted with Factor IX. When pretreated with Factor IXai, mice subjected to middle cerebral artery occlusion and reperfusion demonstrated an 1.8-fold reduced microvascular fibrin and platelet deposition, 2.4-fold increased cerebral perfusion, and significantly smaller cerebral infarcts 3.5-fold than vehicle-treated controls ($p<0.05$, 0.05, and 0.05, respectively). Factor IXai-mediated cerebroprotection was not associated with ICH at therapeutically effective doses, and was seen even when Factor IXai was administered after the onset of cerebral ischemia. In contrast, a less targeted anticoagulant strategy with heparin reduced cerebral infarction volumes only at doses which increased ICH. Administration of Factor IXai represents a new strategy to treat stroke in evolution without increasing the risk of ICH. The apparent efficacy of Factor IXai when given after stroke suggests that microvascular thrombosis continues to evolve (and may be inhibited) even after occlusion of a major vascular tributary, thereby broadening the potential therapeutic window for its administration.

Timely reestablishment of blood flow to ischemic brain represents the current treatment paradigm for acute stroke (1–3). Administration of a thrombolytic agent, even when given under optimal conditions, may not achieve this desired clinical result. Perfusion often fails to return to preischemic levels (postischemic hypoperfusion), suggesting that ischemic injury is not produced solely by the original occlusion, but that there is also an element of microcirculatory failure. Small early trials of a general anticoagulant strategy involving heparin in stroke were disappointing in that the use of heparin was either ineffective and/or associated with an unacceptably high incidence of hemorrhagic conversion (in up to 14% of treated patients) (4–7,7–9). Although the current vogue is to use recombinant tissue plasminogen activator (tPA) to achieve thrombolysis in ischemic stroke, this approach is also associated with an increased risk of intracerebral hemorrhage (ICH) (1–3,10). Consequently, there remains a clear need to identify new agents which can promote reperfusion without increasing the risk of ICH.

Following an ischemic event, the vascular wall is modified from its quiescent, anti-adhesive, antithrombotic state, to one which promotes leukocyte adhesion and thrombosis. In acute stroke, active recruitment of leukocytes by adhesion receptors expressed in the ipsilateral microvasculature, such as intercellular adhesion molecule-1 (ICAM-1) (11) and P-selectin (12), potentiates postischemic hypoperfusion. However, experiments with mice deletionally mutant for each of these genes demonstrate that even in their absence, postischemic cerebral blood flow (CBF) returns only partially to baseline after removal of an intraluminal middle cerebral artery occluding suture. This indicates that there exist additional mechanisms responsible for postischemic cerebrovascular no-reflow, especially the possibility that local thrombosis occurs at the level of the microvasculature (distal to the site of primary occlusion) in stroke. Furthermore, if the ischemic insult is particularly severe, reflow continues to worsen over the time subsequent to withdrawal of the occluding suture, suggesting ongoing vascular obstructive processes (such as de novo thrombosis).

These observations provide the basis for exploring the role of general thrombolytic and/or anticoagulant strategies in the murine model of stroke. However, compelling clinical data indicate that agents which selectively limit thrombosis in stroke without increasing ICH will offer unique advantages which are not seen with any agent tested so far. Because the subendothelial vascular matrix in brain tissue is a rich source of tissue factor, we hypothesized that anticoagulant strategis which do not impair tissue-factor mediated hemostatic events might provide a novel means to reduce thrombosis in the microvascular lumen, yet not impair the ability of friable postischemic cerebral microvessels to form effective hemostatic plugs to limit ICH. Heparin or hirudin, which interfere with the final common pathway of coagulation, or thrombolytic agents, which nonselectively lyse fibrin, do not offer the theroretical advantage offered by targeting the intrinsic limb of the coagulation cascade. The current experiments test the hypothesis that selective blockade of IXa/VIIIa/X activation complex assembly using a novel strategy in which a competitive inhibitor of Factor IXa (active-site blocked IXa, Factor IXai), might provide a novel mechanism to limit intravascular thrombosis while preserving mechanisms of extravascular hemostasis, thereby improving stroke outcome without increasing ICH.

Methods

Murine Stroke Model:

Transient focal cerebral ischemia was induced in mice by intralumenal occlusion of the middle cerebral artery (45 minutes) and reperfusion (24 hrs) as previously reported (13). Serial measurements of relative cerebral blood flow (CBF) were recorded via laser doppler flowmetry (13), and infarct volumes (% ipsilateral hemisphere) determined by planimetric/volumetric analysis of triphenyl tetrazolium chloride (TTC)-stained serial cerebral sections (13).

$^{111}$Indium-platelet Studies:

Platelet accumulation was determined using $^{111}$Indium labeled platelets, collected and prepared as previously described (14). Immediately prior to surgery, mice were given $5\times10^6$ $^{111}$In-labeled-platelets intravenously; deposition was quantified after 24 hours by as ipsilateral cpm/contralateral cpm.

Fibrin Immunoblotting/Immunostaining:

The accumulation of fibrin was measured following sacrifice (of fully heparinized animals) using immunoblotting/immunostaining procedures which have been recently described and validated (15). Because fibrin is extremely insoluble, brain tissue extracts were prepared by plasmin digestion, then applied to a standard SDS-polyacrylamide gel for electrophoresis, followed by immunoblotting using a polyclonal rabbit anti-human antibody prepared to gamma—gamma chain dimers present in cross-linked fibrin which can detect murine fibrin, with relatively little cross-reactivity with fibrinogen (16). Fibrin accumulation was reported as an ipsilateral to contralateral ratio. In additional experiments, brains were embedded in paraffin, sectioned, and immunostained using the same anti-fibrin antibody.

Spectrophotometric Hemoglobin Assay and Visual ICH Score:

ICH was quantified by a spectrophotometric-based assay which we have developed and validated (17). In brief, mouse brains were homogenized, sonicated, centrifuged, and methemoglobin in the supernatants converted (using Drabkin's reagent) to cyanomethemoglobin, the concentration of which was assessed by measuring O.D. at 550 nm against a standard curve generated with known amounts of hemoglobin.

Preparation of Factor IXai (18):

Factor IXai was prepared by selectively modifying the active site histidine residue on Factor IXa, using dansyl-glu-gly-arg-chloromethylketone. Proplex was applied to a preparative column containing immobilized calcium-dependent monoclonal antibody to Factor IX. The column was washed, eluted with EDTA-containing buffer, and Factor IX in the eluate (confirmed as a single band on SDS-PAGE) was then activated by applying Factor XIa (incubating in the presence of $CaCl_2$). Purified Factor Ixa was reacted with a 100-fold molar excess of dansyl-glu-gly-arg chloromethylketone, and the mixture dialyzed. The final product (IXai), devoid of procoagulant activity, migrates identically to IXa on SDS-PAGE. This material (Factor IXai) was then used for experiments following filtration (0.2 µm) and chromatography on DETOXI-GEL™ columns, to remove any trace endotoxin contamination (in sample aliquots, there was no detectable lipopolysaccharide). Factor IXai was subsequently frozen into aliquots at −80° C. until the time of use. For those experiments in which Factor IXai was used, it was given as a single intravenous bolus at the indicated times and at the indicated doses.

Modified Cephalin Clotting Time

Equal volumes of factor IX-deficient plasma (American Diagnostica Inc.) and 0.024M celite in 0.05M barbital buffer (Sigma) were combined in silicone-coated glass tubes (Sigma) for 2 minutes at 37° C. To this mixture, an equal volume of 1:16 (v/v) cephalin (10 mg/ml, Sigma) in 0.05M barbital buffer was added, followed by a one-half volume of sample plasma. After the addition of calcium chloride to a final concentration of 0.001M, the time required for clot formation was determined.

Results

To create a stroke in a murine model, a suture is introduced into the cerebral vasculature so that it occludes the orifice of the right middle cerebral artery, rendering the subtended territory ischemic. By withdrawing the suture after a 45 minute period of occlusion, a reperfused model of stroke is created; mice so treated demonstrate focal neurological deficits as well as clear-cut areas of cerebral infarction. Because the occluding suture does not advance beyond the major vascular tributary (the middle cerebral artery), this model provides an excellent opportunity to investigate "downstream" events that occur within the cerebral microvasculature in response to the period of interrupted blood flow. Using this model, the role of microvascular thrombosis was investigated as follows. To demonstrate that platelet-rich thrombotic foci occur within the ischemic cerebral hemisphere, $^{111}$In-labeled platelets were administered to mice immediately prior to the introduction of the intraluminal occluding suture, to track their deposition during the ensuing period of cerebral ischemia and reperfusion. In animals not subjected to the surgical procedure to create stroke, the presence of platelets was approximately equal between the right and left hemispheres, as would be expected [FIG. 11A, left bar]. However, when animals were subjected to stroke (and received only vehicle to control for subsequent experiments), radiolabeled platelets preferentially accumulated in the ischemic (ipsilateral) hemisphere, compared with significantly less deposition in the contralateral (nonischemic) hemisphere [FIG. 11A, middle bar]. These data support the occurrence of platelet-rich thrombi in the ischemic territory. Another line of evidence also supports the occurrence of microvascular thrombosis in stroke. This data comes from the immunodetection of fibrin, using an antibody directed against a neoepitope on the gamma—gamma chain dimer of cross-linked fibrin. Immunoblots demonstrate a band of increased intensity in the ipsilateral (right) hemisphere of vehicle-treated animals subjected to focal cerebral ischemia and reperfusion [FIG. 11B, "Vehicle"]. To demonstrate that fibrin accumulation was due to the deposition of intravascular fibrin (rather than due to nonspecific permeability changes and exposure to subendothelial matrix), fibrin immunostaining clearly localized the increased fibrin to the lumina of ipsilateral intracerebral microvessels [FIG. 11C]. As an in vivo physiological correlate of microvascular thrombosis, relative cerebral blood flow was measured by laser doppler during the occlusive period as well as after stroke. These data [FIG. 11D, bars labelled "Vehicle"] show that the intraluminal suture technique significantly reduces ipsilateral cerebral blood flow during the occlusive period [FIG. 11D, middle panel]. Blood flow remains depressed even 24 hours after removing the intraluminal occluding suture [FIG. 11D, right panel], corresponsding to the platelet, fibrin immunoblot, and fibrin immunostaining data indicating the presence of postischemic microvascular thrombosis.

To help establish a functionally deleterious role of microvascular thrombosis in stroke, experiments were performed to test the effect of inhibiting assembly of the Factor IXa/VIIIa/X activation complex in vivo. This particular strategy was selected based upon the hypothesis that relatively selective inhibition of the intrinsic pathway of coagulation might inhibit intravascular thrombosis yet not impair tissue factor/VIIa-mediated extravascular hemostasis (and hence, may not increase intracerebral hemorrhage at clinically effective doses). Active-site blocked factor IXa (Factor IXai), formed by dansylation of the active site of Factor IXa, demonstrated antithrombotic potency similar to that of heparin when measured in a modified cephalin clotting time assay [FIG. 12], in which the activity of Factor IXa is a rate-limiting step in thrombus formation. To achieve this goal, Factor IXai was administered to mice immediately prior to stroke in various doses. When Factor IXai is administered to animals prior to introduction of the intraluminal occluding suture, there is a significant reduction in the accumulation of radiolabelled platelets in the ipsilateral hemisphere [FIG. 11A, rightmost bar], no apparent increase in the ipsilateral accumulation of fibrin [FIG. 11B, "Factor IXai"], as well as decreased evidence of intravascular fibrin by immunostaining. In addition, there is a significant increase in postischemic blood flow by this treatment, albeit not completely to preischemic levels [FIG. 11D].

The clinical relevance of these observations is underscored by the striking ability of Factor IXai to reduce cerebral infarct volumes [FIG. 13A]. To test whether this infarct size-reducing property of Factor IXai was unique to this compound, or whether a nonspecific anticoagulant would also demonstrate efficacy in this regard, intravenous heparin was also examined at two doses. Only at the highest dose tested (100 U/kg) did heparin reduce cerebral infarct volumes, however, this was at the cost of a significant increase in intracerebral hemorrhage, measured with a recently validated spectrophotometric assay (17)[FIG. 13B]. In sharp contrast, Factor IXai caused an increase in ICH only at the highest dose tested, but did not do so at doses which demonstrated striking efficacy to reduce cerebral infarct volumes [FIG. 13B]. Because a desirable therapeutic agent in stroke will not only reduce cerebral infarction volumes, but will also minimize ICH, the data shown in FIGS. 13A and 13B are displayed with infarct volumes plotted along the ordinate and intracerebral hemorrhage plotted along the abscissa [FIG. 13C]. As can be seen in the figure, Factor IXai appears to be therapeutically superior to heparin, because with heparin, it was a trade-off between infarct volume-reducing efficacy and increasing ICH, which was not the case with Factor IXai (minimized both infarction volumes and ICH). Pilot experiments in which tPA was administered to mice subjected to stroke resulted in reduced cerebral infarction volumes at the cost of increased ICH.

Because therapies directed at improving outcome from acute stroke must be given after clinical presentation, and because fibrin continues to form following the initial ischemic event in stroke, we tested whether Factor IXai might be effective when given following initiation of cerebral ischemia. Factor IXai given after middle cerebral artery occlusion (following removal of the occluding suture) provided significant cerebral protection judged by its ability to significantly reduce cerebral infarction volumes compared with vehicle-treated controls [FIG. 14].

Discussion

The data in these studies demonstrate clear evidence of intravascular thrombus formation (both platelets and fibrin) within the post-ischemic cerebral microvasculature. In fact, the ability of an anticoagulant such as Factor IXai to improve outcome even when given after the onset of the reperfusion phase suggests that the process of microvascular thrombosis is not limited to that which occurs during the major occlusive event. Rather, microvascular thrombosis appears to be a dynamic process which continues to evolve even after recanalazition of the major vascular tributary. The pathophysiological relevance of microvascular thrombosis in stroke is underscored by the ability of Factor IXai to reduce microvascular thrombosis (both platelet and fibrin accumulation are reduced, with an attendant increase in postischemic CBF) and to improve stroke outcome. These potent antithrombotic actions of Factor IXai are likely to be clinically significant in the setting of stroke, because Factor IXai not only reduces infarct volumes in a dose-dependent manner, but it does so even when given after the onset of stroke. In addition, at clinically relevant doses, treatment with Factor IXai does not cause an increase in ICH, making selective inhibition of Factor IXa/VIIIa/X activation complex assembly with Factor IXai an attractive target for stroke therapy in humans.

There are a number of reasons why targetted anticoagulant strategies might be an attractive alternative to the current use of thrombolytic agents in the management of acute stroke, because of their checkered success in clinical trials. Theoretically, an ideal treatment for acute stroke would prevent the formation or induce dissolution of the fibrin-platelet mesh that causes microvascular thrombosis in the ischemic zone without increasing the risk of intracerebral hemorrhage. However, thrombolytic agents which have been studied in clinical trials of acute stroke have consistently increased the risk of intracerebral hemorrhage (1–3, 10). Streptokinase, given in the first several (<6) hours following stroke onset, was associated with an increased rate of hemorrhagic transformation (up to 67%); although there was increased early mortality, surviving patients suffered less residual disability. Administration of tissue-type plasminogen activator (tPA) within 7 hours (particularly within 3 hours) of stroke onset resulted in increased early mortality and increased rates of hemorrhagic conversion (between 7–20%), although survivors demonstrated less residual disability. In order to develop improved anticoagulant or thrombolytic therapies, several animal models of stroke have been examined. These models generally consist of the administration of clotted blood into the internal carotid artery followed by administration of a thrombolytic agent. In rats, tPA administration within 2 hours of stroke improved cerebral blood flow and reduced infarct size by up to 77% (19,20). In a similar rabbit embolic stroke model, tPA was effective at restoring blood flow and reducing infarct size, with occasional appearance of intracerebral hemorrhage (21,22). However, although there are advantages to immediate clot dissolution, there are several potential disadvantages of tPA; in murine models, tPA has been shown to directly mediate excitotoxic neuronal cell injury via extracellular tPA-catalyzed proteolysis of nonfibrin substrates (23–28). Moreover, animal studies (as well as the clinical trials of thrombolytic agents) indicate that there is an attendant increased risk of intracerebral hemorrhage with this therapeutic approach. In preliminary studies in which tPA was given after removal of the MCA occluding suture, doses of tPA which tended to reduce infarct volumes also increased the degree of ICH (Huang, Kim, Pinsky, unpublished observation).

Because of the usually precipitous onset of ischemic stroke, therapy has been targeted primarily towards lysing the major fibrinous/atheroembolic debris which occludes a major vascular tributary to the brain. However, as the current work demonstrates, there is an important component of microvascular thrombosis which occurs downstream from the site of original occlusion, which is likely to be of considerable pathophysiological significance for post-ischemic hypoperfusion (no-reflow) and cerebral injury in evolving stroke. This data is in excellent agreement with that which has been previously reported, in which microthrombi have been topographically localized to the ischemic region in fresh brain infarcts (29). The use of an agent which inhibits assembly of the Factor IXa/VIIIa/X activation complex represents a novel approach to limiting thrombosis which occurs within microvascular lumena, without impairing extravascular hemostasis, the maintenance of which may be critical for preventing ICH. In the current studies, treatment with Factor IXai reduces microvascular platelet and fibrin accumulation, improves postischemic cerebral blood flow, and reduces cerebral infarct volumes in the setting of stroke without increasing ICH.

The potency of Factor IXai as an anticoagulant agent stems from the integral role of activated Factor IX in the coagulation cascade. Not only does a strategy of Factor IXa blockade appear to be effective in the setting of stroke, but it also appears to be effective at preventing progressive coronary artery occlusion induced following the initial application of electric current to the left circumflex coronary artery in dogs (18).

The data which demonstrate that IXai given after the onset of stroke is effective leads to another interesting hypothesis, that the formation of thrombus represents a dynamic equilibrium between the processes of ongoing thrombosis and ongoing fibrinolysis. Even under normal (nonischemic) settings, this dynamic equilibrium has been shown to occur in man (30). The data in the current studies, which show that Factor IXai is effective even when administered after the onset of stroke, suggests that this strategy restores the dynamic equilibrium, which is shifted after cerebral ischemia to favor thrombosis, back towards a more quiescent (antithrombotic) vascular wall phenotype.

As a final consideration, even if thrombolysis successfully removes the major occluding thrombus, and/or anticoagulant strategies are effective to limit progressive microcirculatory thrombosis, blood flow usually fails to return to pre-ischemic levels. This is exemplified by data in the current study, in which although CBF is considerably improved by Factor IXai (which limits fibrin/platelet accumulation), CBF still does not return to preischemic levels. This data supports the existence of multiple effector mechanisms for postischemic cerebral hypoperfusion, including postischemic neutrophil accumulation and consequent microvascular plugging, with P-selectin and ICAM-1 expression by cerebral microvascular endothelial cells being particularly germane in this regard (11,12). When looked at from the perspective of leukocyte adhesion receptor expression, even when these adhesion receptors are absent, CBF levels are improved following stroke compared with controls but do not return to preischemic levels. Taken together, these data suggests that microvascular thrombosis and leukocyte adhesion together contribute to postischemic cerebral hypoperfusion.

In summary, administration of a competitive inhibitor of Factor IXa, active-site blocked Factor IXa, represents a novel therapy for the treatment of stroke. This therapy not only reduces microcirculatory thrombosis, improves postischemic cerebral blood flow, and reduces cerebral tissue injury following stroke, but it can do so even if given after the onset of cerebral ischemia and without increasing the risk of ICH. This combination of beneficial properties and relatively low downside risk of hemorrhagic transformation makes this an extremely attractive approach for further testing and potential clinical trials in human stroke.

REFERENCES

1. The National Institute of Neurological Disorders and Stroke rt-PA Stroke Study Group (1995) *N. Engl. J. Med.* 333:1581–1587.
2. Hacke, W., et al. (1995) *J. A. M. A.* 274(13):1017–1025.
3. del Zoppo, G. J. (1995) *N. Engl. J. Med.* 333(13):1632–1633.
4. Duke R J, et al. (1996) *Annals of Internal Medicine* 105:825–828.
5. Haley E C Jr., et al. (1988) *Stroke* 19:10–14.
6. Slivka A, and Levy D. (1990) *Stroke* 21:1657–1662.
7. Ramirez-Lassepas M, et al. (1986) *Arch. Neurol.* 43:386–390.
8. Bogousslavsky J. and Regli F. (1985) *Acta Neurol Scand* 71:464–471.
9. Cerebral Embolism Study Group (1984) *Stroke* 15:779–789.
10. Hommel, M., et al. (1996) *N. Engl. J. Med.* 335:145–150.
11. Connolly, E. S. Jr., et al. (1996) *J Clin Invest* 97:209–216.
12. Connolly, E. S. Jr., et al. (1997) *Circ. Res.* 81:304–310.
13. Connolly, E. S. Jr., et al. (1996) *Neurosurg.* 38(3):523–532.
14. Naka, Y., et al. (1995) *Circ. Res.* 76:900–906.
15. Lawson, C. A., et al. (1997) *Journal of Clinical Investigation* 99:1729–1738.
16. Lahiri, B., et al. (1981) *Thromb. Res.* 23:103–112.
17. Choudhri, T. F., et al. (1997) *Stroke* 28:2296–2302.
18. Benedict, C. R., et al. (1991) *J. Clin. Invest.* 88:1760–1765.
19. Papadopoulos, S. M., et al. (1987) *J Neurosurg* 67:394–398.
20. Overgaard, K., et al. (1993) *Neurol Res* 15:344–349.
21. Carter, L. P., et al. (1992) *Stroke* 23:883–888.
22. Phillips, D. A., et al. (1990) *Stroke* 21:602–605.
23. Tsirka, S. E., et al. (1997) *Proceedings of the National Academy of Sciences USA* 94:9779–9781.
24. Tsirka, S. E., et al. (1997) *The Journal of Neuroscience* 17:543–552.
25. Korninger, C. and D. Collen (1981) *Thrombosis Haemostasis* 46:561–565.
26. Tsirka, S. E., et al. (1996) *Nature* 384:123–124.
27. Sappino, A. -P., et al. (1993) *Journal of Clinical Investigation* 92:679–685.
28. Tsirka, S. E., et al. (1995) *Nature* 377:340–344.
29. Heye, N., et al. (1992) *Acta Neurologica Scandinavica* 86:450–454.
30. Nossel, H. L. (1981) *Nature* 291:165–167.

EXAMPLE 5

Microvascular Thrombosis as a Pathophysiological Mechanism in Ischemic Stroke and Use of Active-site Blocked Factor IX as a Novel Treatment Ischemic stroke is the third leading cause of death in the United States. Current treatments aim to reestablish perfusion to ischemic brain by thrombolysis, however, they can increase the risk of hemorrhage, particularly in the setting of ischemia. Studies of acute stroke thus far have focused on ischemia associated with thromboembolic occlusion of cerebral vascular tributary. We hypothesize, however, that ischemic injury is not produced solely by the original occlusion, but that the initial ischemic event modifies the microvasculature to trigger further local/microvascular thrombosis which contributes to post-ischemic hypoperfusion (no-reflow). An ideal treatment would overcome post-ischemic microvascular thrombosis and allow reperfusion without increasing the risk of hemorrhage.

Materials and Methods:

We studied post-ischemic microvascular thrombosis in a murine model of ischemic stroke in which the right middle cerebral artery (MCA) is transiently occluded for 45 minutes. The role of platelets and fibrin were investigated using 111-Indium-labeled platelets and fibrin immunostaining. We studied the efficacy of a novel anticoagulant, active-site blocked factor IX (IXAI, 150–300 µg/kg IV), which inhibits the Factor IXA/VIIIa/X activation complex. Outcome indices were platelet accumulation (measured as an ipsilateral to contralateral ratio), relative cerebral blood flow measured by laser doppler (CBF, ratio of ipsilateral to contralateral hemispheric flow), and infarct volume (Inf Volume, % ipsilateral hemisphere by triphenyltetrazolium chloride staining). In addition, intracerebral hemorrhage (ICH) was quantified in homogenized brain tissue using a method which we developed and validated, based on the conversion of hemoglobin to cyanomethemoglobin (OD measured at 550 nm; the amount of intracerebral blood is linearly related to OD).

Results:

TABLE III

|  | Platelets | Fibrin | CBF | Inf Volume | ICH |
| --- | --- | --- | --- | --- | --- |
| No Stroke (n = 11) | 1.1 ± 0.1 | 0 | 110 ± 8 | 0.0 ± 0 | 0.07 ± 0.0 |
| Stroke + Placebo (n = 62) | 2.9 ± 0.3* | ++ | 37 ± 5* | 26 ± 3.7* | 0.15 ± 0.04* |
| Stroke + IXai (n = 48) | 1.6 ± 0.2* | + | 61 ± 6** | 7.4 ± 3.0** | 0.12 ± 0.02 |

(Results are expressed as means ±SEM.
*p < 0.05 vs. no stroke,
**o < 0.01 vs. stroke + placebo)

These data, along with immunohistochemical evidence of intravascular fibrin only in the ischemic hemisphere, show that thrombus accumulates within the post-ischemic cerebral microvasculature. Furthermore, IXai reduces both this platelet and fibrin accumulation, improves CBF, and reduces infarct volumes in a dose-dependent manner. The advantage of IXai in treating stroke without increasing ICH was shown in experiments where it did not increase ICH when compared with controls (0.12±0.02 vs. 0.15±0.04, p=NS). The benefit of IXai was also observed when given after the onset of stroke (placebo infarct volume 39±5.5% vs. IXai 14±2.4%, p<0.05).

Conclusions:

In ischemic regions of brain, platelets and fibrin accumulate to form microvascular thrombosis, contributing to post-ischemic hypoperfusion (no-reflow). Treatment with IXai reduces platelet and fibrin accumulation, improves CBF, and reduces infarct volume without increasing ICH.

EXAMPLE 6

Active-Site Blocked Factor Ixai: An Alternative Anticoagulant for Use in Hemodialysis Significant bleeding complications during hemodialysis (HD) in high-risk patients (GI/intracerebral hemorrhage) have been reported with an incidence as high as 26%. Patients with increased risk of bleeding as well as those with specific contraindications to heparin would greatly benefit from an alternative anticoagulant for use in HD. Active-site blocked factor IXA (Ixai) has previously been shown to selectively block the intrinsic/contact mediated pathway of coagulation in the setting of contact of blood with an extracorporeal circuit, while maintaining extravascular/tissue factor-mediated hemostasis. In order to investigate the use of this novel anticoagulant strategy in the setting of HD and chronic uremia, obstructive renal failure was induced in 11 female mongrel dogs by bilateral ureteral ligation through a midline laparotomy. Renal failure, as indicated by a rise in BUN>65 mg/dl, was reliably induced within 48 hours at which time the animals underwent standard HD using COBE Centrysystem 3 equipped with 300 HG hemodialyzers and standard bicarbonate dialysate (BiCart). Venovenous HD lasted for three hours and was performed on three consecutive days at flows of 300–350 ml/min. HD was successfully completed using Ixai (400–460 µg/kg given at 0 min & 90 min) or standard heparin with equivalent efficacy as reflected by the urea reduction ratio (74.86%±3.43% vs. 78.16%±2.49%, p=43). There was no evidence of gross clot formation in the tubing or resultant increase in circuit pressure. Analysis of data from incisional wound models at 15 min suggested a decreased bleeding tendency in IXai treated animals as compared to those treated with heparin (0.05±0.11 gm vs. 0.38±0.17 gm closed wound, p=0.004; 4.59±1.74 gm vs. 8.75±2.09 gm open wound, p=17). IXai, a selective anticoagulant which confers extracorporeal circuit anticoagulation without compromising extravascular hemostasis, may therefore represent a novel alternative anticoagulant strategy for use in chronic HD.

EXAMPLE 7

Role of Factor IXai in Pulmonary Ischemia and Reperfusion and Role of Factor IXai as an Adjunct to Tissue-type Plasminogen Activator (tPA) in Stroke.

(1) Factor IXai can be effective at lower doses with the lower doses being less likely to cause intracerebral hemorrhage. This Example includes data regarding the dose response range of Factor IXai with respect to its effect on clotting time in the modified cephalin clotting time assay. The dose/response data with respect to intracerebral hemorrhage can be found in the data provided in Example 4.

(2) Factor IXai is effective in other types of ischemia (and reperfusion. New data shown in this example show that when the lungs are subjected to ischemia and reperfusion (by cross-clamping their blood supply, waiting a bit, and then releasing the clamp), Factor IXai is protective. Both the lung function (oxygenation of blood) and survival of the animal which had received Factor IXai was better than that seen in vehicle-treated animals.

(3) Factor IXai may be effective after the thrombotic event; i.e., it is effective when given after stroke, not just beforehand. This data can be found in the information hereinabove in Example 4.

(4) Factor IXai may be useful to lower the dose of thrombolytic therapy necessary to achieve reperfusion (for instance, in heart attacks, stroke, pulmonary emboli, etc.). The data which shows this point is in Table IV hereinbelow. In a stroke model, a dose of tissue-type plasminogen activator (an example of a commonly used thrombolytic agent) which itself did not protect the brain In stroke was given in combination with a dose of Factor IXai which was too low by itself to confer protection; however, the combination was significantly protective (reduced cerebral infarction volume) without causing any excess in intracerebral hemorrhage.

Role of Factor IXai in Pulmonary Ischemia and Reperfusion:

Seven C57BL mice (male 25 gm) were anesthetized with ketamine and xylazine, and a bilateral thoracotomy was performed using a clam-shell incision. A loose suture was placed around the right pulmonary artery, and the left pulmonary hilum was exposed. An intravenous injection was given (0.3 mL of either saline [control, n=4] or Factor IXai [300 µg, n=3]. After 3 minutes, the left pulmonary hilum (pulmonary artery, vein, and bronchus) was cross-clamped for 1 hour to create ischemia, after which the cross-clamp was released and the left lung reperfused and ventilated for 1 hour. After this reperfusion period, the loose suture around the right pulmonary artery was tightened, so that the animal's arterial oxygenation and survival depended solely on the function of the postischemic left lung. The data revealed that in the control group, the mean arterial oxygenation was 66 mm Hg, whereas in the Factor IXai-treated group, it was 120 mm Hg. Factor IXai also improved survival, in that 100% of control animals failed to survive the right pulmonary artery ligation procedure (mean time to death, 10 minutes), whereas 2/3 of the Factor IXai-treated animals survived for 30 minutes (at which time they were sacrificed for arterial blood gas analysis). Taken together, these data show that Factor IXai can protect against ischemia reperfusion injury in this model, and extend the previous data which showed that Factor IXai was protective after middle cerebral artery ischemia and reperfusion.

Role of Factor IXai as an Adjunct to Tissue-type Plasminogen Activator (tPA) in Stroke:

For these data, 17 mice were used, and subjected to middle cerebral artery occlusion (45 minutes) and reperfusion as described hereinabove. Because Factor IXai by itself has been shown to have a dose-related cerebroprotective effect in stroke, a dose was chosen which we had previously shown to be below the protective threshold (50 µg/kg). In the experimental group, mice were given 50 µg/kg of Factor IXai preoperatively, and tPA was given immediately after withdrawal of the occluding suture at a dose of 0.5 mg/kg. Either of these agents when given by themselves at these low doses did not confer cerebral protection. However, compared to control animals which received vehicle alone (n=7), when tPA 0.5 mg/kg and Factor IXai (50 µg/kg) (n=10) were combined, there was significant protection; relative cerebral blood flows are expressed as an ipsilateral/contralateral blood flow ratio (×100), Infarct volumes are expressed as the percent of the ipsilateral hemisphere which was infarcted, and intracerebral hemorrhage was recorded as the optical density at 550 nm (higher numbers mean more hemorrhage, using our recently validated spectrophotometric method for quantifying intracerebral hemorrhage). ***=p<0.001 vs. control.

TABLE IV

| | Relative cerebral blood flow | Infarct Volume | Interacerebral Hemorrhage |
|---|---|---|---|
| Control | 39 ± 6.4% | 29.6 ± 8.4% | 0.112 ± 0.013 |
| IXai + tPA | 72 ± 4.1%*** | 10.0 ± 2.6%*** | 0.110 ± 0.014 |

We conclude that administration of Factor IXai even at low doses can make tPA effective and cerebroprotective, at doses of tPA which otherwise showed no beneficial effects in previous experiments. Note that the combination treatment did not increase the degree of intracerebral hemorrhage.

What is claimed is:

1. A method of inhibiting clot formation in a subject which comprises adding to blood an amount of an inactive recombinant mutein in an amount effective to inhibit clot formation in the subject but which does not significantly interfere with hemostasis when the blood is administered to a patient, wherein the inactive recombinant mutein comprises:

(a) a proteolytically inactive recombinant mutein of Factor IX, or (b) a proteolytically inactive recombinant mutein of Factor IXa and wherein the recombinant mutein comprises a substitution, or addition of one or more amino acids to an active site of wild-type Factor IX or an active site of wild-type Factor IXa resulting in reduced ability to convert Factor X to Factor Xa.

2. The method of claim 1, wherein the patient has experienced an ischemic event.

3. The method of claim 1, wherein the recombinant mutein of Factor IX comprises an amino acid substitution for one or more of His221, Asp269 or Ser365 of wild-type Factor IX.

4. The method of claim 3, wherein the substitution for Ser365 of wild-type Factor IX is alanine.

5. The method of claim 1, wherein the recombinant mutein of Factor IX comprises at least one amino acid substitution from wild-type Factor IX sequence.

6. The method of claim 1, wherein the recombinant mutein of Factor IXa comprises an amino acid substitution for one or more of His41, Asp89 or Ser185 in the heavy chain of wild-type Factor IXa.

7. The method of claim 6, wherein the substitution for Ser185 of wild-type Factor IXa is alanine.

* * * * *

```
                        SEQUENCE LISTING

<160> NUMBER OF SEQ ID NOS: 22

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than serine.

<400> SEQUENCE: 1
tacagttcct ctannncccc ctggggtac                                   29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than serine.

<400> SEQUENCE: 2
tacagttcct ctannncccc ctggggtaca                                  30

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than serine.

<400> SEQUENCE: 3
tacagttcct ctannncccc ctggggtaca a                                31

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than serine.

<400> SEQUENCE: 4
gtacagttcc tctannnccc cctggggtac                                  30
```

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:
    Oligonucleotides for producing Factor IXmi.
<223> OTHER INFORMATION: NNN=the complement to a DNA codon for any one
    of the standard amino acids other than serine.

<400> SEQUENCE: 5
gtacagttcc tctannnccc cctggggtac a                                    31

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
    Oligonucleotides for producing Factor IXmi.
<223> OTHER INFORMATION: NNN=the complement to a DNA codon for any one
    of the standard amino acids other than serine.

<400> SEQUENCE: 6
gtacagttcc tctannnccc cctggggtac aa                                   32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:
    Oligonucleotides for producing Factor IXmi.
<223> OTHER INFORMATION: NNN=the complement to a DNA codon for any one
    of the standard amino acids other than serine.

<400> SEQUENCE: 7
agttacagtt cctctannnc ccctggggt ac                                    32

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:
    Oligonucleotides for producing Factor IXmi.
<223> OTHER INFORMATION: NNN=the complement to a DNA codon for any one
    of the standard amino acids other than serine.

<400> SEQUENCE: 8
agttacagtt cctctannnc ccctggggt aca                                   33

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence:
    Oligonucleotides for producing Factor IXmi.
<223> OTHER INFORMATION: NNN=the complement to a DNA codon for any one
    of the standard amino acids other than serine.

<400> SEQUENCE: 9
agttacagtt cctctannnc ccctggggt acaa                                  34

<210> SEQ ID NO 10
<211> LENGTH: 29
<212> TYPE: DNA

```
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 10
attcatgtta gtannntaac gcgaagacc                                    29

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 11
attcatgtta gtannntaac gcgaagacct                                   30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 12
attcatgtta gtannntaac gcgaagacct t                                 31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 13
tattcatgtt agtannntaa cgcgaagacc                                   30

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 14
tattcatgtt agtannntaa cgcgaagacc t                                 31

<210> SEQ ID NO 15
<211> LENGTH: 32
```

```
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 15
tattcatgtt agtannntaa cgcgaagacc tt                              32

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 16
ttattcatgt tagtannnta acgcgaagac c                               31

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 17
ttattcatgt tagtannnta acgcgaagac ct                              32

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than aspartic acid
      and cysteine.

<400> SEQUENCE: 18
ttattcatgt tagtannnta acgcgaagac ctt                             33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:
      Oligonucleotides for producing Factor IXmi.
<223> OTHER INFORMATION: NNN=the complement to a DNA codon for any one
      of the standard amino acids other than histidine and
      cysteine.

<400> SEQUENCE: 19
ttacattgac gacggnnnac acaactttga cca                             33

<210> SEQ ID NO 20
```

<211> LENGTH: 30
<212> TYPE: DNA
<213> ORGANISM: Artificial Sequence
<220> FEATURE:
<223> OTHER INFORMATION: Description of Artificial Sequence:
      Oligonucleotide Primer  for producing Factor IXmi.

<400> SEQUENCE: 20
gtacagttcc tctacgaccc cctggggtac                                         30

<210> SEQ ID NO 21
<211> LENGTH: 461
<212> TYPE: PRT
<213> ORGANISM: Homo Sapien

<400> SEQUENCE: 21

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320
```

```
Leu Asp Glu Pro Leu Val Leu Asn Ser Tyr Val Thr Pro Ile Cys Ile
            325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
            355                 360                 365
Leu Gln Tyr Leu Arg Val Pro Leu Val Asp Arg Ala Thr Cys Leu Arg
        370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
            405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
            435                 440                 445
Arg Tyr Val Asn Trp Ile Lys Glu Lys Thr Lys Leu Thr
        450                 455                 460

<210> SEQ ID NO 22
<211> LENGTH: 2775
<212> TYPE: DNA
<213> ORGANISM: Homo Sapien

<400> SEQUENCE: 22
atgcagcgcg tgaacatgat catggcagaa tcaccaggcc tcatcaccat ctgccttta        60 ggatatctac tcagtgctga atgtacagtt tttcttgatc atgaaaacgc caacaaaatt      120
ctgaatcggc aaagaggta taattcaggt aaattggaag agtttgttca agggaacctt       180
gagagagaat gtatggaaga aaagtgtagt tttgaagaag cacgagaagt tttttgaaaac     240 actgaaagaa caactgaatt ttggaagcag tatgttgatg gagatcagtg tgagtccaat     300
ccatgtttaa atggcggcag ttgcaaggat gacattaatt cctatgaatg ttggtgtccc     360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga     540
gtttctgttt cacaaacttc taagctcacc cgtgctgaga ctgttttttcc tgatgtggac     600 tatgtaaatt ctactgaagc tgaaaccatt ttggataaca tcactcaaag cacccaatca     660
tttaatgact tcactcgggt tgttggtgga aagatgcca aaccaggtca attcccttgg     720
caggttgttt tgaatggtaa agttgatgca ttctgtggag gctctatcgt taatgaaaaa     780
tggattgtaa ctgctgccca ctgtgttgaa actggtgtta aaattacagt tgtcgcaggt     840
gaacataata ttgaggagac agaacataca gagcaaaagc gaaatgtgat tcgaattatt     900
cctcaccaca actacaatgc agctattaat aagtacaacc atgacattgc ccttctggaa     960
ctggacgaac cctagtgct aaacagctac gttacaccta tttgcattgc tgacaaggaa    1020
tacacgaaca tcttcctcaa atttggatct ggctatgtaa gtggctgggg aagagtcttc    1080
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac ccatgttac tgaagtgaa     1260 gggaccagtt tcttaactgg aattattagc tggggtgaag agtgtgcaat gaaaggcaaa    1320
```

-continued

```
tatgaatat ataccaaggt atcccggtat gtcaactgga ttaaggaaaa aacaaagctc    1380
acttaatgaa agatggattt ccaaggttaa ttcattggaa ttgaaaatta acagggcctc    1440
tcactaacta atcactttcc catcttttgt tagatttgaa tatatacatt ctatgatcat    1500 tgcttttct ctttacaggg gagaatttca tattttacct gagcaaattg attagaaaat    1560
ggaaccacta gaggaatata atgtgttagg aaattacagt catttctaag ggcccagccc    1620
ttgacaaaat tgtgaagtta aattctccac tctgtccatc agatactatg gttctccact    1680
atggcaacta actcactcaa ttttccctcc ttagcagcat tccatcttcc cgatcttctt    1740
tgcttctcca accaaaacat caatgtttat tagttctgta tacagtacag gatctttggt    1800
ctactctatc acaaggccag taccacactc atgaagaaag aacacaggag tagctgagag    1860
gctaaaactc atcaaaaaca ctactccttt tcctctaccc tattcctcaa tcttttacct    1920
tttccaaatc ccaatcccca aatcagtttt tctctttctt actccctctc tcccttttac    1980
cctccatggt cgttaaagga gagatgggga gcatcattct gttatacttc tgtacacagt    2040
tatacatgtc tatcaaaccc agacttgctt ccatagtgga gacttgcttt tcagaacata    2100
gggatgaagt aaggtgcctg aaaagtttgg gggaaaagtt tctttcagag agttaagtta    2160
ttttatatat ataatatata tataaaatat ataatataca atataaatat atagtgtgtg    2220
tgtgtatgcg tgtgtgtaga cacacacgca tacacacata taatggaagc aataagccat    2280
tctaagagct tgtatggtta tggaggtctg actaggcatg atttcacgaa ggcaagattg    2340
gcatatcatt gtaactaaaa aagctgacat tgacccagac atattgtact ctttctaaaa    2400
ataataataa taatgctaac agaaagaaga gaaccgttcg tttgcaatct acagctagta    2460
gagactttga ggaagaattc aacagtgtgt cttcagcagt gttcagagcc aagcaagaag    2520
ttgaagttgc ctagaccaga ggacataagt atcatgtctc ctttaactag catacccga    2580 agtggagaag ggtgcagcag gctcaaaggc ataagtcatt ccaatcagcc aactaagttg    2640 tcctttctg gtttcgtgtt caccatggaa cattttgatt atagttaatc cttctatctt    2700
gaatcttcta gagagttgct gaccaactga cgtatgtttc cctttgtgaa ttaataaact    2760
ggtgttctgg ttcat                                                    2775
```